(12) United States Patent
Cosford et al.

(10) Patent No.: US 10,071,976 B2
(45) Date of Patent: Sep. 11, 2018

(54) SMALL MOLECULE FATTY ACID SYNTHASE INHIBITORS

(71) Applicant: Sanford Burnham Prebys Medical Discovery Institute, La Jolla, CA (US)

(72) Inventors: Nicholas D. P. Cosford, La Jolla, CA (US); Jeffrey Smith, La Jolla, CA (US)

(73) Assignee: SANFORD BURNHAM PREBYS MEDICAL DISCOVERY INSTITUTE, La Jolla, CA (US)

( * ) Notice: Subject to any disclaimer, the term of this patent is extended or adjusted under 35 U.S.C. 154(b) by 0 days.

(21) Appl. No.: 15/123,218

(22) PCT Filed: Mar. 5, 2015

(86) PCT No.: PCT/US2015/019032
§ 371 (c)(1),
(2) Date: Sep. 1, 2016

(87) PCT Pub. No.: WO2015/134790
PCT Pub. Date: Sep. 11, 2015

(65) Prior Publication Data
US 2017/0066731 A1 Mar. 9, 2017

Related U.S. Application Data

(60) Provisional application No. 62/110,298, filed on Jan. 30, 2015, provisional application No. 61/949,486, filed on Mar. 7, 2014.

(51) Int. Cl.
| | | |
|---|---|---|
| *C07D 277/42* | (2006.01) |
| *C07D 277/44* | (2006.01) |
| *C07D 277/46* | (2006.01) |
| *C07D 417/12* | (2006.01) |
| *A61K 31/426* | (2006.01) |
| *A61K 31/427* | (2006.01) |
| *A61K 31/5377* | (2006.01) |
| *C07D 277/26* | (2006.01) |
| *C07D 277/40* | (2006.01) |
| *C07D 417/04* | (2006.01) |

(52) U.S. Cl.
CPC .......... *C07D 277/46* (2013.01); *A61K 31/426* (2013.01); *A61K 31/427* (2013.01); *A61K 31/5377* (2013.01); *C07D 277/26* (2013.01); *C07D 277/40* (2013.01); *C07D 277/42* (2013.01); *C07D 417/04* (2013.01); *C07D 417/12* (2013.01)

(58) Field of Classification Search
CPC .. C07D 277/42; C07D 277/44; C07D 277/46; C07D 417/12
See application file for complete search history.

(56) References Cited

U.S. PATENT DOCUMENTS

2005/0053631 A1    3/2005   D'Arcangelis et al.

FOREIGN PATENT DOCUMENTS

| WO | WO-2002/051410 A2 * | 7/2002 |
| WO | WO-2009002933 A1 | 12/2008 |
| WO | WO-2012064632 A1 | 5/2012 |
| WO | WO-2012100223 A1 | 7/2012 |
| WO | WO-2015134790 A1 | 9/2015 |

OTHER PUBLICATIONS

Chemical Abstracts Registry No. 1371669-45-2, indexed in the Registry file on STN CAS Online on Apr. 30, 2012.*
PubChem CID 70680663, National Center for Biotechnology Information. PubChem Compound Database; CID=70680663, https://pubchem.ncbi.nlm.nih.gov/compound/70680663 (accessed Sep. 21, 2017), Available Nov. 4, 2013.*
Chemical Abstracts Registry No. 1111534-76-9, indexed in the Registry file on STN CAS Online Feb. 25, 2009.*
Chemical Abstracts Registry No. 940795-65-3, indexed in the Registry file on STN CAS Online Jul. 2, 2007.*
Chemical Abstracts Registry No. 905778-56-5, indexed in the Registry file on STN CAS Online Sep. 3, 2006.*
Chemical Abstracts Registry No. 1223281-95-5, indexed in the Registry file on STN CAS Online May 14, 2010.*
Chemical Abstracts Registry No. 1223398-60-4, indexed in the Registry file on STN CAS Online May 14, 2010.*
PubChem CID 70680653, National Center for Biotechnology Information. PubChem Compound Database; CID=70680653, https://pubchem.ncbi.nlm. nih.gov/compound/70680653 (accessed Sep. 21, 2017), Available Nov. 4, 2013.*
PubChem CID 70680671, National Center for Biotechnology Information. PubChem Compound Database; CID=70680671, https://pubchem.ncbi.nlm.nih. gov/compound/70680671 (accessed Sep. 21, 2017), Available Nov. 4, 2013.*
Chemical Abstracts Registry No. 620577-53-9, indexed in the Registry file on STN CAS Online Nov. 25, 2003.*
PubChem CID 1811797, National Center for Biotechnology Information. PubChem Compound Database; CID=1811797, https://pubchem.ncbi.nlm.nih.gov/compound/1811797 (accessed Jan. 30, 2018), create date Jul. 12, 2005.*
PubChem CID 4501382, National Center for Biotechnology Information. PubChem Compound Database; CID=4501382, https://pubchem.ncbi.nlm.nih.gov/compound/4501382 (accessed Jan. 30, 2018), create date Sep. 15, 2005.*
PubChem CID 22432805—National Center for Biotechnology Information. PubChem Compound Database; CID=22432805, https://pubchem.ncbi.nlm.nih.gov/compound/22432805 (accessed Apr. 20, 2018), create date Dec. 5, 2007.*
PubChem CID 4501383—National Center for Biotechnology Information. PubChem Compound Database; CID=4501383, https://pubchem.ncbi.nlm.nih.gov/compound/4501383 (accessed Apr. 20, 2018), create date Sep. 15, 2005.*

(Continued)

*Primary Examiner* — Laura L. Stockton
(74) *Attorney, Agent, or Firm* — Wilson, Sonsini, Goodrich & Rosati

(57) ABSTRACT

Provided herein are small molecule Fatty Acid Synthase Inhibitors, compositions comprising the compounds, and methods of using the compounds and compositions comprising the compounds.

4 Claims, 4 Drawing Sheets

(56) References Cited

OTHER PUBLICATIONS

Chemical Abstracts Registry No. 622353-16-6, indexed in the Registry file on Dec. 1, 2003.*
Chemical Abstracts Registry No. 893650-15-2, indexed in the Registry file on Jul. 17, 2006.*
Carvalho et al. Fatty acid synthase inhibition with Orlistat promotes apoptosis and reduces cell growth and lymph node metastasis in a mouse melanoma model. Int J Cancer 123(11):2557-2565 (2008).
Cherry et al. COPI activity coupled with fatty acid biosynthesis is required for viral replication. PLoS Pathogens 2(10): e102 (2006).
Cho. Recent Advances in Oral Prodrug Discovery. Annual Reports in Medicinal Chemistry 41:395-407 (2006).
Flavin et al. Fatty acid synthase as a potential therapeutic target in cancer. Future Oncol 6(4):551-562 (2010).
Fukusawa et al. Enhancement of de novo fatty acid biosynthesis in hepatic cell line Huh7 expressing hepatitis C virus core protein. Biol Pharm Bull 29(9):1958-1961 (2006).
Higuchi et al. Pro-drugs as Novel Delivery Systems, vol. 14 of the A.C.S. Symposium Series (1975).
Innocenzi et al. Fatty acid synthase expression in melanoma. J Cutan Pathol 30(1):23-28 (2003).
Kapadia et al. Hepatitis C virus RNA replication is regulated by host geranylgeranylation and fatty acids. PNAS USA 102(7):2561-2566 (2005).
Kapur et al. Fatty acid synthase expression in cutaneous melanocytic neoplasms. Modern pathology 18(8):1107-1112 (2005).
Kridel et al. Fatty acid synthase inhibitors: new directions for oncology. Expert Opin Investig Drugs 16(141):1817-1829 (2007).
Kridel et al. Orlistat is a novel inhibitor of fatty acid synthase with antitumor activity. Cancer Res 64:2070-2075 (2004).
Kuhajda et al. Synthesis and antitumor activity of an inhibitor of fatty acid synthase. PNAS USA 97:3450-3454 (2000).
Kuhajda. Fatty acid synthase and cancer: new application of an old pathway. Cancer Res 66:5977-5980 (2006).
Menendez et al. Inhibition of fatty acid synthase (FAS) suppresses HER2/neu (erbB-2) oncogene overexpression in cancer cells. PNAS USA 101:10715-10720 (2004).
Ngo et al. Inhibition of isolated Mycobacterium tuberculosis fatty acid synthase I by pyrazinamide analogs. Antimicrobial agents and Chemotherapy 51(7):2430-2435 (2007).
Nogrady. Medicinal Chemistry A Biochemical Approach, Oxford University Press, New York, pp. 388-392 (1985).
Oslob et al. Imidazopyridine-Based Fatty Acid Synthase Inhibitors That Show Anti-HCV Activity and in Vivo Target Modulation. ACS Med Chem Lett 4(1):113-117 (2012).
Pandey et al. Anti-cancer drugs targeting fatty acid synthase (FAS). Recent Pat Anticancer Drug Discov. 7(2):185-197 (2012).
PCT/US2015/019032 International Search Report and Written Opinion dated Jun. 16, 2015.
Rooseboom et al. Enzyme-catalyzed activation of anticancer prodrugs. Pharmacological Reviews 56:53-102 (2004).
Seguin et al. The fatty acid synthase inhibitor orlistat reduces experimental metastases and angiogenesis in B16-F10 melanomas. Br J Cancer 107(6):977-987 (2012).
Silverman. The Organic Chemistry of Drug Design and Drug Action, Academic Press, Inc., San Diego, pp. 352-401 (1992).
Wakil et al. Fatty acid metabolism: target for metabolic syndrome. J Lipid Res 50(Suppl): S138-S143 (2009).

* cited by examiner

Dose response curve of palmitate synthesis inhibition by compound 37 in UACC-903

Eadie-Hofstee analysis of compound 37 with FASN-TE

SMALL MOLECULE FATTY ACID SYNTHASE INHIBITORS

RELATED APPLICATIONS

This application is filed pursuant to 35 U.S.C. § 371 as a United States National Phase Application of International Application No. PCT/US2015/019032, filed Mar. 5, 2015, which claims the benefit of U.S. Provisional Patent Application No. 61/949,486 entitled "SMALL MOLECULE FATTY ACID SYNTHASE INHIBITORS" filed on Mar. 7, 2014, and U.S. Provisional Patent Application No. 62/110,298 entitled "SMALL MOLECULE FATTY ACID SYNTHASE INHIBITORS" filed on Jan. 30, 2015, each of which is incorporated herein by reference in its entirety.

SUMMARY OF THE INVENTION

Described herein are compounds that inhibit the activity of the Fatty Acid Synthase (hereinafter "FASN", also known as "FAS"). In one aspect, compounds described herein are used for treating a disease or condition via inhibition of the thioesterase domain of FASN (FASN-TE) in a subject in need thereof.

In one aspect, described herein is a method for treating or preventing a disease or condition in a mammal that would benefit from the inhibition or reduction of Fatty Acid Synthase activity comprising administering an inhibitor of the thioesterase enzymatic domain of Fatty Acid Synthase to the mammal in need thereof. In some embodiments, the inhibitor of the thioesterase enzymatic domain of Fatty Acid Synthase is a small molecule. In some embodiments, the inhibitor of the thioesterase enzymatic domain of Fatty Acid Synthase is a selective inhibitor of the thioesterase enzymatic domain of Fatty Acid Synthase. In some embodiments, the inhibitor of the thioesterase enzymatic domain of Fatty Acid Synthase is selective for the thioesterase enzymatic domain of Fatty Acid Synthase over other human thioesterases. In some embodiments, the inhibitor of the thioesterase enzymatic domain of Fatty Acid Synthase is a compound having the structure of Formula (I), Formula (Ia), Formula (Ib), Formula (Ic), Formula (Id), Formula (II), Formula (III), Formula (IV), or Formula (V), or a pharmaceutically acceptable salt thereof.

In one aspect, described herein is a method for treating or preventing a disease or condition by inhibition of Fatty Acid Synthase (FASN) in a human which comprises administering to said human an effective amount of a compound that has the structure of Formula (I), or a pharmaceutically acceptable salt, or solvate thereof:

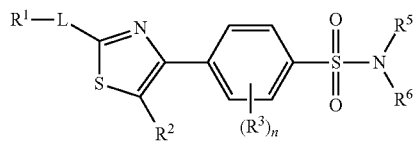

Formula (I)

wherein:
$R^1$ is $C_1$-$C_8$alkyl, substituted or unsubstituted $C_1$-$C_8$haloalkyl, substituted or unsubstituted $C_3$-$C_8$cycloalkyl, substituted or unsubstituted $C_2$-$C_8$heterocycloalkyl, substituted or unsubstituted aryl, substituted or unsubstituted heteroaryl, substituted or unsubstituted —$C_1$-$C_2$alkylene(aryl), or substituted or unsubstituted —$C_1$-$C_2$alkylene(heteroaryl);

L is absent, $C_1$-$C_4$alkylene, —N($R^4$)—, —CH=N—NR$^4$—, —N($R^4$)C(=O)—, —C(=O)N($R^4$)—, —C(=O)N($R^4$)($C_1$-$C_4$alkylene)-, —N($R^4$)C(=O)($C_1$-$C_4$alkylene)-, —($C_1$-$C_4$alkylene)C(=O) N($R^4$)—, —($C_1$-$C_4$alkylene)N($R^4$)C(=O)—, —C(=O)N($R^4$)($C_1$-$C_4$alkylene)O—, —N($R^4$)C(=O)($C_1$-$C_4$alkylene)O—, —O($C_1$-$C_4$alkylene)C(=O)N($R^4$)—, or —O($C_1$-$C_4$alkylene) N($R^4$)C(=O)—;

$R^2$ is hydrogen, halogen, —CN, —OH, substituted or unsubstituted $C_1$-$C_6$alkyl, substituted or unsubstituted $C_1$-$C_6$haloalkyl, substituted or unsubstituted $C_1$-$C_6$alkoxy, or substituted or unsubstituted $C_1$-$C_6$haloalkoxy;

each $R^3$ is independently selected from the group consisting of hydrogen, halogen, —CN, —OH, substituted or unsubstituted $C_1$-$C_6$alkyl, substituted or unsubstituted $C_1$-$C_6$haloalkyl, substituted or unsubstituted $C_1$-$C_6$alkoxy, and substituted or unsubstituted $C_1$-$C_6$haloalkoxy;

n is 0, 1, 2, 3, or 4;

$R^4$ is hydrogen, $C_1$-$C_6$alkyl, $C_1$-$C_6$haloalkyl, $C_3$-$C_8$cycloalkyl, or substituted or unsubstituted aryl;

$R^5$ and $R^6$ are each independently selected from the group consisting of hydrogen, substituted or unsubstituted $C_1$-$C_6$alkyl, substituted or unsubstituted $C_1$-$C_6$haloalkyl, substituted or unsubstituted $C_3$-$C_8$cycloalkyl, substituted or unsubstituted $C_2$-$C_8$heterocycloalkyl, substituted or unsubstituted aryl, substituted or unsubstituted heteroaryl, substituted or unsubstituted —$C_1$-$C_2$alkylene(aryl), and substituted or unsubstituted —$C_1$-$C_2$alkylene(heteroaryl);

or $R^5$ and $R^6$ are taken together with the nitrogen to which they are attached form a substituted or unsubstituted 4-, 5-, 6-, or 7-membered heterocycloalkyl.

Throughout the specification, groups and substituents thereof are chosen by one skilled in the field to provide stable moieties and compounds. For example, in some embodiments, $R^2$ is hydrogen, halogen, —CN, $C_1$-$C_6$alkyl, or $C_1$-$C_6$haloalkyl. In other embodiments, $R^2$ is hydrogen, halogen, —CN, —CH$_3$, —CH$_2$CH$_3$, —CF$_3$, or —CH$_2$CF$_3$. In other embodiments, $R^2$ is hydrogen, halogen, —CH$_3$, or —CF$_3$. In other embodiments, $R^2$ is hydrogen.

In some embodiments, $R^2$ is hydrogen; $R^3$ is hydrogen; and n is 0.

In some embodiments, the compound of Formula (I) has the structure of Formula (Ia):

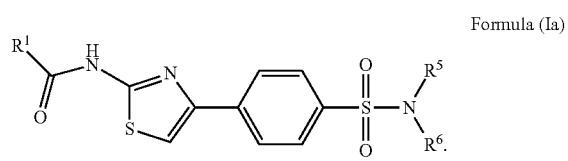

Formula (Ia)

In some embodiments, the compound of Formula (I) has the structure of Formula (Ib), Formula (Ic), or Formula (Id):

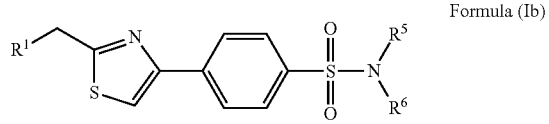

Formula (Ib)

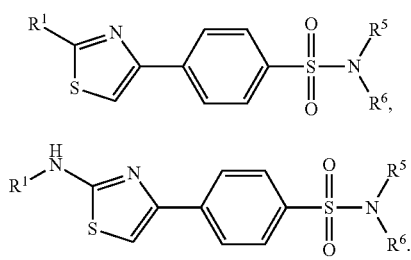

Formula (Ic)

Formula (Id)

In some embodiments, $R^1$ is substituted or unsubstituted $C_1$-$C_8$alkyl.

In some embodiments, $R^1$ is selected from the group consisting of methyl, ethyl, n-propyl, i-propyl, n-butyl, sec-butyl, i-butyl, t-butyl, 1-ethyl-propyl, n-pentyl, n-hexyl, and n-heptyl.

In some embodiments, $R^1$ is 1-ethyl-propyl or sec-butyl.

In some embodiments, $R^1$ is substituted or unsubstituted aryl.

In some embodiments, $R^1$ is phenyl optionally substituted with halogen, —CN, —OH, $C_1$-$C_6$ alkyl, $C_1$-$C_6$haloalkyl, $C_1$-$C_6$alkoxy, or $C_1$-$C_6$haloalkoxy.

In some embodiments, $R^1$ is substituted or unsubstituted $C_3$-$C_8$cycloalkyl.

In some embodiments, $R^1$ is selected from the group consisting of cyclopropyl, cyclobutyl, cyclopentyl, and cyclohexyl.

In some embodiments, $R^5$ and $R^6$ are each independently substituted or unsubstituted $C_1$-$C_6$alkyl.

In some embodiments, $R^5$ and $R^6$ are each independently selected from methyl or ethyl.

In some embodiments, $R^5$ and $R^6$ are taken together with the nitrogen to which they are attached form a substituted or unsubstituted 4-, 5-, 6-, or 7-membered heterocycloalkyl.

In some embodiments, $R^5$ and $R^6$ are taken together with the nitrogen to which they are attached form a pyrrolidinyl, morpholinyl, piperidinyl, 4-methylpiperidinyl, 2-methylpiperidinyl, 3-methylpiperidinyl, thiomorpholinyl, piperazinyl, or 4-methylpiperazinyl.

In some embodiments, $R^1$ is sec-butyl; and $R^5$ and $R^6$ are each ethyl.

In some embodiments, the compound of Formula (I) has one of the following structures:

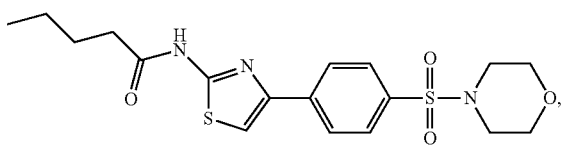

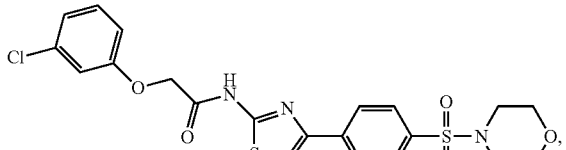

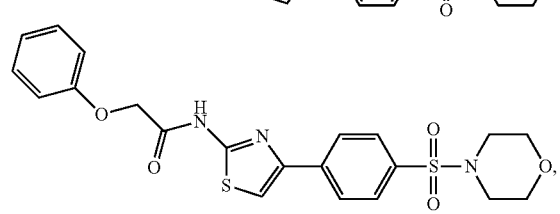

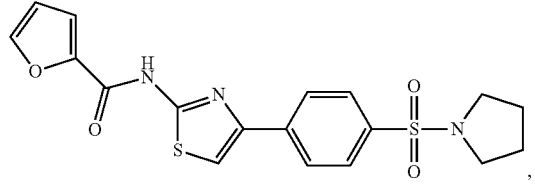

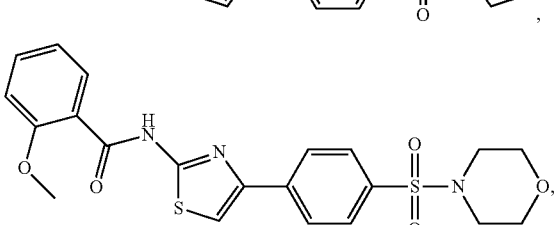

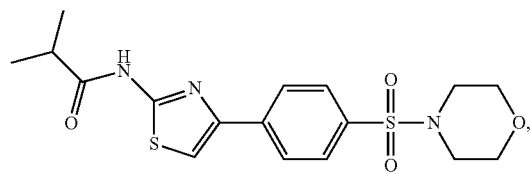

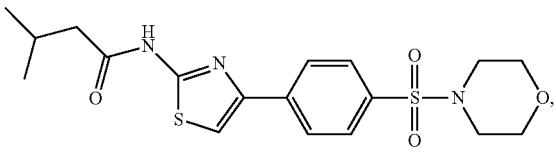

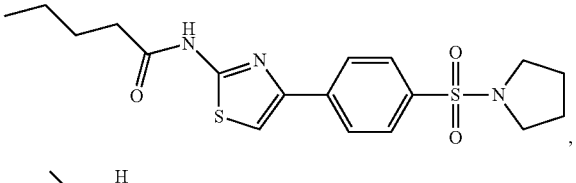

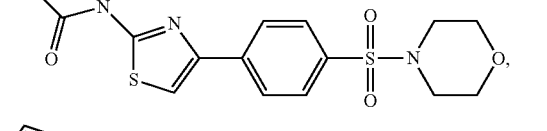

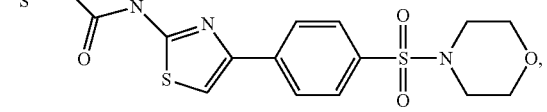

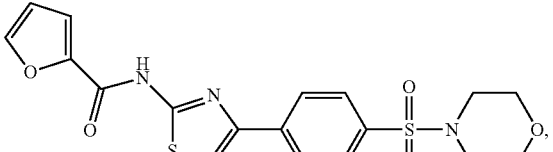

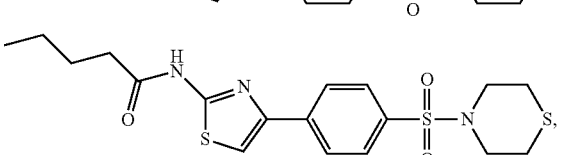

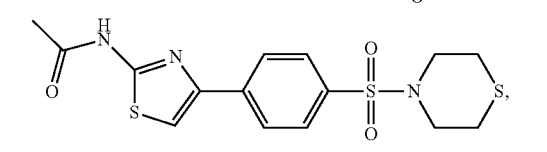

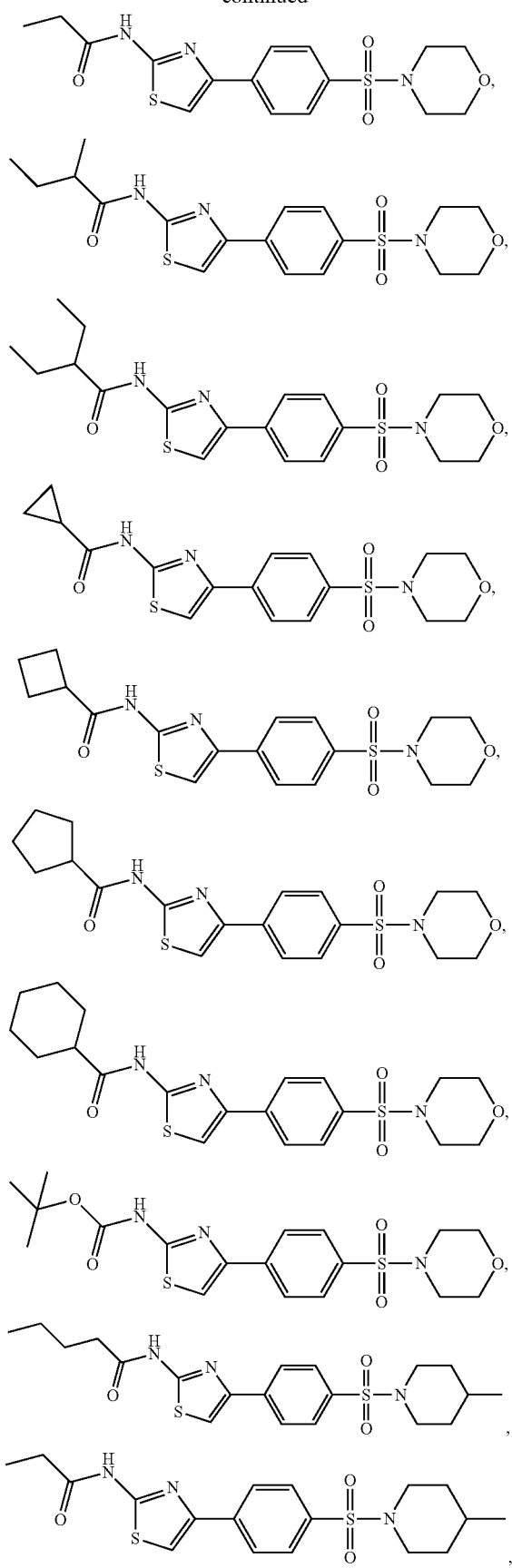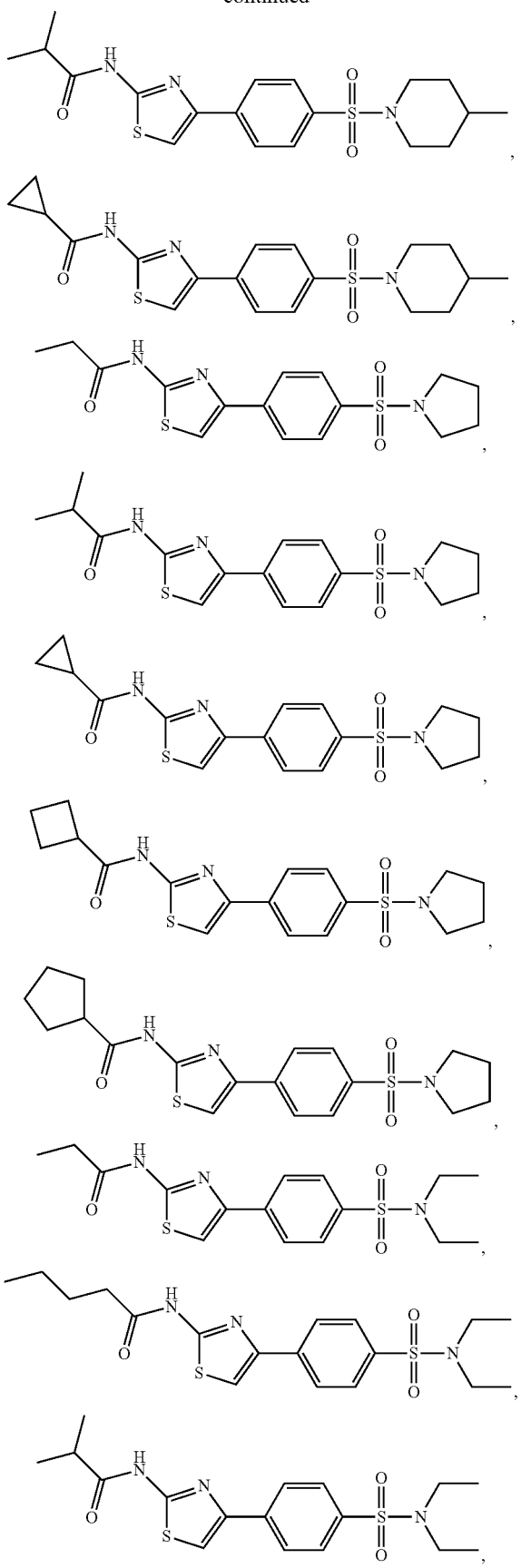

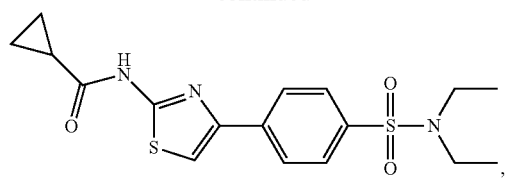
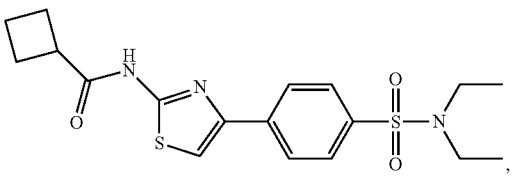
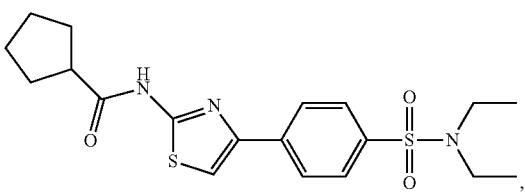
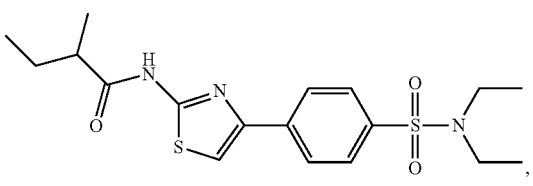
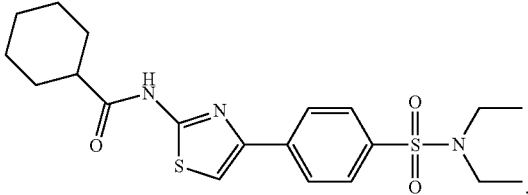
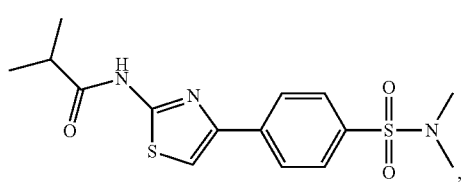
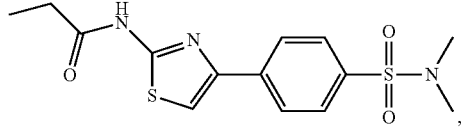
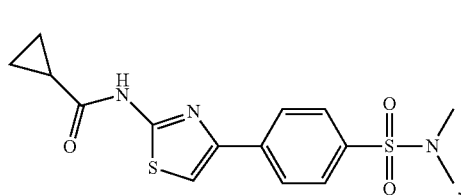
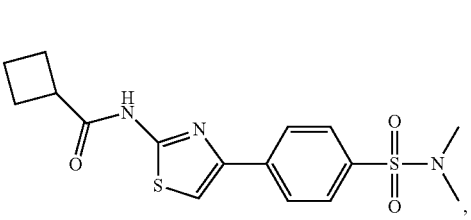
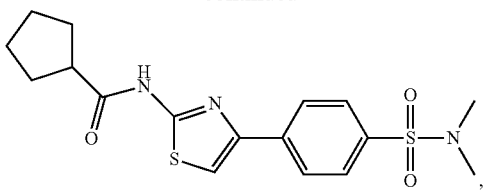
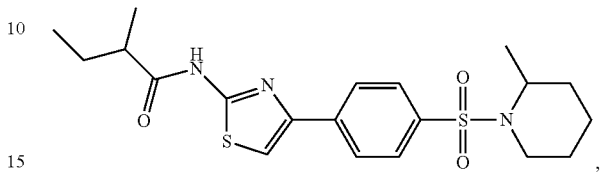
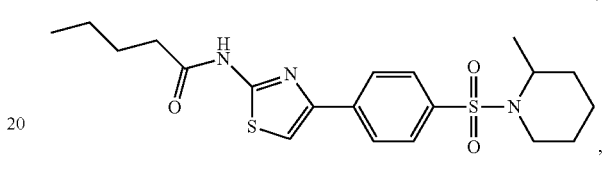
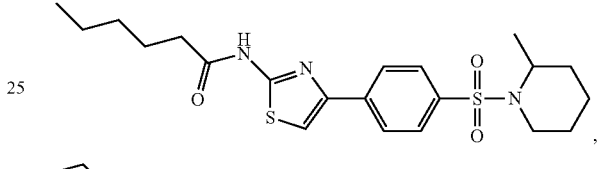
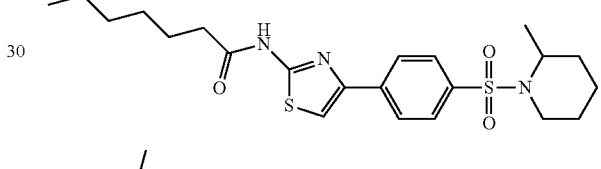
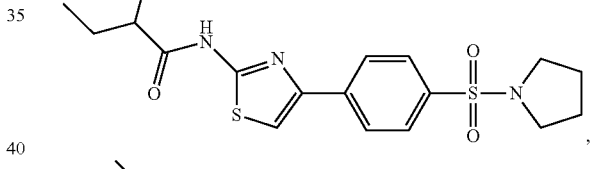
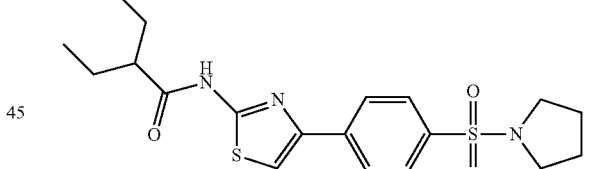
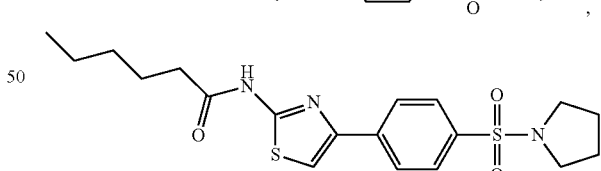
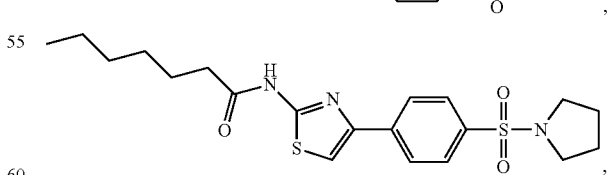
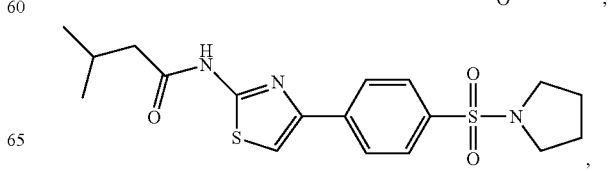

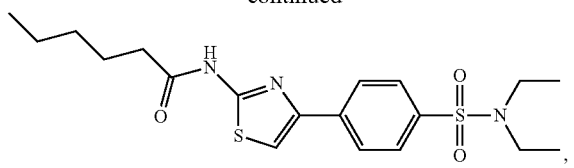
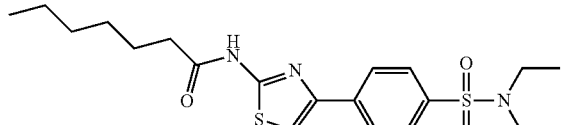
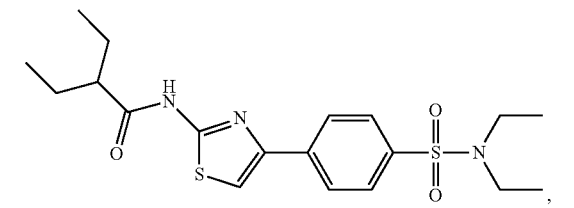
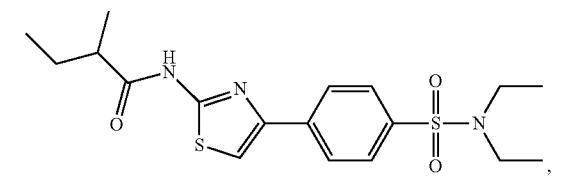
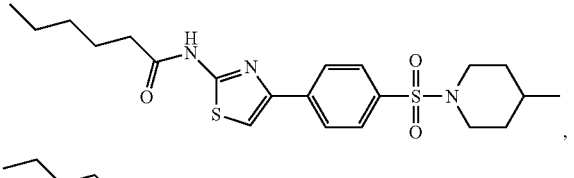
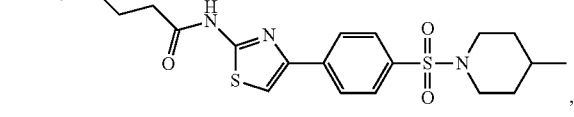
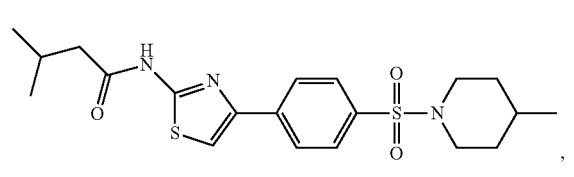
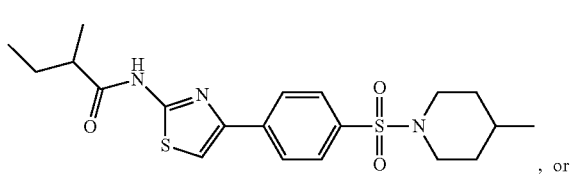
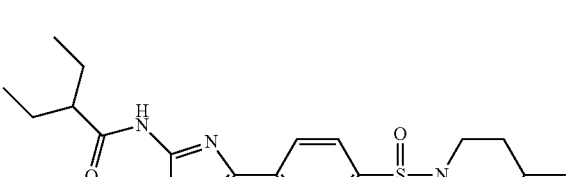, or
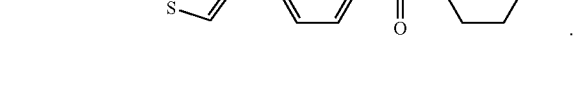
In some embodiments, the compound has one of the following structures:
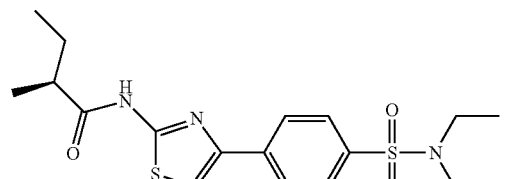
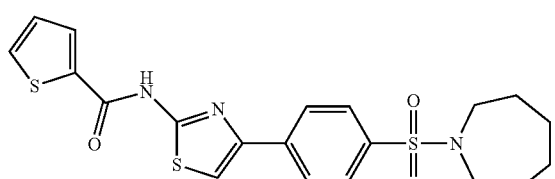
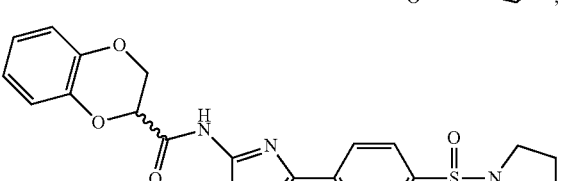
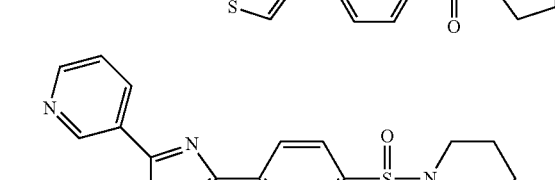
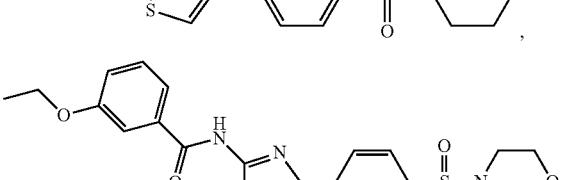
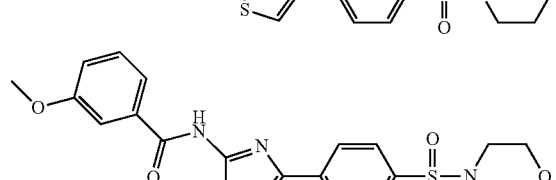
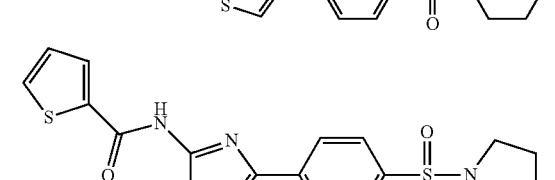
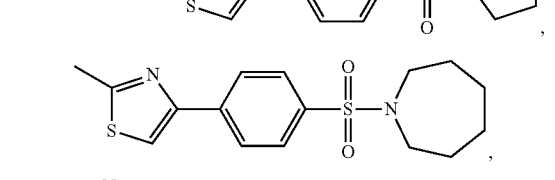
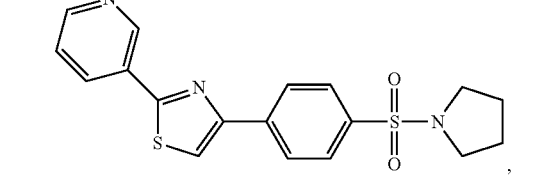

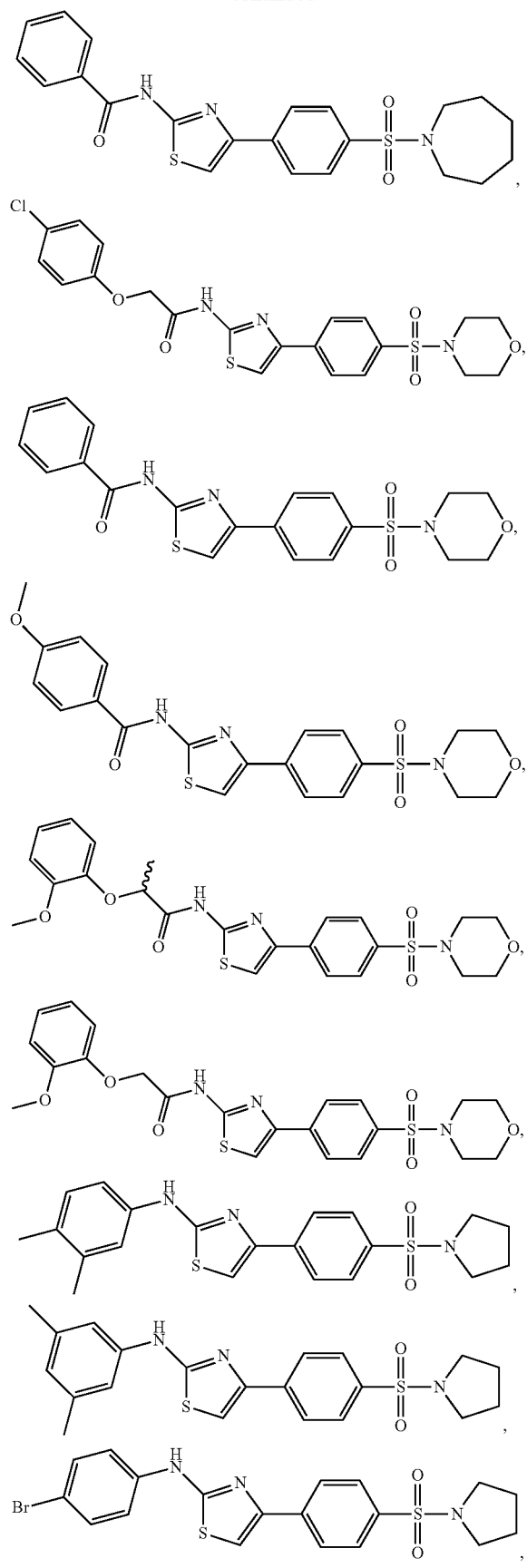
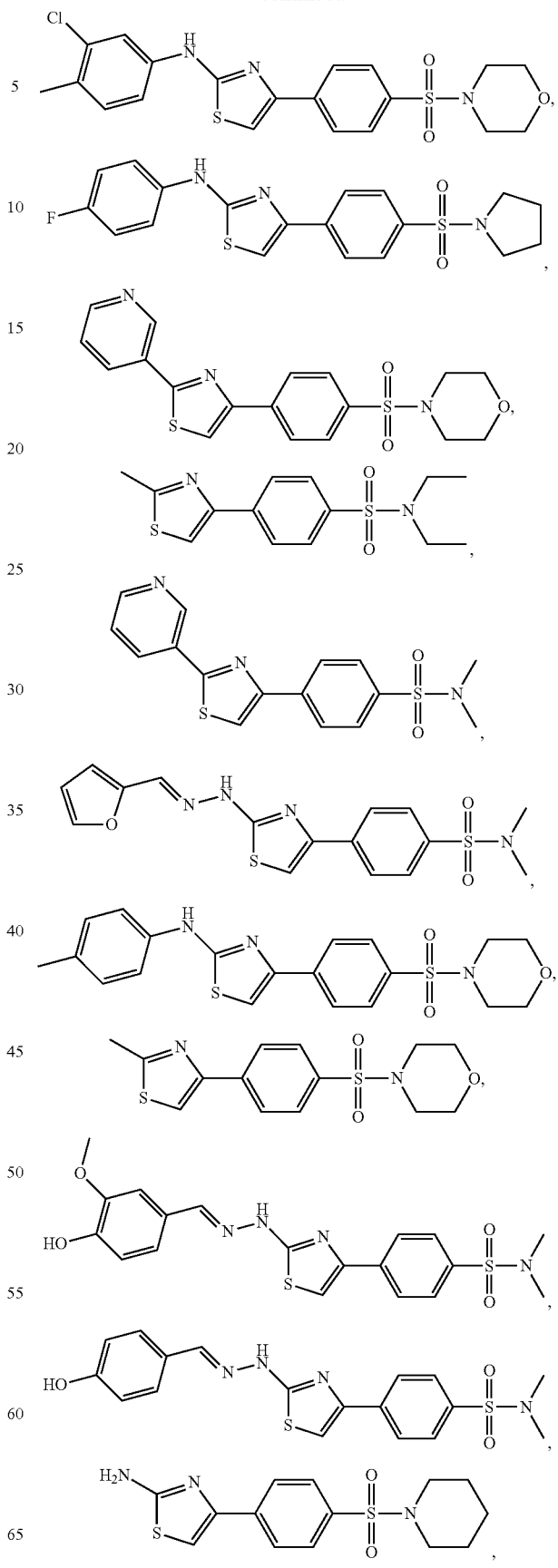

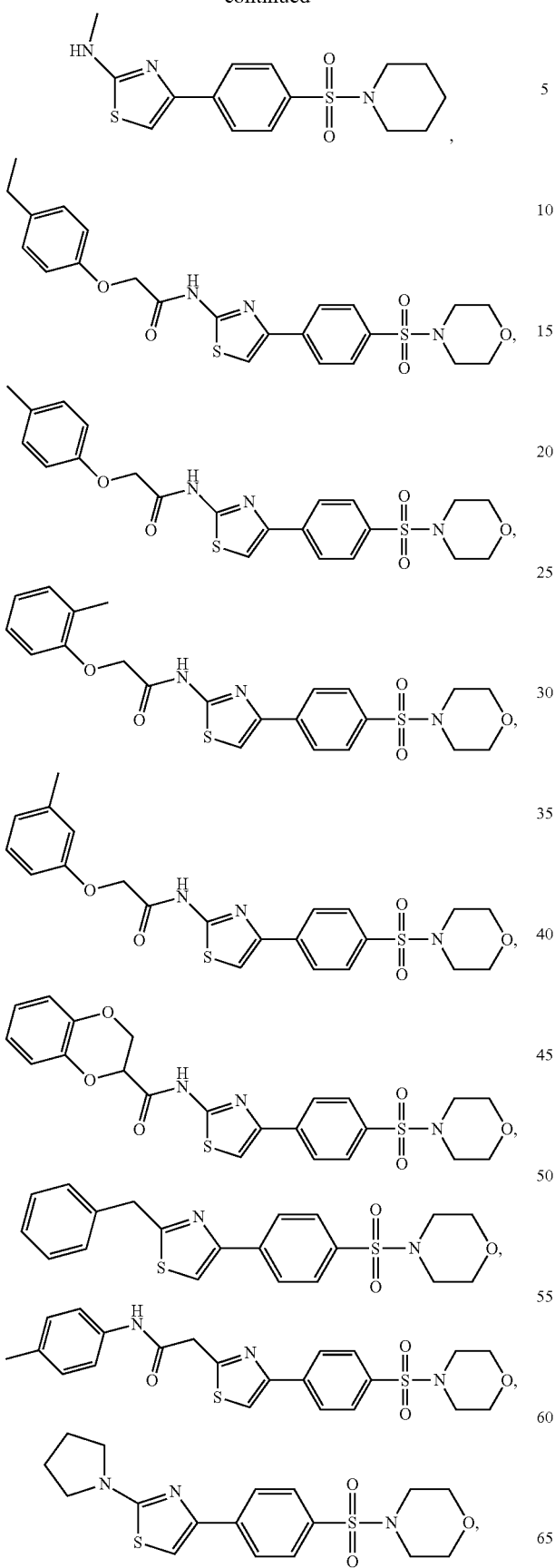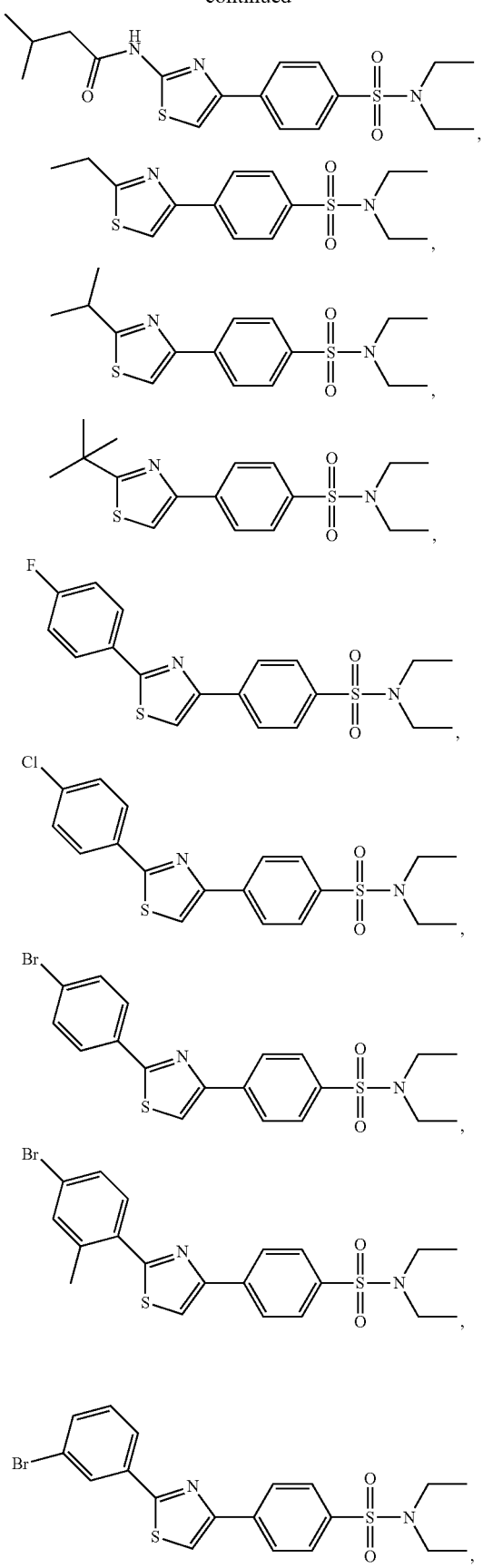

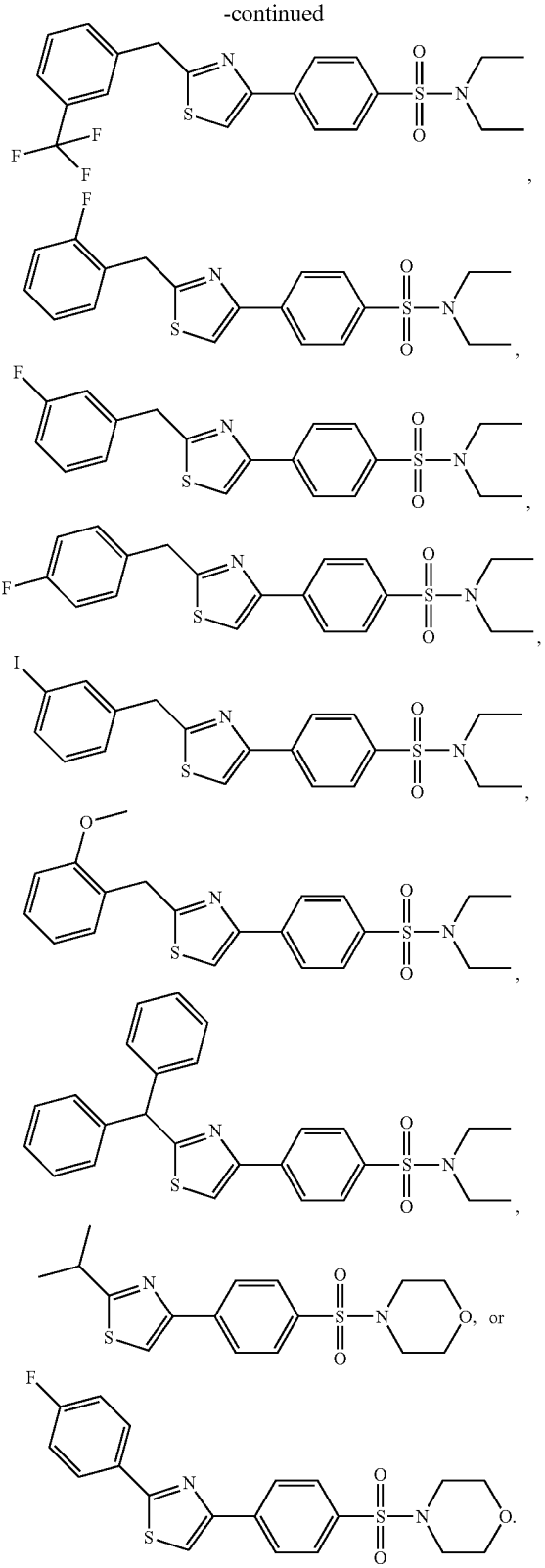

In some embodiments, the disease or condition is treated by inhibition of the thioesterase enzymatic domain of FASN (FASN-TE).

In some embodiments, the disease or condition is cancer or a viral infection.

In some embodiments, the disease or condition is cancer.

In some embodiments, the cancer is selected from prostate, ovarian, breast, liver, endometrial, colon, stomach, thyroid, colorectal, bladder, lung, thyroid, oral, tongue, esophageal, pancreatic, or melanoma.

In some embodiments, the disease or condition is a viral infection.

In some embodiments, the viral infection is selected from hepatitis C (HCV), hepatitis B (HBV), Dengue virus (DENY), West Nile virus (WNV), Epstein-Barr virus (EBV), or yellow fever.

In one aspect, described herein is a pharmaceutical composition comprising a pharmaceutically acceptable diluent, excipient or binder, and a compound of Formula (I), or a pharmaceutically acceptable salt, or solvate thereof:

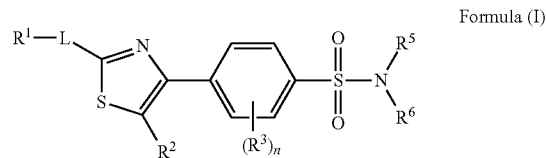

Formula (I)

wherein:
R$^1$ is C$_1$-C$_8$alkyl, substituted or unsubstituted C$_1$-C$_8$haloalkyl, substituted or unsubstituted C$_3$-C$_8$cycloalkyl, substituted or unsubstituted C$_2$-C$_8$heterocycloalkyl, substituted or unsubstituted aryl, substituted or unsubstituted heteroaryl, substituted or unsubstituted —C$_1$-C$_2$alkylene(aryl), or substituted or unsubstituted —C$_1$-C$_2$alkylene(heteroaryl);

L is absent, C$_1$-C$_4$alkylene, —N(R$^4$)—, —CH═N—NR$^4$—, —N(R$^4$)C(═O)—, or —C(═O)N(R$^4$)—, —C(═O)N(R$^4$)(C$_1$-C$_4$alkylene)-, —N(R$^4$)C(═O)(C$_1$-C$_4$alkylene)-, —(C$_1$-C$_4$alkylene)C(═O) N(R$^4$)—, —(C$_1$-C$_4$alkylene)N(R$^4$)C(═O)—, —C(═O)N(R$^4$) (C$_1$-C$_4$alkylene)O—, —N(R$^4$)C(═O)(C$_1$-C$_4$alkylene) O—, —O(C$_1$-C$_4$alkylene)C(═O)N(R$^4$)—, or —O(C$_1$-C$_4$alkylene) N(R$^4$)C(═O)—;

R$^2$ is hydrogen, halogen, —CN, —OH, substituted or unsubstituted C$_1$-C$_6$alkyl, substituted or unsubstituted C$_1$-C$_6$haloalkyl, substituted or unsubstituted C$_1$-C$_6$alkoxy, or substituted or unsubstituted C$_1$-C$_6$haloalkoxy;

each R$^3$ is independently selected from the group consisting of hydrogen, halogen, —CN, —OH, substituted or unsubstituted C$_1$-C$_6$alkyl, substituted or unsubstituted C$_1$-C$_6$haloalkyl, substituted or unsubstituted C$_1$-C$_6$alkoxy, and substituted or unsubstituted C$_1$-C$_6$haloalkoxy;

n is 0, 1, 2, 3, or 4;

R$^4$ is hydrogen, C$_1$-C$_6$alkyl, C$_1$-C$_6$haloalkyl, C$_3$-C$_8$cycloalkyl, or substituted or unsubstituted aryl;

R$^5$ and R$^6$ are each independently selected from the group consisting of hydrogen, substituted or unsubstituted C$_1$-C$_6$alkyl, substituted or unsubstituted C$_1$-C$_6$haloalkyl, substituted or unsubstituted C$_3$-C$_8$cycloalkyl, substituted or unsubstituted C$_2$-C$_8$heterocycloalkyl, substituted or unsubstituted aryl, substituted or unsubstituted heteroaryl, substituted or unsubstituted —C$_1$-C$_2$alkylene(aryl), and substituted or unsubstituted —C$_1$-C$_2$alkylene(heteroaryl);

or R$^5$ and R$^6$ are taken together with the nitrogen to which they are attached form a substituted or unsubstituted 4-, 5-, 6-, or 7-membered heterocycloalkyl.

In some embodiments, R² is hydrogen; R³ is hydrogen; and n is 0.

In some embodiments, the compound of Formula (I) has the structure of Formula (Ia):

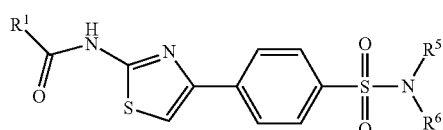

Formula (Ia)

In some embodiments, the compound of Formula (I) has the structure of Formula (Ib), Formula (Ic), or Formula (Id):

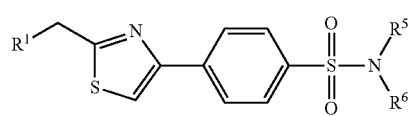

Formula (Ib)

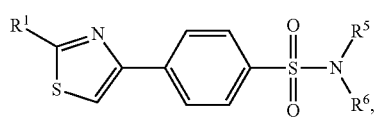

Formula (Ic)

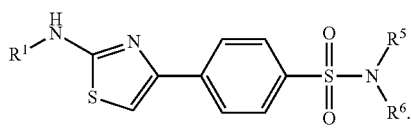

Formula (Id)

In some embodiments, R¹ is substituted or unsubstituted $C_1$-$C_8$alkyl.

In some embodiments, R¹ is selected from the group consisting of methyl, ethyl, n-propyl, i-propyl, n-butyl, sec-butyl, i-butyl, t-butyl, 1-ethyl-propyl, n-pentyl, n-hexyl, and n-heptyl.

In some embodiments, R¹ is 1-ethyl-propyl or sec-butyl.

In some embodiments, R¹ is substituted or unsubstituted aryl.

In some embodiments, R¹ is phenyl optionally substituted with halogen, —CN, —OH, $C_1$-$C_6$ alkyl, $C_1$-$C_6$haloalkyl, $C_1$-$C_6$alkoxy, or $C_1$-$C_6$haloalkoxy.

In some embodiments, R¹ is substituted or unsubstituted $C_3$-$C_8$cycloalkyl.

In some embodiments, R¹ is selected from the group consisting of cyclopropyl, cyclobutyl, cyclopentyl, and cyclohexyl.

In some embodiments, R⁵ and R⁶ are each independently substituted or unsubstituted $C_1$-$C_6$alkyl.

In some embodiments, R⁵ and R⁶ are each independently selected from methyl or ethyl.

In some embodiments, R⁵ and R⁶ are taken together with the nitrogen to which they are attached form a substituted or unsubstituted 4-, 5-, 6-, or 7-membered heterocycloalkyl.

In some embodiments, R⁵ and R⁶ are taken together with the nitrogen to which they are attached form a pyrrolidinyl, morpholinyl, piperidinyl, 4-methylpiperidinyl, 2-methylpiperidinyl, 3-methylpiperidinyl, thiomorpholinyl, piperazinyl, or 4-methylpiperazinyl.

In some embodiments, R¹ is sec-butyl; and R⁵ and R⁶ are each ethyl.

In some embodiments, the compound has one of the following structures:

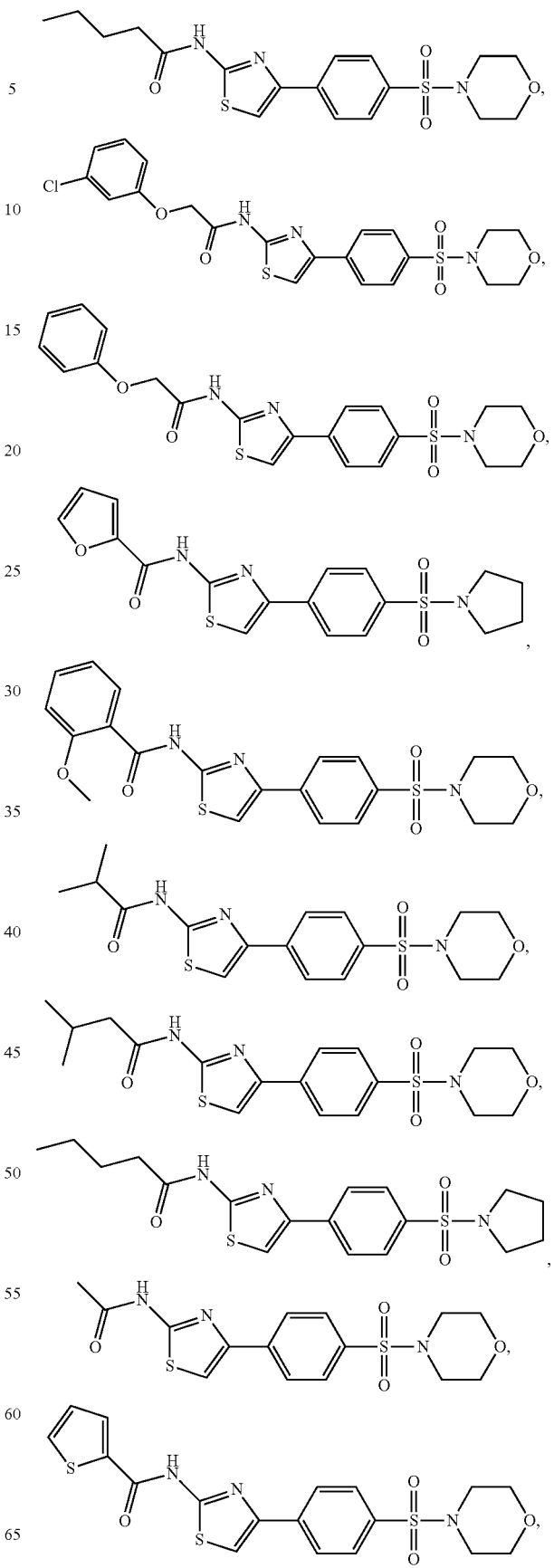

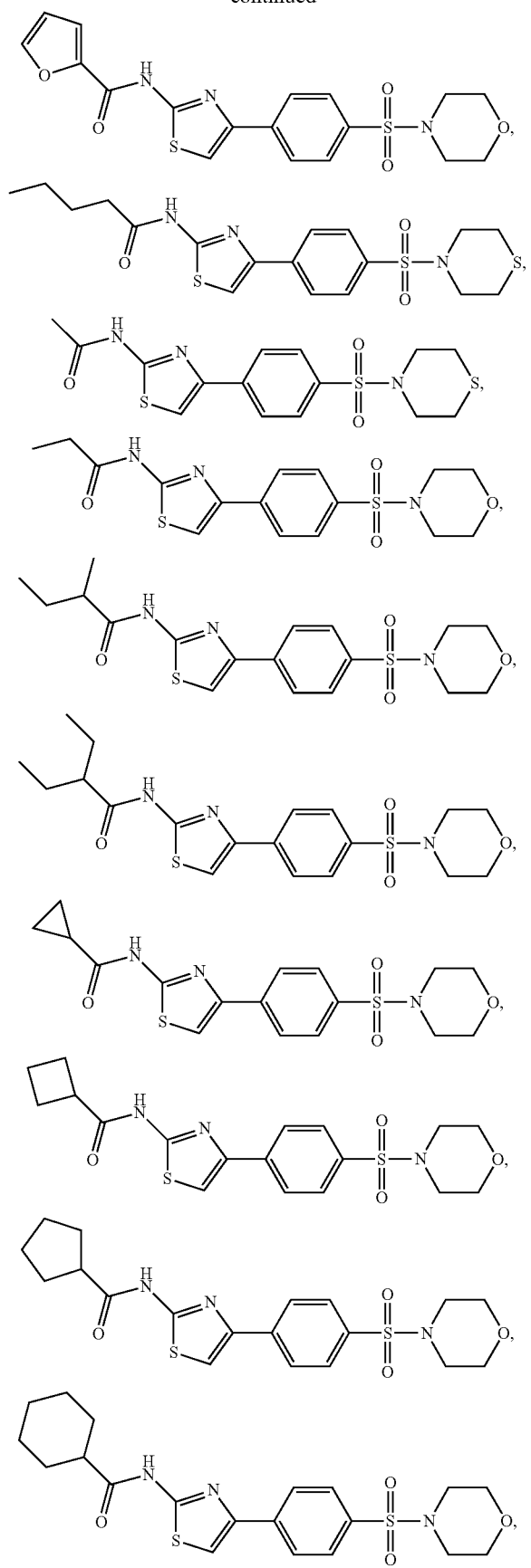
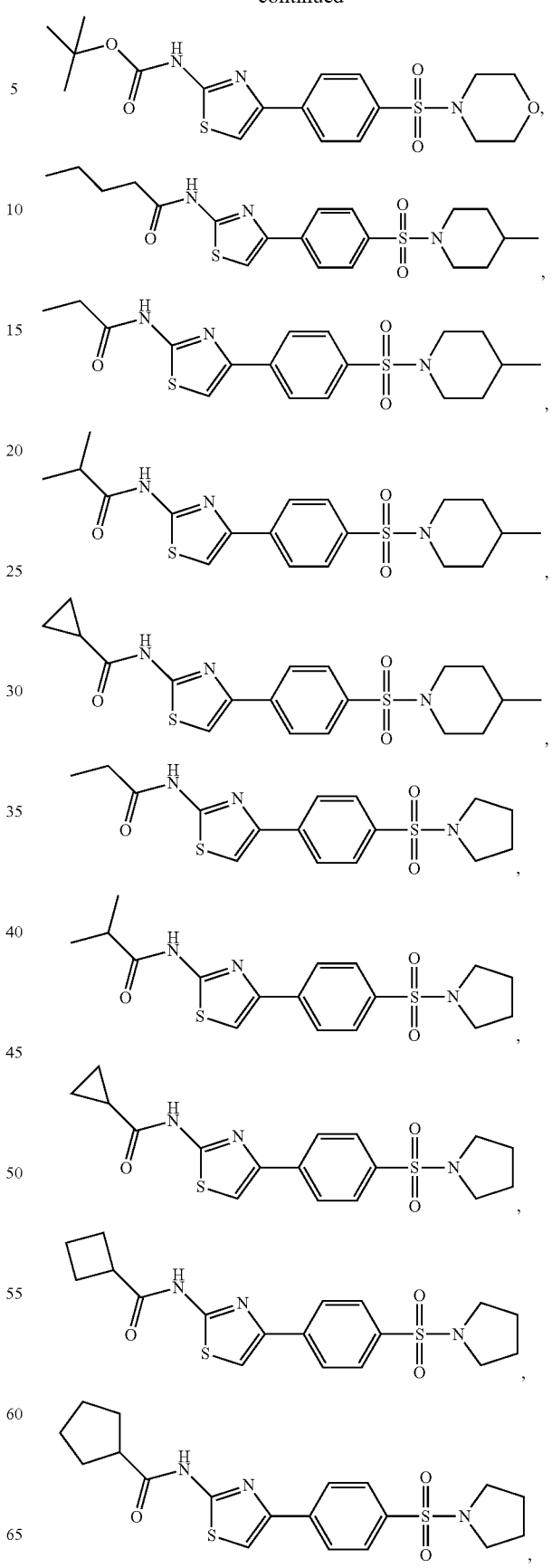

-continued
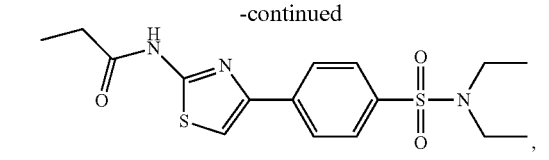
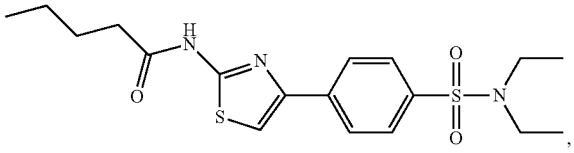
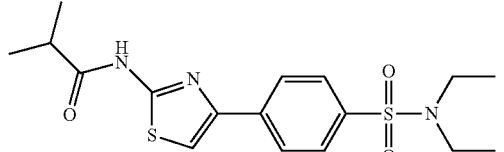
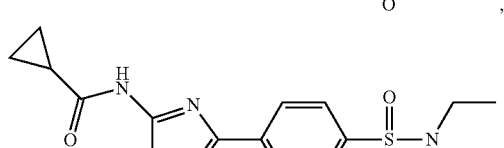
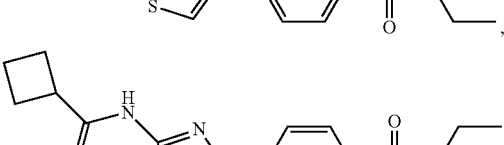
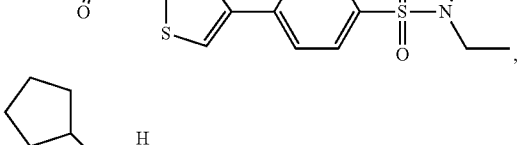
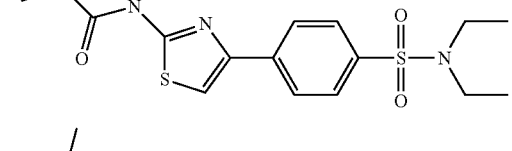
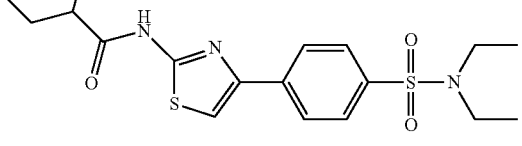
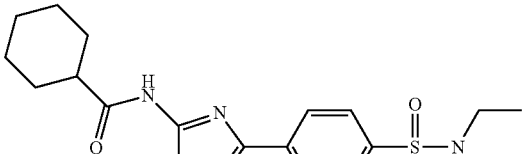
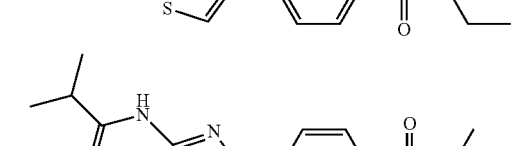
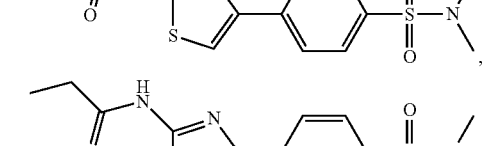
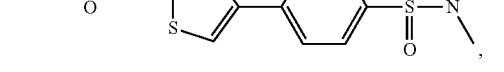
-continued
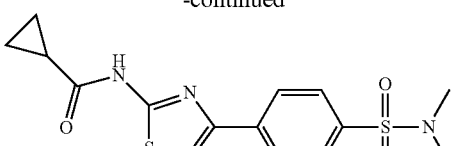
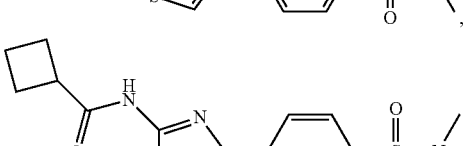
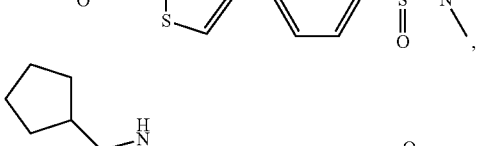
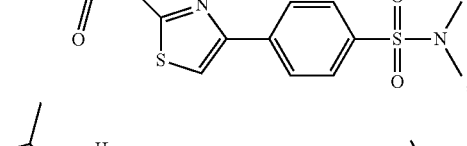
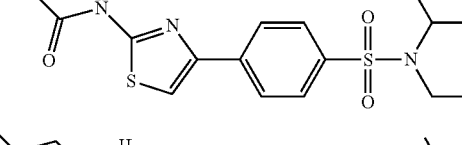
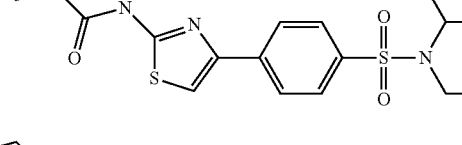
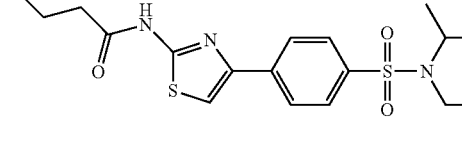
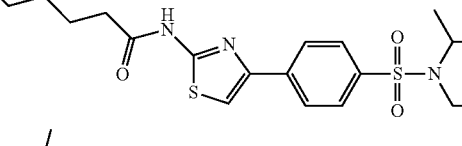
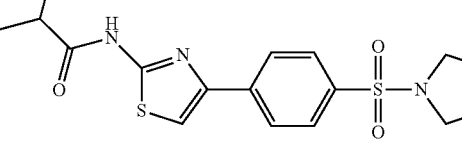
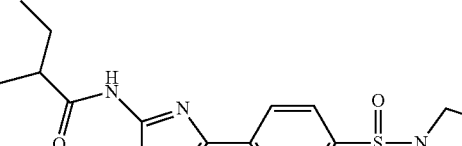
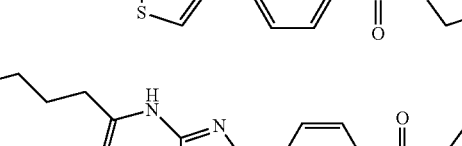
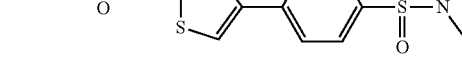

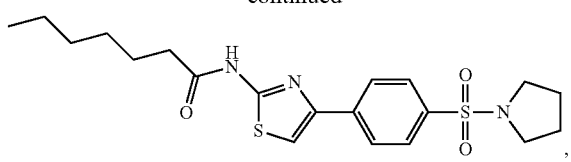
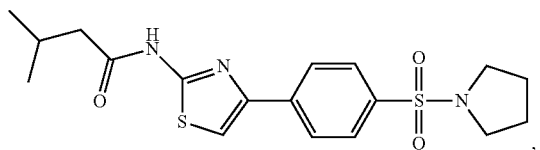
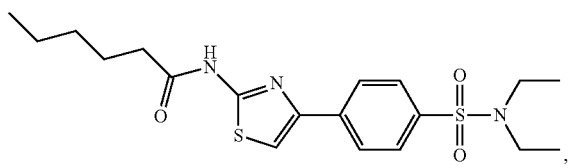
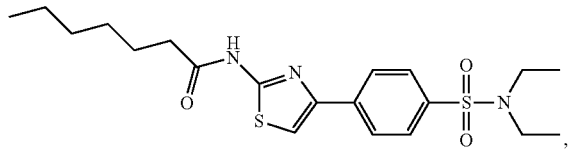
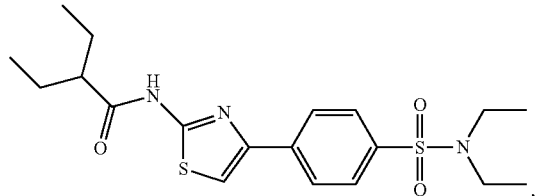
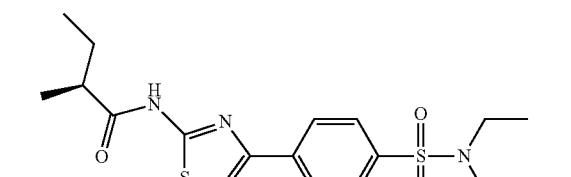
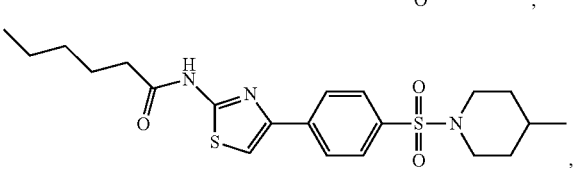
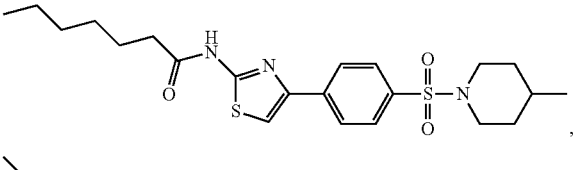
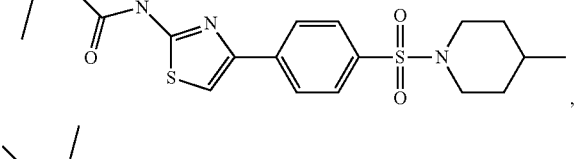
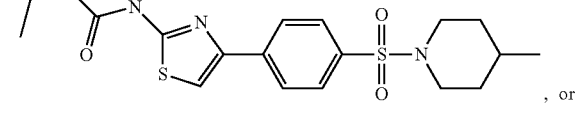, or
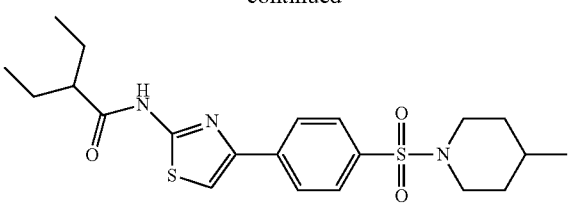
In some embodiments, the compound has one of the following structures:
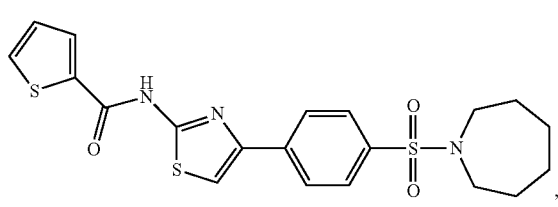
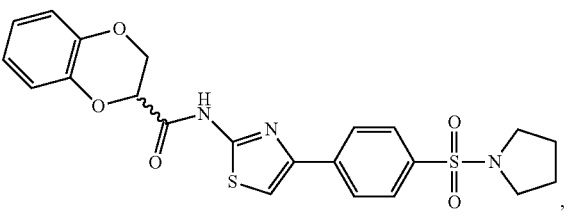
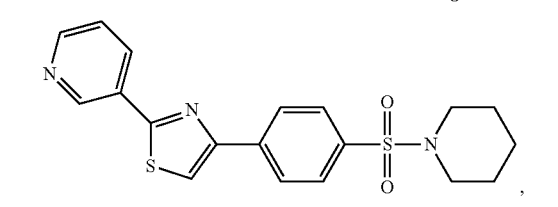
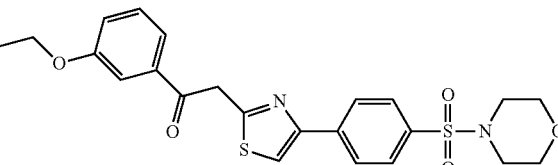
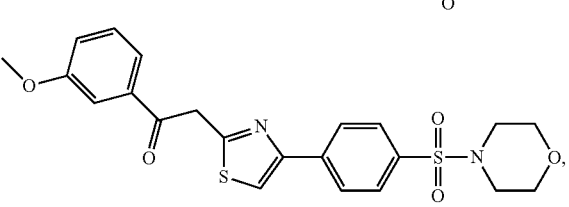
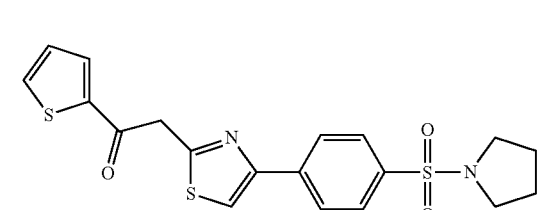
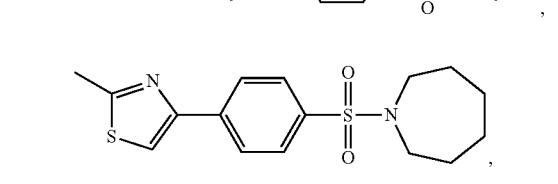

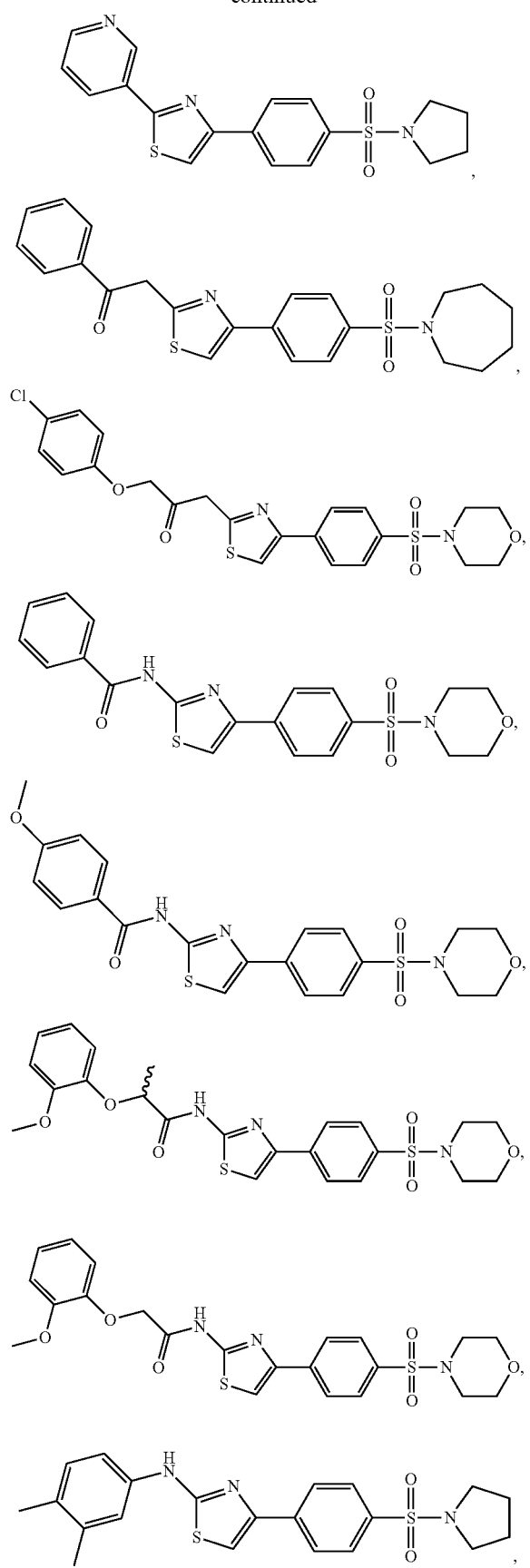
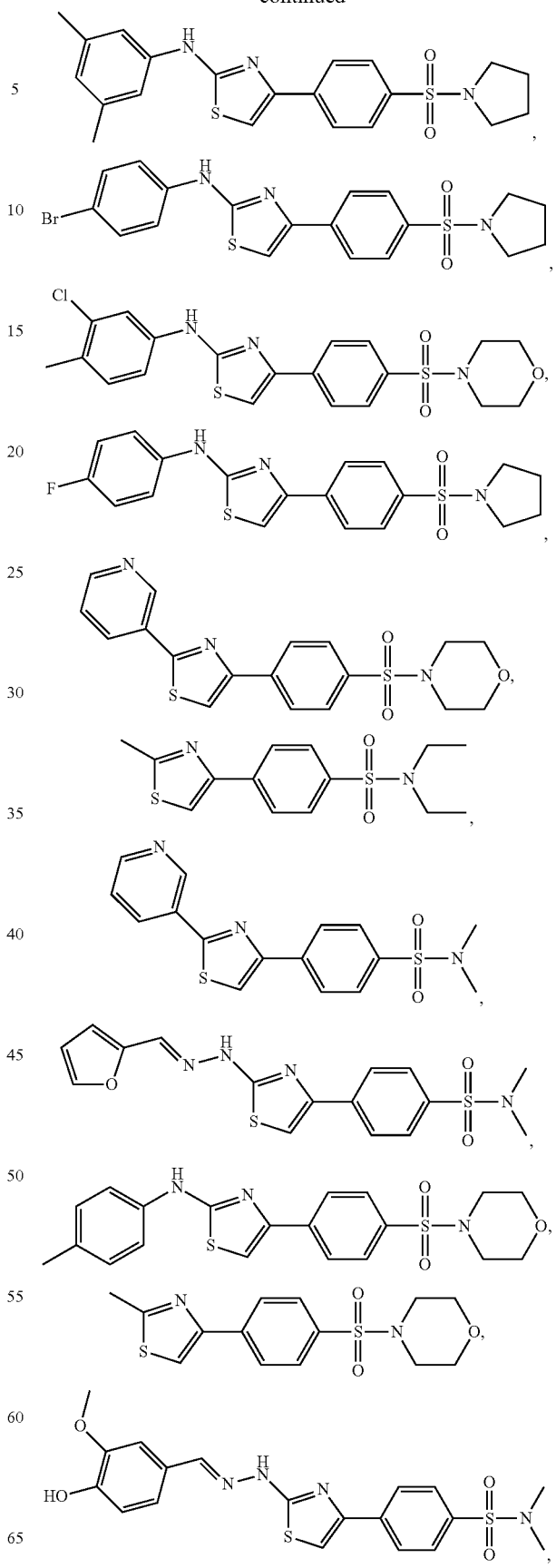

-continued
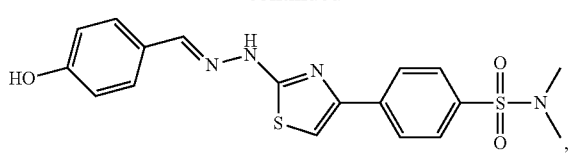
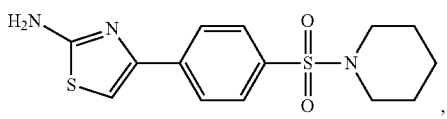
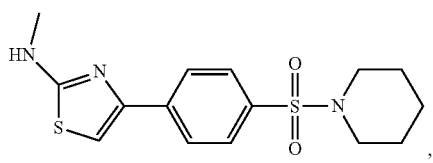
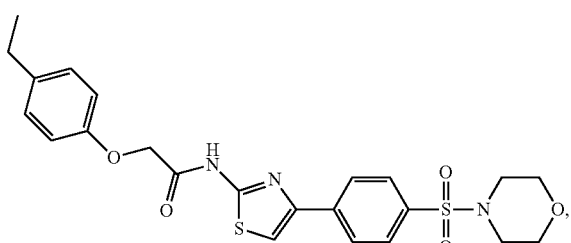
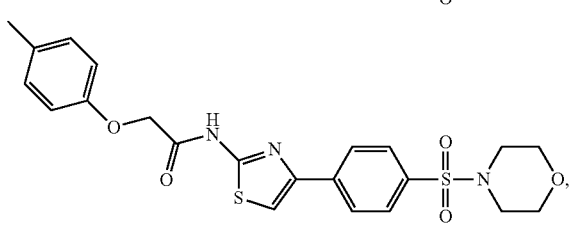
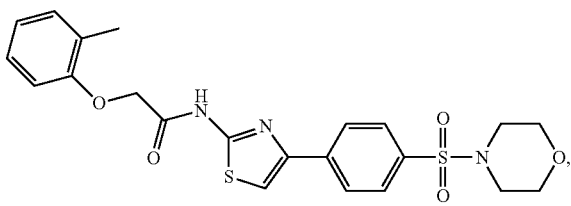
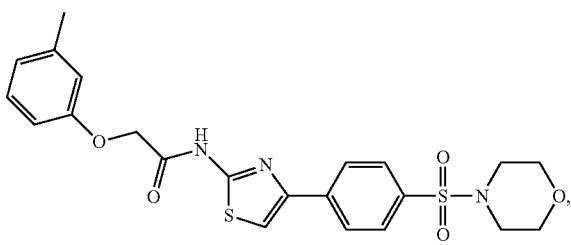
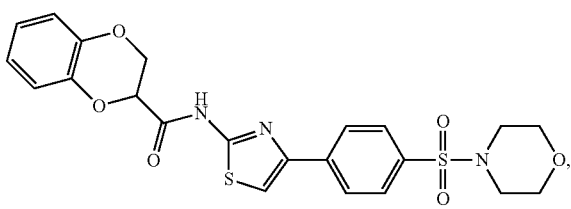
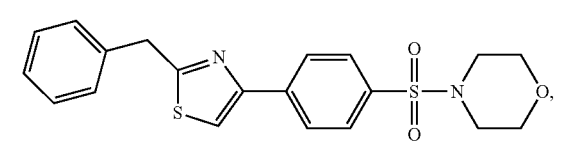
-continued
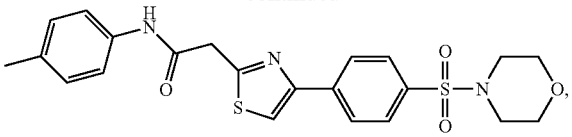
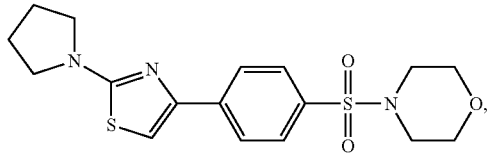
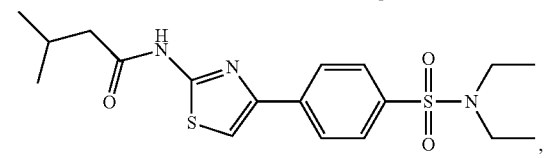
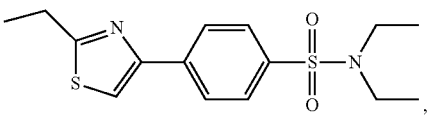
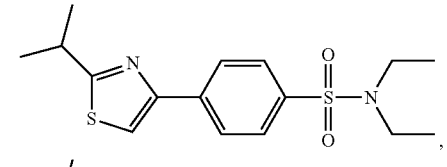
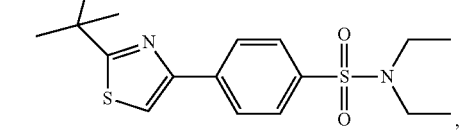
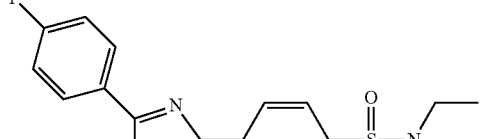
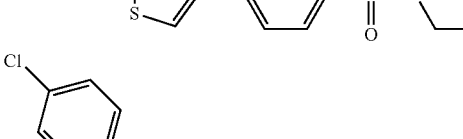
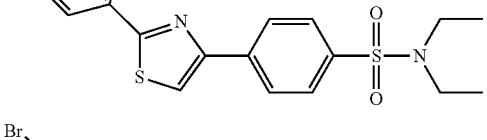
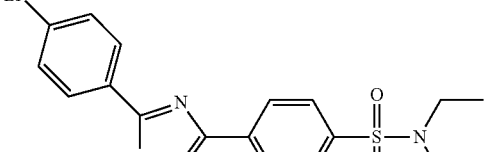
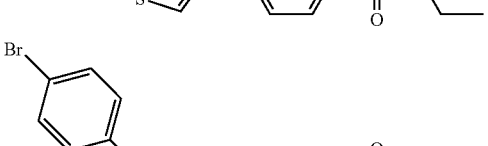
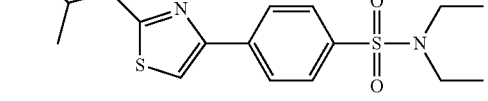

-continued

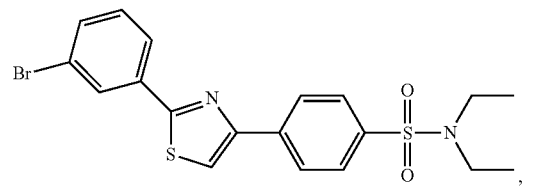,

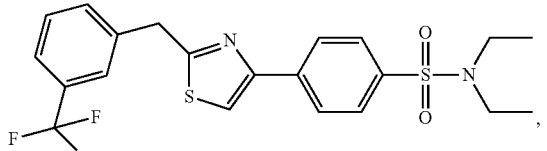,

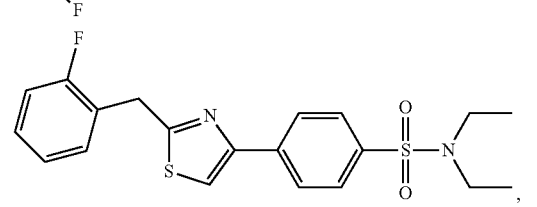,

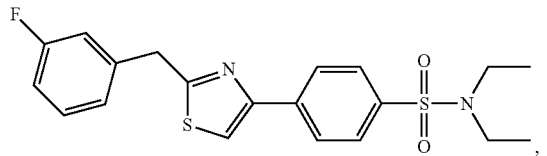,

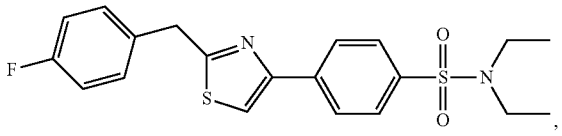,

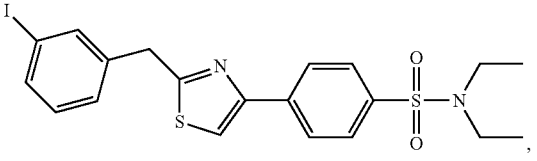,

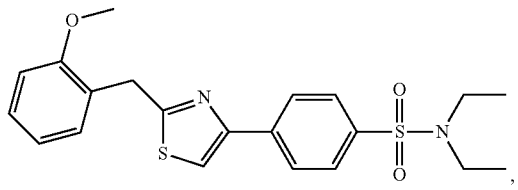,

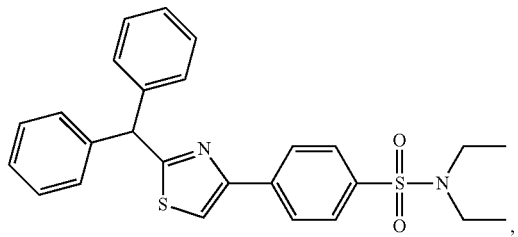,

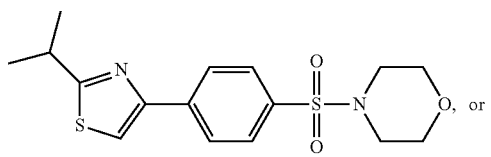, or

-continued

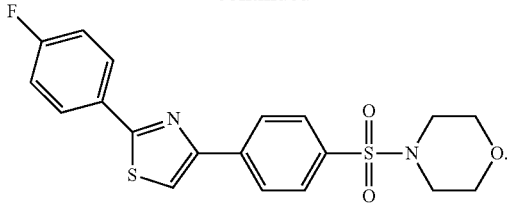.

In one aspect, described herein is a compound that has the structure of Formula (II), or a pharmaceutically acceptable salt, or solvate thereof:

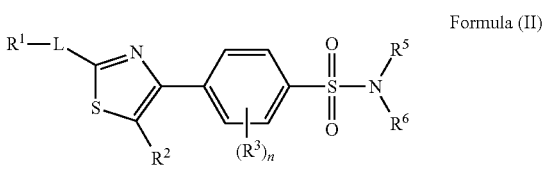

Formula (II)

wherein:
$R^1$ is substituted or unsubstituted $C_3$-$C_8$cycloalkyl;
L is absent, $C_1$-$C_4$alkylene, —N($R^4$)—, —CH=N—N($R^4$)—, —N($R^4$)C(=O)—, or —C(=O)N($R^4$)—, —C(=O)N($R^4$)($C_1$-$C_4$alkylene)-, —N($R^4$)C(=O)($C_1$-$C_4$alkylene)-, —($C_1$-$C_4$alkylene)C(=O) N($R^4$)—, —($C_1$-$C_4$alkylene)N($R^4$)C(=O)—, —C(=O)N($R^4$)($C_1$-$C_4$alkylene)O—, —N($R^4$)C(=O)($C_1$-$C_4$alkylene) O—, —O($C_1$-$C_4$alkylene)C(=O)N($R^4$)—, or —O($C_1$-$C_4$alkylene) N($R^4$)C(=O)—;
$R^2$ is hydrogen, halogen, —CN, —OH, substituted or unsubstituted $C_1$-$C_6$alkyl, substituted or unsubstituted $C_1$-$C_6$haloalkyl, substituted or unsubstituted $C_1$-$C_6$alkoxy, or substituted or unsubstituted $C_1$-$C_6$haloalkoxy;
each $R^3$ is independently selected from the group consisting of hydrogen, halogen, —CN, —OH, substituted or unsubstituted $C_1$-$C_6$alkyl, substituted or unsubstituted $C_1$-$C_6$haloalkyl, substituted or unsubstituted $C_1$-$C_6$alkoxy, and substituted or unsubstituted $C_1$-$C_6$haloalkoxy;
n is 0, 1, 2, 3, or 4;
$R^4$ is hydrogen, $C_1$-$C_6$alkyl, $C_1$-$C_6$haloalkyl, $C_3$-$C_8$cycloalkyl, or substituted or unsubstituted aryl;
$R^5$ and $R^6$ are each independently selected from the group consisting of hydrogen, substituted or unsubstituted $C_1$-$C_6$alkyl, substituted or unsubstituted $C_1$-$C_6$haloalkyl, substituted or unsubstituted $C_3$-$C_8$cycloalkyl, substituted or unsubstituted $C_2$-$C_8$heterocycloalkyl, substituted or unsubstituted aryl, substituted or unsubstituted heteroaryl, substituted or unsubstituted —$C_1$-$C_2$alkylene(aryl), and substituted or unsubstituted —$C_1$-$C_2$alkylene(heteroaryl);
or $R^5$ and $R^6$ are taken together with the nitrogen to which they are attached form a substituted or unsubstituted 4-, 5-, 6-, or 7-membered heterocycloalkyl.

In some embodiments, L is —C(=O)N($R^4$)—; $R^2$ is hydrogen; $R^3$ is hydrogen; $R^4$ is hydrogen; and n is 0.

In some embodiments, $R^1$ is cyclopropyl, cyclobutyl, cyclopentyl, or cyclohexyl.

In some embodiments, $R^5$ and $R^6$ are each independently substituted or unsubstituted $C_1$-$C_6$alkyl.

In some embodiments, $R^5$ and $R^6$ are each methyl or ethyl.

In some embodiments, $R^5$ and $R^6$ are taken together with the nitrogen to which they are attached form a substituted or unsubstituted 4-, 5-, 6-, or 7-membered heterocycloalkyl.

In some embodiments, $R^5$ and $R^6$ are taken together with the nitrogen to which they are attached form a pyrrolidinyl, morpholinyl, piperidinyl, 4-methylpiperidinyl, 2-methylpiperidinyl, 3-methylpiperidinyl, thiomorpholinyl, piperazinyl, or 4-methylpiperazinyl.

In some embodiments, the compound has one of the following structures:

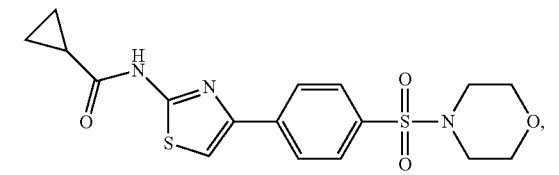

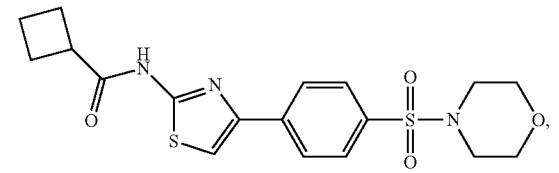

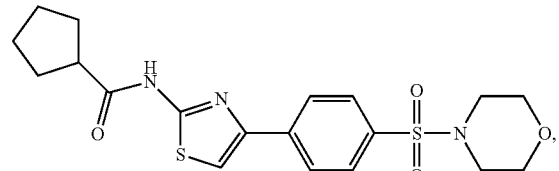

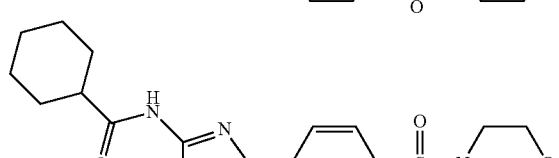

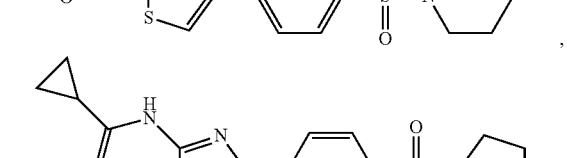

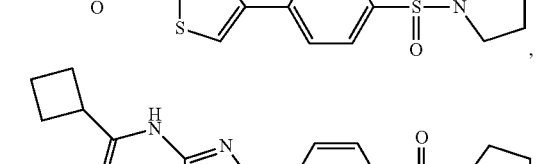

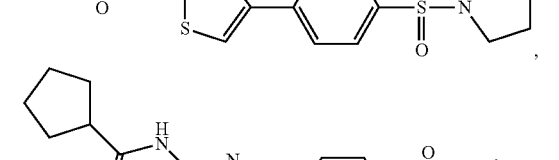

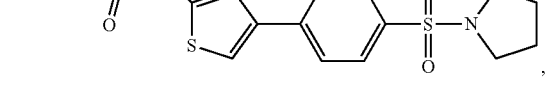

-continued

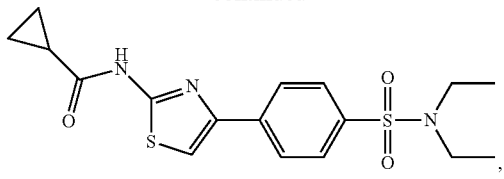

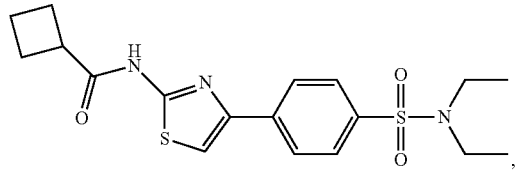

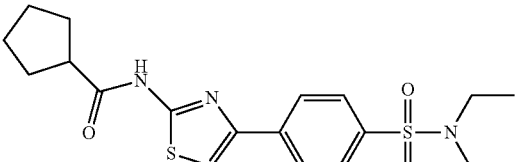

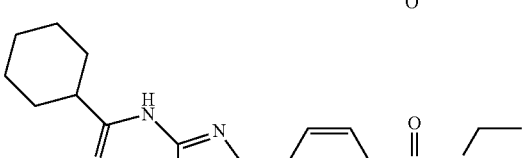

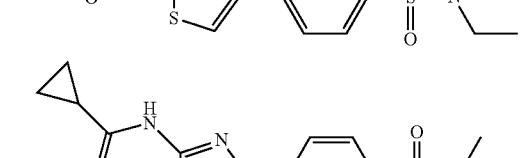

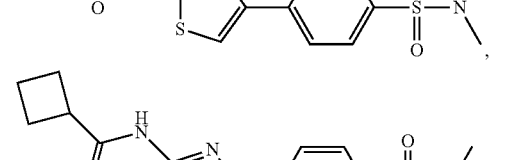

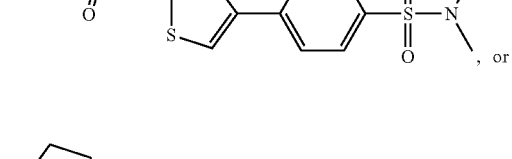, or

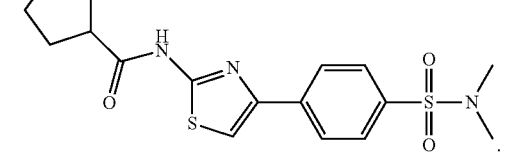.

In another aspect, described herein is a compound of formula (III):

Formula (III)

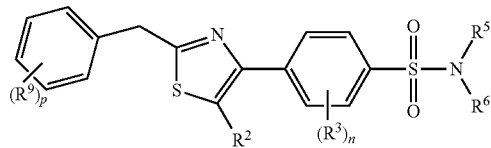

wherein:
R² is hydrogen, halogen, —CN, —OH, substituted or unsubstituted C₁-C₆alkyl, substituted or unsubstituted C₁-C₆haloalkyl, or substituted or unsubstituted C₁-C₆alkoxy;
each R³ is independently selected from the group consisting of hydrogen, halogen, —CN, —OH, substituted or unsubstituted C₁-C₆alkyl, substituted or unsubstituted C₁-C₆haloalkyl, and substituted or unsubstituted C₁-C₆alkoxy;
R⁵ and R⁶ are each independently selected from the group consisting of hydrogen, substituted or unsubstituted C₁-C₆alkyl, substituted or unsubstituted C₁-C₆haloalkyl, substituted or unsubstituted C₃-C₈cycloalkyl, substituted or unsubstituted C₂-C₈heterocycloalkyl, substituted or unsubstituted aryl, substituted or unsubstituted heteroaryl, substituted or unsubstituted —C₁-C₂alkylene(aryl), and substituted or unsubstituted —C₁-C₂alkylene(heteroaryl);
or R⁵ and R⁶ are taken together with the nitrogen to which they are attached form a substituted or unsubstituted 4-, 5-, 6-, or 7-membered heterocycloalkyl;
each R⁹ is independently selected from the group consisting of halogen, —CN, —OH, substituted or unsubstituted C₁-C₆alkyl, C₁-C₆haloalkyl, substituted or unsubstituted C₁-C₆alkoxy, and substituted or unsubstituted C₁-C₆haloalkoxy;
n is 0, 1, 2, 3, or 4; and
p is 1, 2, 3, 4, or 5;
or a pharmaceutically acceptable salt or solvate thereof.

In some embodiments, R² is hydrogen; R³ is hydrogen; and n is 0.

In some embodiments, R⁹ is halogen, C₁-C₆alkyl, C₁-C₆haloalkyl, or C₁-C₆alkoxy.

In some embodiments, R⁵ and R⁶ are each independently substituted or unsubstituted C₁-C₆alkyl.

In some embodiments, R⁵ and R⁶ are each methyl or ethyl.

In some embodiments, R⁵ and R⁶ are taken together with the nitrogen to which they are attached form a substituted or unsubstituted 4-, 5-, 6-, or 7-membered heterocycloalkyl.

In some embodiments, R⁵ and R⁶ are taken together with the nitrogen to which they are attached form a pyrrolidinyl, morpholinyl, piperidinyl, 4-methylpiperidinyl, 2-methylpiperidinyl, 3-methylpiperidinyl, thiomorpholinyl, piperazinyl, or 4-methylpiperazinyl.

In some embodiments, the compound has one of the following structures:

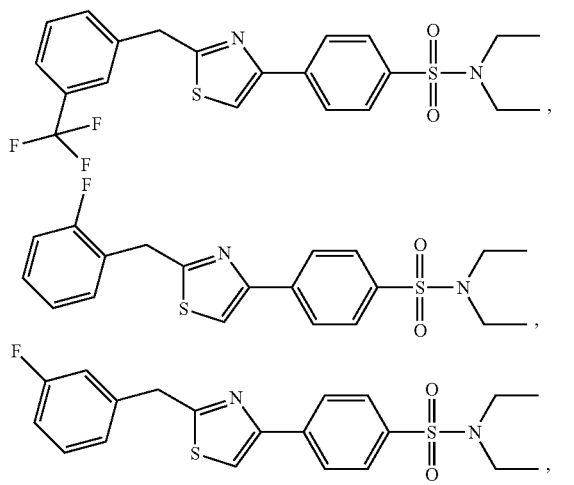

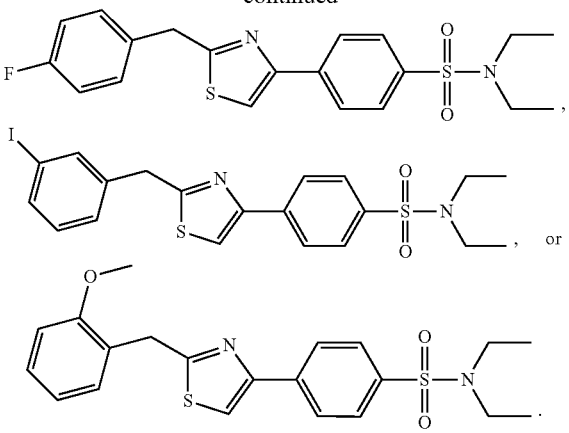

In another aspect, described herein is a compound that has the structure of Formula (IV):

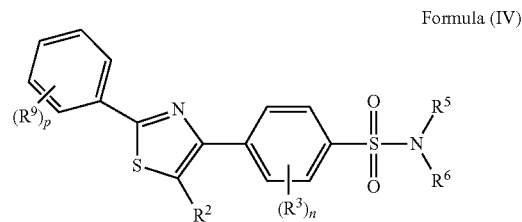

Formula (IV)

wherein:
R² is hydrogen, halogen, —CN, —OH, substituted or unsubstituted C₁-C₆alkyl, substituted or unsubstituted C₁-C₆haloalkyl, substituted or unsubstituted C₁-C₆alkoxy, or substituted or unsubstituted C₁-C₆haloalkoxy;
each R³ is independently selected from the group consisting of hydrogen, halogen, —CN, —OH, substituted or unsubstituted C₁-C₆alkyl, substituted or unsubstituted C₁-C₆haloalkyl, substituted or unsubstituted C₁-C₆alkoxy, and substituted or unsubstituted C₁-C₆haloalkoxy;
R⁵ and R⁶ are each independently selected from the group consisting of hydrogen, substituted or unsubstituted C₁-C₆alkyl, substituted or unsubstituted C₁-C₆haloalkyl, substituted or unsubstituted C₃-C₈cycloalkyl, substituted or unsubstituted C₂-C₈heterocycloalkyl, substituted or unsubstituted aryl, substituted or unsubstituted heteroaryl, substituted or unsubstituted —C₁-C₂alkylene(aryl), and substituted or unsubstituted —C₁-C₂alkylene(heteroaryl);
or R⁵ and R⁶ are taken together with the nitrogen to which they are attached form a substituted or unsubstituted 4-, 5-, 6-, or 7-membered heterocycloalkyl;
each R⁹ is independently selected from the group consisting of hydrogen, halogen, —CN, —OH, substituted or unsubstituted C₁-C₆alkyl, C₁-C₆haloalkyl, substituted or unsubstituted C₁-C₆alkoxy, and substituted or unsubstituted C₁-C₆haloalkoxy;
n is 0, 1, 2, 3, or 4; and
p is 0, 1, 2, 3, 4, or 5;
or a pharmaceutically acceptable salt, or solvate thereof.

In some embodiments, R³ is hydrogen; R⁴ is hydrogen; and n is 0.

In some embodiments, each $R^9$ is independently halogen or substituted or unsubstituted $C_1$-$C_6$alkyl; and p is 1 or 2.

In some embodiments, $R^5$ and $R^6$ are each independently substituted or unsubstituted $C_1$-$C_6$alkyl.

In some embodiments, $R^5$ and $R^6$ are each methyl or ethyl.

In some embodiments, $R^5$ and $R^6$ are taken together with the nitrogen to which they are attached form a substituted or unsubstituted 4-, 5-, 6-, or 7-membered heterocycloalkyl.

In some embodiments, $R^5$ and $R^6$ are taken together with the nitrogen to which they are attached form a pyrrolidinyl, morpholinyl, piperidinyl, 4-methylpiperidinyl, 2-methylpiperidinyl, 3-methylpiperidinyl, thiomorpholinyl, piperazinyl, or 4-methylpiperazinyl.

In some embodiments, the compound has one of the following structures:

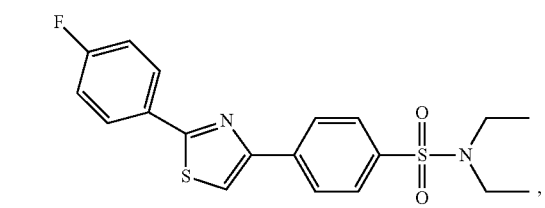

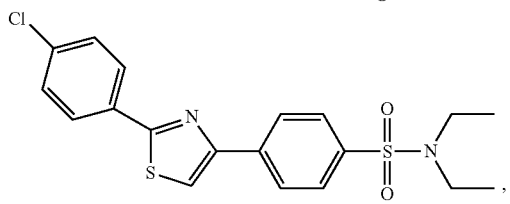

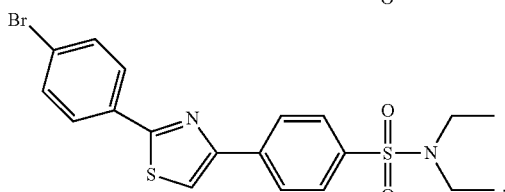

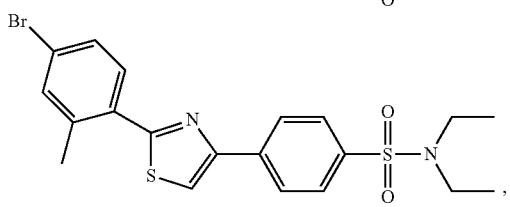

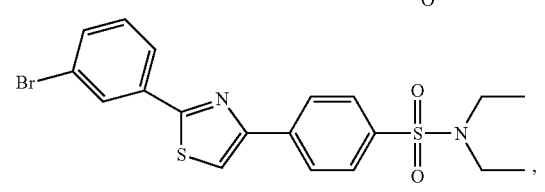

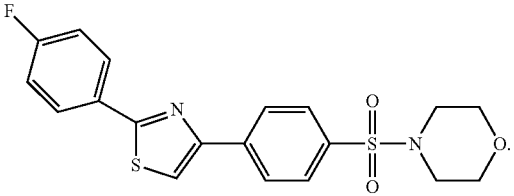

In yet another aspect, described herein is a compound that has the structure of Formula (V):

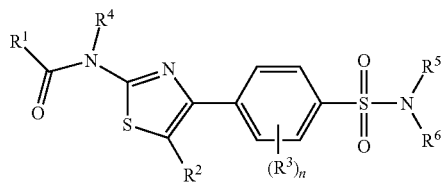

Formula (V)

wherein:
$R^1$ is substituted or unsubstituted $C_1$-$C_8$alkyl, substituted or unsubstituted $C_1$-$C_8$haloalkyl, substituted or unsubstituted $C_3$-$C_8$cycloalkyl, substituted or unsubstituted $C_2$-$C_8$heterocycloalkyl, substituted or unsubstituted aryl, substituted or unsubstituted heteroaryl, substituted or unsubstituted —$C_1$-$C_2$alkylene(aryl), or substituted or unsubstituted —$C_1$-$C_2$alkylene(heteroaryl);
$R^2$ is hydrogen, halogen, —CN, —OH, substituted or unsubstituted $C_1$-$C_6$alkyl, substituted or unsubstituted $C_1$-$C_6$haloalkyl, substituted or unsubstituted $C_1$-$C_6$alkoxy, or substituted or unsubstituted $C_1$-$C_6$haloalkoxy;
each $R^3$ is independently selected from the group consisting of hydrogen, halogen, —CN, —OH, substituted or unsubstituted $C_1$-$C_6$alkyl, substituted or unsubstituted $C_1$-$C_6$haloalkyl, substituted or unsubstituted $C_1$-$C_6$alkoxy, and substituted or unsubstituted $C_1$-$C_6$haloalkoxy;
$R^4$ is hydrogen, $C_1$-$C_6$alkyl, $C_1$-$C_6$haloalkyl, $C_3$-$C_8$cycloalkyl, or substituted or unsubstituted aryl;
$R^5$ and $R^6$ are each independently selected from the group consisting of methyl or ethyl;
or $R^5$ and $R^6$ are taken together with the nitrogen to which they are attached form a piperidinyl, 4-methylpiperidinyl, 2-methylpiperidinyl, 3-methylpiperidinyl, piperazinyl, or 4-methylpiperazinyl; and
n is 0, 1, 2, 3, or 4;
or a pharmaceutically acceptable salt or solvate thereof.

In some embodiments, $R^2$ is hydrogen; $R^3$ is hydrogen; $R^4$ is hydrogen; and n is 0.

In some embodiments, $R^1$ is substituted or unsubstituted $C_1$-$C_8$alkyl.

In some embodiments, $R^1$ is methyl, ethyl, n-propyl, i-propyl, n-butyl, sec-butyl, i-butyl, t-butyl, 1-ethyl-propyl, n-pentyl, n-hexyl, or n-heptyl.

In some embodiments, $R^1$ is 1-ethyl-propyl or sec-butyl.

In some embodiments, $R^5$ and $R^6$ are each methyl or ethyl.

In some embodiments, $R^5$ and $R^6$ are taken together with the nitrogen to which they are attached form a 4-methylpiperidinyl or 2-methylpiperidinyl.

In some embodiments, the compound has one of the following structures:

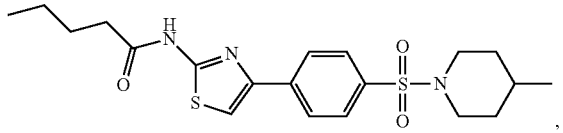

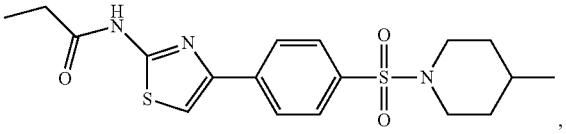

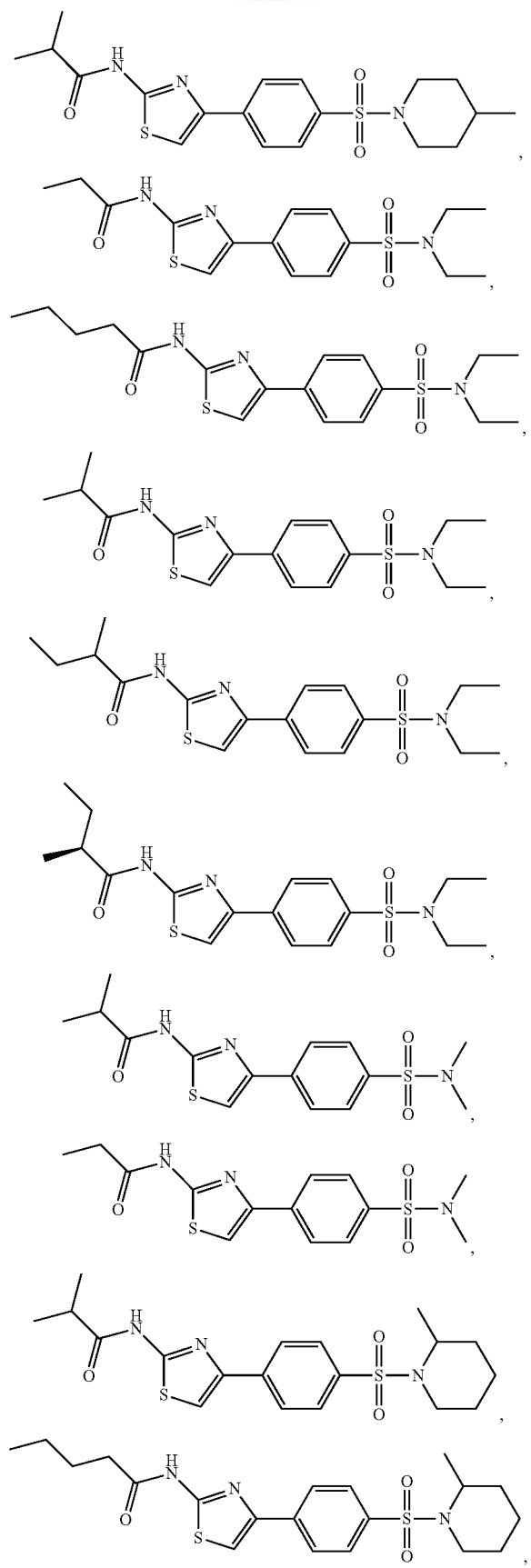
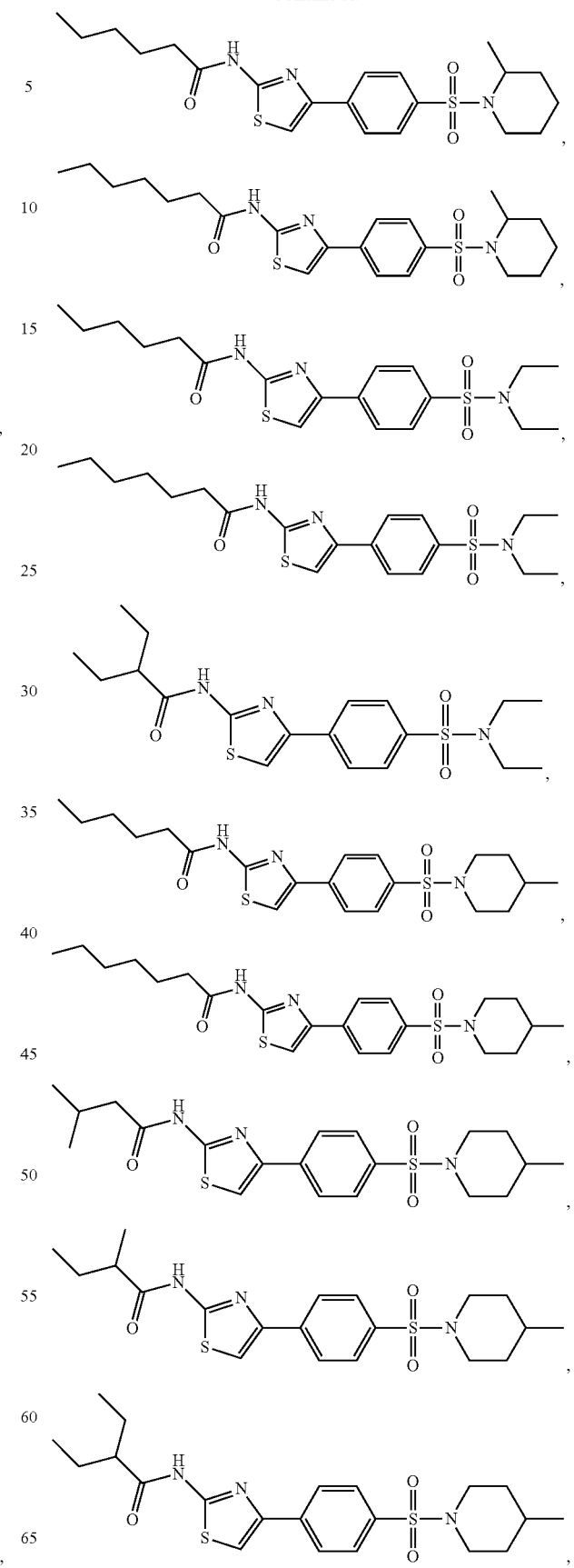

-continued

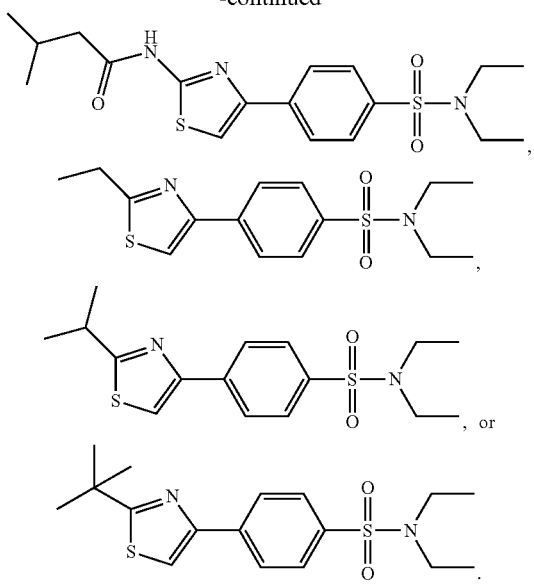

In another aspect, described herein is a compound or a pharmaceutically acceptable salt or solvate thereof selected that has one of the following structures:

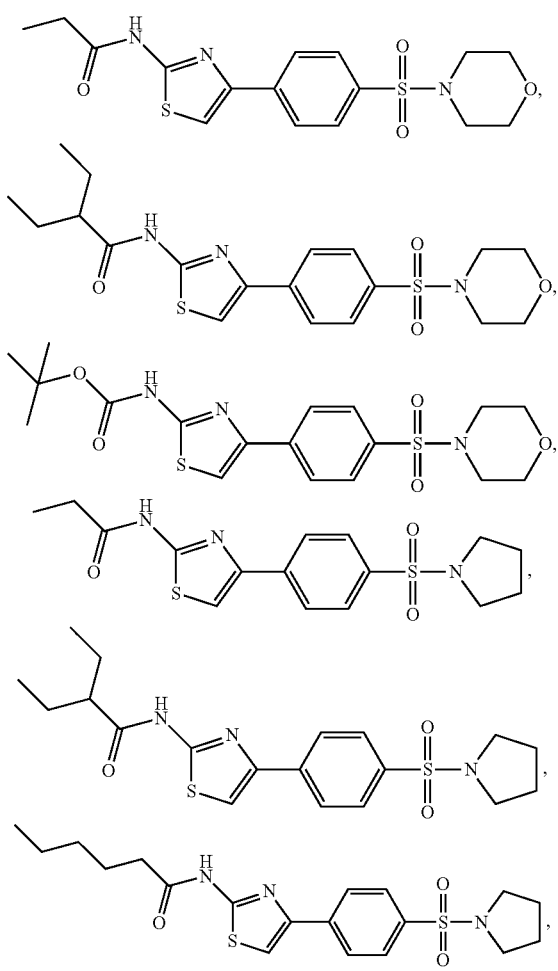

-continued

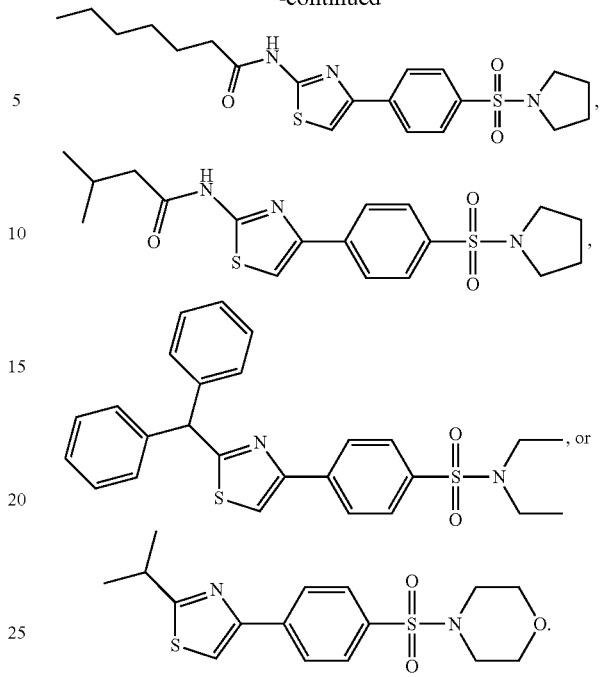

Any combination of the groups described above or below for the various variables is contemplated herein.

In one aspect, provided herein is a pharmaceutical composition comprising a compound of Formula (I), Formula (Ia), Formula (Ib), Formula (Ic), Formula (Id), Formula (II), Formula (III), Formula (IV), or Formula (V), or a pharmaceutically acceptable salt thereof, and a pharmaceutically acceptable excipient.

In some embodiments, the compound of Formula (I), Formula (Ia), Formula (Ib), Formula (Ic), Formula (Id), Formula (II), Formula (III), Formula (IV), or Formula (V), or a pharmaceutically acceptable salt thereof, is formulated for intravenous injection, subcutaneous injection, oral administration, inhalation, nasal administration, topical administration, ophthalmic administration or otic administration. In some embodiments, the compound of Formula (I), Formula (Ia), Formula (Ib), Formula (Ic), Formula (Id), Formula (II), Formula (III), Formula (IV), or Formula (V), or a pharmaceutically acceptable salt thereof, is formulated as (i.e. incorporated into) a tablet, a pill, a capsule, a liquid, an inhalant, a nasal spray solution, a suppository, a suspension, a gel, a solution, an ointment, a lotion, an eye drop or an ear drop.

In another aspect, described herein is a method of treating a disease or condition by inhibition of Fatty Acid Synthase (FASN) in a subject in need thereof, which method comprises administering to the subject a therapeutically effective amount of a compound of Formula (I), Formula (Ia), Formula (Ib), Formula (Ic), Formula (Id), Formula (II), Formula (III), Formula (IV), or Formula (V), or a pharmaceutically acceptable salt thereof. In another aspect, described herein is a method of treating a disease or condition in a subject by inhibition of Fatty Acid Synthase (FASN), which method comprises administering to the subject a pharmaceutical composition comprising a compound of Formula (I), Formula (Ia), Formula (Ib), Formula (Ic), Formula (Id), Formula (II), Formula (III), Formula (IV), or Formula (V), or a pharmaceutically acceptable salt thereof. In some embodiments, the disease or condition is cancer. In some embodiments, the disease or condition is a microbial infection. In some embodiments, the disease or condition is a viral infection. In some embodiments the disease or condition is diabetes. In some embodiments the disease or condition is obesity.

In another aspect, described herein is a method of treating a disease or condition by inhibition of the thioesterase domain of Fatty Acid Synthase (FASN-TE) in a subject in need thereof, which method comprises administering to the subject a therapeutically effective amount of a compound of Formula (I), Formula (Ia), Formula (Ib), Formula (Ic), Formula (Id), Formula (II), Formula (III), Formula (IV), or Formula (V), or a pharmaceutically acceptable salt thereof. In another aspect, described herein is a method of treating a disease or condition in a subject by inhibition of the thioesterase domain of Fatty Acid Synthase (FASN-TE), which method comprises administering to the subject a pharmaceutical composition comprising a compound of Formula (I), Formula (Ia), Formula (Ib), Formula (Ic), Formula (Id), Formula (II), Formula (III), Formula (IV), or Formula (V), or a pharmaceutically acceptable salt thereof. In some embodiments, the disease or condition is cancer. In some embodiments, the disease or condition is a microbial infection. In some embodiments, the disease or condition is a viral infection. In some embodiments the disease or condition is diabetes. In some embodiments the disease or condition is obesity.

In any of the aforementioned aspects are further embodiments in which: (a) the effective amount of the compound of Formula (I), Formula (Ia), Formula (Ib), Formula (Ic), Formula (Id), Formula (II), Formula (III), Formula (IV), or Formula (V), is systemically administered to the mammal; and/or (b) the effective amount of the compound is administered orally to the mammal; and/or (c) the effective amount of the compound is intravenously administered to the mammal; and/or (d) the effective amount of the compound is administered by inhalation; and/or (e) the effective amount of the compound is administered by nasal administration; or and/or (f) the effective amount of the compound is administered by injection to the mammal; and/or (g) the effective amount of the compound is administered topically to the mammal; and/or (h) the effective amount of the compound is administered by ophthalmic administration; and/or (i) the effective amount of the compound is administered rectally to the mammal; and/or (j) the effective amount is adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In any of the aforementioned aspects involving the administration of a compound of Formula (I), Formula (Ia), Formula (Ib), Formula (Ic), Formula (Id), Formula (II), Formula (III), Formula (IV), or Formula (V), or a pharmaceutically acceptable salt thereof, to a subject are further embodiments comprising administering at least one additional agent in addition to the administration of a compound having the structure of Formula (I), Formula (Ia), Formula (Ib), Formula (Ic), Formula (Id), Formula (II), Formula (III), Formula (IV), or Formula (V), or a pharmaceutically acceptable salt thereof. In various embodiments, the compound of Formula (I), Formula (Ia), Formula (Ib), Formula (Ic), Formula (Id), Formula (II), Formula (III), Formula (IV), or Formula (V) and the additional agent are administered in any order, including simultaneously. In some embodiments, the compound of Formula (I), Formula (Ia), Formula (Ib), Formula (Ic), Formula (Id), Formula (II), Formula (III), Formula (IV), or Formula (V) and the additional agent are administered to the subject in the same pharmaceutical composition or in separate pharmaceutical compositions.

In any of the embodiments disclosed herein, the subject is a human.

In some embodiments, compounds and compositions provided herein are administered to a human.

In some embodiments, compounds and compositions provided herein are orally administered.

In other embodiments, compounds provided herein are used for the formulation of a medicament for the inhibition of FASN.

In other embodiments, compounds provided herein are used for the formulation of a medicament for the inhibition of FASN-TE.

Articles of manufacture, which include packaging material, a compound of Formula (I), Formula (Ia), Formula (Ib), Formula (Ic), Formula (Id), Formula (II), Formula (III), Formula (IV), or Formula (V), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for the treatment of diseases or conditions that would benefit from inhibition of FASN, are provided.

Articles of manufacture, which include packaging material, a compound of Formula (I), Formula (Ia), Formula (Ib), Formula (Ic), Formula (Id), Formula (II), Formula (III), Formula (IV), or Formula (V), or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for the treatment of diseases or conditions that would benefit from inhibition of FASN-TE, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

INCORPORATION BY REFERENCE

All publications and patent applications mentioned in this specification are herein incorporated by reference to the same extent as if each individual publication or patent application was specifically and individually indicated to be incorporated by reference.

DETAILED DESCRIPTION OF THE INVENTION

Figure 1:
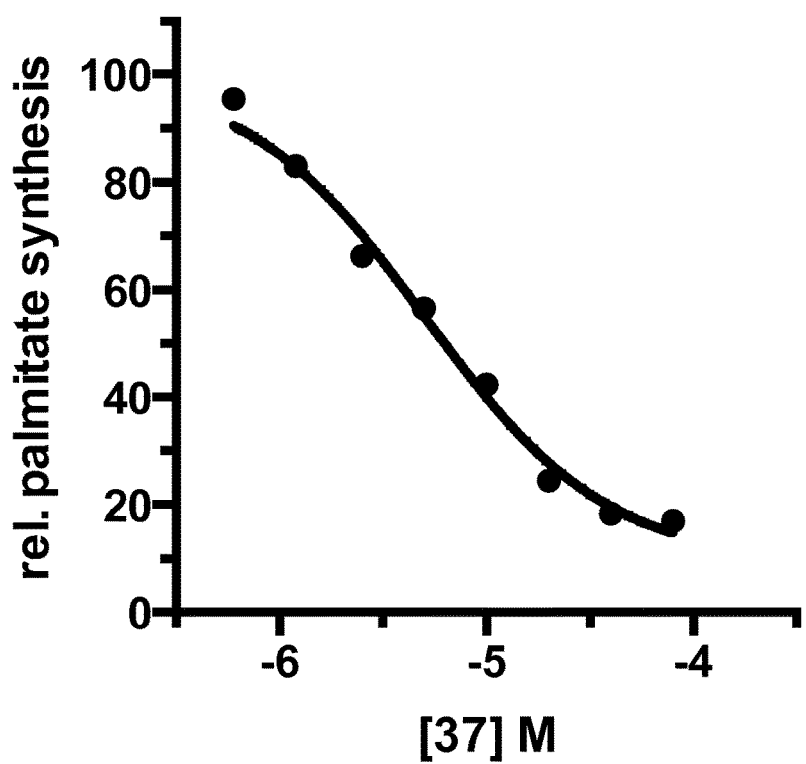
FIG. 1 shows a dose response curve of palmitate synthesis inhibition by compound 37 in UACC-903.

Fatty acids (FA) have a critical role in various cellular processes, serving as building blocks for membrane synthesis, anchors for targeting membrane proteins, precursors to lipid second messengers and a medium to store energy. Fatty acids can be obtained directly from the diet or synthesized from carbohydrate precursor by Fatty acid synthase (FASN). It is a key enzyme for the synthesis of long-chain fatty acids from acetyl-coenzyme A (CoA) and malonyl-CoA that uses reduced nicotinamide adenine dinucleotidephosphate (NADPH) as a cofactor. FASN is minimally expressed in most normal human tissues except the liver and adipose tissue, where it is expressed at high levels. FASN is a single polypeptide chain of 2511 residues that function as a homodimer. It catalyzes six distinct chemical steps using separate catalytic domains: malonyl-acetyl CoA transferase (MAT), β-ketoacyl synthase (KS), KR, β-hydroxylacyl dehydratase (DH), enoyl reductase (ER) and thioesterase (TE).

This enzyme is the final step in fatty acid biosynthesis. The enzyme condenses acetyl CoA and malonyl CoA to produce palmitate, which is the cellular source of most fatty acids and phospholipids. FASN synthesizes palmitate while the alkyl chain is linked to the acyl carrier protein (ACP) domain of the enzyme. As the chain reaches 16 carbons it is released by an intrinsic thioesterase (TE), a member of the larger class of serine hydrolase enzymes.

Fatty Acid Synthase-Thioesterase Domain (FASN-TE)

The FASN protein contains six enzymatic domains and an acyl-carrier protein (ACP). The final enzymatic pocket is a thioesterase (TE), which liberates the final product (palmitate) from its link to the ACP. The thioesterase domain of FASN is an interesting target since no thioesterase (TE) has ever been targeted for drug development. Other thioesterases can be counterscreened to assess selectivity. Compounds that selectively inhibit FASN-TE can block tumor growth in vivo because FASN is up-regulated in all the major solid tumors, and in most cases its expression is indicative of poor prognosis. Knockdown of FASN with siRNA halts tumor cell proliferation and selectively induces apoptosis of tumor cells. The correlation between expression of FASN and poor prognosis strongly suggests that this enzyme is mechanistically linked to disease progression, providing a strong rationale for developing inhibitors of FASN or FASN-TE.

In one aspect, compounds described herein are used for treating a disease or condition via the inhibition of FASN in a subject in need thereof. In one aspect, compounds described herein are used for treating a disease or condition via the inhibition of the thioesterase domain of FASN (FASN-TE) in a subject in need thereof.

In some embodiments, the disease or condition treated via the inhibition of FASN is cancer. In some embodiments, the disease or condition treated via the inhibition of the thioesterase domain of FASN (FASN-TE) is cancer.

In some embodiments, the disease or condition treated via the inhibition of FASN is a microbial infection. In some embodiments, the disease or condition treated via the inhibition of the thioesterase domain of FASN (FASN-TE) is a microbial infection.

In some embodiments, the disease or condition treated via the inhibition of FASN is a viral infection. In some embodiments, the disease or condition treated via the inhibition of the thioesterase domain of FASN (FASN-TE) is a viral infection.

In some embodiments, the disease or condition treated via the inhibition of FASN is a bacterial infection. In some embodiments, the disease or condition treated via the inhibition of the thioesterase domain of FASN (FASN-TE) is a bacterial infection.

In some embodiments, the disease or condition treated via the inhibition of FASN is diabetes. In some embodiments, the disease or condition treated via the inhibition of the thioesterase domain of FASN (FASN-TE) is diabetes.

In some embodiments, the disease or condition treated via the inhibition of FASN is obesity. In some embodiments, the disease or condition treated via the inhibition of the thioesterase domain of FASN (FASN-TE) is obesity.

Illustrative Biological Activity

Cancer

Normal cells preferentially use circulating dietary fatty acids for the synthesis of new structural lipids. In contrast, high levels of FASN expression have been observed in several cancers, including breast, prostate, colon, ovary, endometrium, mesothelium, lung, thyroid, stomach and brain (reviewed by Kuhajda, F. P. et al., Cancer Res. 2006, 66, 5977-80). The widespread expression of FASN in human cancer and its association with poor prognosis suggest that fatty acid synthesis provides an advantage for tumor growth and could be a promising target for anti-tumor drug development.

The nutrient deprived core of a solid tumor undergoes pathway "rewiring" in which it becomes dependent upon key metabolic processes. Thus, targeting metabolic signaling has significant potential as a mechanism to develop novel cancer therapeutics. Fatty acid synthase (FASN) is one of the most critical enzymes involved in aberrant tumor metabolism. The link between FASN and cancer was discovered in 1994 when Kuhajda found that the OA-519 antigen, a marker for poor prognosis in breast and prostate cancer, was actually fatty acid synthase. Increased expression of FASN is a hallmark of all major cancers, including those of the prostate, breast, colon, ovaries, and liver. Furthermore, recent studies have established a clear role for FASN in malignant melanoma, the most lethal and serious form of skin cancer (Carvalho, M A. et al. Int. J. Cancer, 2008, 123(11), 2557-65 and Seguin, F. et al. British Journal of Cancer, 2012, 107(6), 977-87). Significantly, increased expression of FASN in tumors is linked with poor prognosis, whereas the lack of FASN predicts absence of disease and overall survival. The correlation between expression of FASN and poor prognosis strongly suggests that this enzyme is mechanistically linked to disease progression. This linkage is further supported by FASN siRNA knockdown studies, which demonstrate that reduction of FASN levels arrests the tumor cell cycle at G1/S and causes tumor cell apoptosis. There is therefore a strong rationale for pursuing the development of FASN inhibitors to treat cancer.

The first identified FASN inhibitor was cerulenin, a natural antibiotic product of the fungus *Cephalosporium ceruleans*. It has been reported that FASN inhibition by cerulenin leads to apoptotic cancer cell death (Menendez, J. A. et al., Proc. Nat. Acad. Sci. 2004, 101, 10715-20). However, cerulenin's instability renders it inappropriate as an in vivo anti-tumor agent. Compound C75, a synthetic derivative related to cerulenin, having higher stability, has been tested for its anti-tumor effects (Kuhajda, F. P. et al., Proc. Nat. Acad. Sci. 2000, 97, 3450-4). FASN inhibition using C75 is cytotoxic for various tumor cell lines in vitro, and also shows growth inhibitory effects on cancer cell xenografts and transgenic mice in vivo. Another FASN inhibitor with in vivo antitumor activity is the beta-lactone Orlistat (Kridel et al., Cancer Res. 2004, 64, 2070-5), an FDA-approved drug used for treating obesity.

Overcoming resistance to the induction of normal processes that lead to cell death is a significant challenge in the treatment of solid tumor malignancies. This is in large part due to the unique metabolic wiring that occurs within the nutrient deprived core of tumor cells. Understanding these aberrant metabolic processes and defining points of therapeutic intervention has attracted considerable interest recently. It is now clear that the "Warburg effect," where cells generate energy through high rates of glycolysis in the absence of oxidative phosphorylation, is only one of many changes to central carbon metabolism in tumor cells. The re-routing of carbon happens at many metabolic junctions, but the redundancy and plasticity of carbon flux through these junctions is not widely appreciated. Many metabolic enzymes are encoded by two genes, one that functions in the cytosol and another that is mitochondrial. This redundancy gives tumor cells incredible metabolic flexibility and plasticity. The impact of knockdown of metabolic enzymes on carbon flux and tumor cell viability has been studied and it is suggested that in most cases the knockdown of metabolic enzymes is rapidly overcome by tumor cells, since they simply re-route carbon through analogous or alternative pathways to achieve the same end point. However, one important enzyme that cannot be circumvented by redundancy or metabolic plasticity is fatty acid synthase (FASN) Inhibition of FASN can yield a significant boost of efficacy for common therapeutics or surmount resistance to chemotherapy or radiotherapy. For example, blockade of FASN sensitizes tumor cells to the widely used anti-cancer drugs Paclitaxel and Herceptin. Multiple review articles describe a role for FASN in tumors providing strong arguments for this metabolic enzyme as a drug target (see for example: Kridel, S J. Et al Expert Opinion on investigational drugs, 2007, 16(141), 1817-29).

While several pathologies have been linked to FASN activity, its role in malignant cutaneous melanoma might be considered to be highly significant from a therapeutic standpoint. Clinically, patients usually present with melanoma arising from mutations in B-Raf (most melanoma) or N-Ras (~9-30% of melanomas). B-Raf driven melanoma can be treated, for a short period of time, with Vemurafenib, but tumors acquire resistance to the drug and the disease continues to progress. Unfortunately there are no approved targeted molecular targeted therapies for N-Ras melanoma, so these patients are constrained to conventional therapy and have few other options. There is strong evidence from the literature that FASN is a player in all advanced melanomas. In a sample of 77 primary melanomas, 34 had high expression of FASN, and importantly, all 30 cutaneous and nodal metastases arising from this set of 77 tumors were strongly positive for FASN (Kapur, P. et al. Modern pathology: an official journal of the United States and Canadian Academy of Pathology, Inc. 2005, 18(8), 1107-12). In a separate study it was found that expression of FASN dramatically increased in metastatic and cutaneous melanoma compared to non-malignant nevi (Innocenzi D, et al. Journal of cutaneous pathology. 2003, 30(1), 23-8.). Both of the aforementioned studies indicated significant associations between expression of FASN and Breslow thickness, a measure of melanoma invasion in the skin now replaced with cancer staging determination by the American Joint Committee on Cancer (AJCC). The expression of FASN in cutaneous melanoma is also associated with poor prognosis. Other reports show that inhibition of FASN induces apoptosis in melanoma cells, and prevents metastasis in B16-F10, a murine melanoma model. Based on evidence in the literature, a FASN antagonist may be effective in melanoma regardless of the identity of the oncogenic driver.

The term "cancer" as used herein, refers to an abnormal growth of cells that tend to proliferate in an uncontrolled way and, in some cases, to metastasize (spread). Types of cancer include, but are not limited to, solid tumors, such as those of the bladder, bowel, brain, breast, endometrium, heart, kidney, lung, liver, uterus, lymphatic tissue (lymphoma), ovary, pancreas or other endocrine organ (thyroid), prostate, skin (melanoma or basal cell cancer) or hematological tumors (such as the leukemias and lymphomas) at any stage of the disease with or without metastases.

Non-limiting examples of cancers include, acute lymphoblastic leukemia, acute myeloid leukemia, adrenocortical carcinoma, anal cancer, appendix cancer, astrocytomas, atypical teratoid/rhabdoid tumor, basal cell carcinoma, bile duct cancer, bladder cancer, bone cancer (osteosarcoma and malignant fibrous histiocytoma), brain stem glioma, brain tumors, brain and spinal cord tumors, breast cancer, bronchial tumors, Burkitt lymphoma, cervical cancer, chronic lymphocytic leukemia, chronic myelogenous leukemia, colon cancer, colorectal cancer, craniopharyngioma, cutaneous T-Cell lymphoma, desmoid tumors, embryonal tumors, endometrial cancer, ependymoblastoma, ependymoma, esophageal cancer, ewing sarcoma family of tumors, eye cancer, retinoblastoma, gallbladder cancer, gastric (stomach) cancer, gastrointestinal carcinoid tumor, gastrointestinal stromal tumor (GIST), gastrointestinal stromal cell tumor, germ cell tumor, glioma, hairy cell leukemia, head and neck cancer, hepatocellular (liver) cancer, Hodgkin lymphoma, hypopharyngeal cancer, intraocular melanoma, islet cell tumors (endocrine pancreas), Kaposi sarcoma, kidney cancer, Langerhans cell histiocytosis, laryngeal cancer, leukemia, Acute lymphoblastic leukemia, acute myeloid leukemia, chronic lymphocytic leukemia, chronic myelogenous leukemia, hairy cell leukemia, liver cancer, non-small cell lung cancer, small cell lung cancer, Burkitt lymphoma, cutaneous T-cell lymphoma, Hodgkin lymphoma, non-Hodgkin lymphoma, lymphoma, Waldenstrom macroglobulinemia, medulloblastoma, medulloepithelioma, melanoma, mesothelioma, mouth cancer, chronic myelogenous leukemia, myeloid leukemia, multiple myeloma, nasopharyngeal cancer, neuroblastoma, non-Hodgkin lymphoma, non-small cell lung cancer, oral cancer, oropharyngeal cancer, osteosarcoma, malignant fibrous histiocytoma of bone, ovarian cancer, ovarian epithelial cancer, ovarian germ cell tumor, ovarian low malignant potential tumor, pancreatic cancer, papillomatosis, parathyroid cancer, penile cancer, pharyngeal cancer, pineal parenchymal tumors of intermediate differentiation, pineoblastoma and supratentorial primitive neuroectodermal tumors, pituitary tumor, plasma cell neoplasm/multiple myeloma, pleuropulmonary blastoma, primary central nervous system lymphoma, prostate cancer, rectal cancer, renal cell (kidney) cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, stomach (gastric) cancer, supratentorial primitive neuroectodermal tumors, T-cell lymphoma, testicular cancer, throat cancer, thymoma and thymic carcinoma, thyroid cancer, urethral cancer, uterine cancer, uterine sarcoma, vaginal cancer, vulvar cancer, Waldenstrom macroglobulinemia, and Wilms tumor.

In some embodiments, a compound disclosed herein, or a pharmaceutically acceptable salt or solvate thereof, is used in the treatment of ovarian cancer, prostate cancer, breast cancer, lung cancer, melanoma, head and neck cancer, bowel cancer (colorectal cancer), thyroid cancer, glioblastoma, follicular lymphoma, renal cancer, Hodgkin lymphoma, hepatocellular carcinoma, pancreatic cancer or melanoma.

In some embodiments, a compound disclosed herein, or a pharmaceutically acceptable salt thereof, is used in the treatment of bone metastases.

In some embodiments, a compound disclosed herein, or a pharmaceutically acceptable salt or solvate thereof, is used in the treatment of oral cancer, prostate cancer, rectal cancer, non-small cell lung cancer, lip and oral cavity cancer, liver cancer, lung cancer, anal cancer, kidney cancer, vulvar cancer, breast cancer, oropharyngeal cancer, nasal cavity and paranasal sinus cancer, nasopharyngeal cancer, urethra cancer, small intestine cancer, bile duct cancer, bladder cancer, ovarian cancer, laryngeal cancer, hypopharyngeal cancer, gallbladder cancer, colon cancer, colorectal cancer, head and neck cancer, parathyroid cancer, penile cancer, vaginal cancer, thyroid cancer, pancreatic cancer, esophageal cancer, Hodgkin's lymphoma, leukemia-related disorders, mycosis fungoides, or myelodysplastic syndrome.

In some embodiments, a compound disclosed herein, or a pharmaceutically acceptable salt thereof, is used in the treatment of non-small cell lung cancer, pancreatic cancer, breast cancer, ovarian cancer, colorectal cancer, or head and neck cancer.

In some embodiments, a compound disclosed herein, or a pharmaceutically acceptable salt thereof, is used in the treatment of leukemia, a carcinoma, a tumor, a neoplasm, a lymphoma, a melanoma, a glioma, a sarcoma, or a blastoma.

In some embodiments, the leukemia is Acute lymphoblastic leukemia (ALL), Acute myelogenous leukemia (AML), Chronic lymphocytic leukemia (CLL), Chronic myelogenous leukemia (CML), or Acute monocytic leukemia (AMoL).

In some embodiments, the carcinoma is selected from the group consisting of: carcinoma, adenocarcinoma, adenoid cystic carcinoma, adenosquamous carcinoma, adrenocortical carcinoma, well differentiated carcinoma, squamous cell carcinoma, basal cell carcinoma, serous carcinoma, small cell carcinoma, invasive squamous cell carcinoma, large cell carcinoma, islet cell carcinoma, oat cell carcinoma, squamous carcinoma, undifferentiatied carcinoma, verrucous carcinoma, renal cell carcinoma, papillary serous adenocarcinoma, merkel cell carcinoma, hepatocellular carcinoma, soft tissue carcinomas, bronchial gland carcinomas, capillary carcinoma, bartholin gland carcinoma, carcinosarcoma, papilloma/carcinoma, clear cell carcinoma, endometrioid adenocarcinoma, mesothelial, metastatic carcinoma, mucoepidermoid carcinoma, cholangiocarcinoma, actinic keratoses, cystadenoma, and hepatic adenomatosis.

In some embodiments, the tumor is selected from the group consisting of: astrocytic tumors, malignant mesothelial tumors, ovarian germ cell tumor, supratentorial primitive neuroectodermal tumors, Wilm's tumor, pituitary tumors, extragonadal germ cell tumor, gastrinoma, germ cell tumors, gestational trophoblastic tumor, brain tumors, pineal and supratentorial primitive neuroectodermal tumors, pituitary tumor, somatostatin-secreting tumor, endodermal sinus tumor, carcinoids, central cerebral astrocytoma, glucagonoma, hepatic adenoma, insulinoma, medulloepithelioma, plasmacytoma, vipoma, and pheochromocytoma.

In some embodiments, the neoplasm is selected from the group consisting of: intaepithelial neoplasia, multiple myeloma/plasma cell neoplasm, plasma cell neoplasm, interepithelial squamous cell neoplasia, endometrial hyperplasia, focal nodular hyperplasia, hemangioendothelioma, lymphangioleio myomatosis and malignant thymoma.

In some embodiments, the lymphoma is selected from the group consisting of: nervous system lymphoma, AIDS-related lymphoma, cutaneous T-cell lymphoma, Hodgkin's lymphoma, non-Hodgkin's lymphoma, mantle cell lymphoma, follicular lymphoma and Waldenstrom's macroglobulinemia.

In some embodiments, the melanoma is selected from the group consisting of: acral lentiginous melanoma, superficial spreading melanoma, uveal melanoma, lentigo maligna melanomas, melanoma, intraocular melanoma, adenocarcinoma nodular melanoma, and hemangioma.

In some embodiments, the sarcoma is selected from the group consisting of: adenomas, adenosarcoma, chondosarcoma, endometrial stromal sarcoma, Ewing's sarcoma, Kaposi's sarcoma, leiomyosarcoma, rhabdomyosarcoma, sarcoma, uterine sarcoma, osteosarcoma, and pseudosarcoma.

In some embodiments, the glioma is selected from the group consisting of: glioma, brain stem glioma, and hypothalamic and visual pathway glioma.

In some embodiments, the blastoma is selected from the group consisting of: pulmonary blastoma, pleuropulmonary blastoma, retinoblastoma, neuroblastoma, medulloblastoma, glioblastoma, and hemangiblastomas.

Microbial Infections

FASN has been identified as a target for treatment of microbial infections. In particular, it was reported that fatty acid synthesis or the level of fatty acid is critical in viral pathogenesis. For example, it was reported that the formation of a novel vesicular compartment (i.e., remodeled golgi apparatus), on the surface of which viral RNA replication takes place, requires fatty acid biosynthesis. (Cherry et al., PLoS Pathogens (2006) 2(10): e102).

The role of FASN has been implicated in the pathogenesis of viruses such as: human cytomegalomous virus (HCMV), influenza A, dengue virus (DENY), coxsackievirus B3 (CVB3), Epstein-Barr virus (EBV), west nile virus (WNV), human immunodeficiency virus (HIV), poliovirus, human papilloma virus (HPV), rous sarcoma virus, hepatitis B (HBV), and hepatitis C (HCV).

With regard to HCV, it was reported that an elevated level of fatty acid biosynthesis enzymes, including FASN, contributes to liver steatosis, leading to cirrhosis and hepatocellular carcinoma, upon HCV infection. (Fukusawa et al. Biol. Pharm. Bull., 2006, 29(9): 1958-1961). HCV replication was reported to be regulated by, among others, fatty acid biosynthesis. (Kapadia et al. Proc. Natl. Acad. Sci., 2005, 102(7): 2561-2566).

FASN is also highly expressed in human sebocytes, the lipid producing cells of the sebaceous glands. Acne is the most common disorder involving the sebaceous gland. The pathogenesis of acne involves lipid (over) production by the sebaceous gland and it has been reported that inhibitors of mammalian FASN inhibit the production of sebum in sebocytes (US 2005/0053631). Acne cannot occur without sebum lipids. Since fatty acid synthesis in bacteria is essential for cell survival, bacterial FASN has emerged as a potential target for antibacterial therapy. Unlike in most other prokaryotes, fatty acid synthase activity in mycobacteria is carried out by a single high-molecular-weight, multifunctional peptide chain (type I synthase) related to mammalian FASN. Mycobacterial type I FASN has been described as a potential target for antimycobacterial therapy, e.g. the treatment of tuberculosis. With one-third of the world's population being infected with the tuberculosis *bacillus*, and multidrug-resistant strains of *Mycobacterium tuberculosis* developing, there is a high medical need for novel tuberculosis therapies. (Silvana C. et al. Antimicrobial agents and Chemotherapy 51, 7 (2007) 2430-2435).

The term "infection," as used herein, refers to the invasion of a host organism's body tissues by disease-causing agents, their multiplication, and the reaction of host tissues to these organisms and the toxins they produce. Infectious diseases, also known as transmissible diseases or communicable diseases, comprise clinically evident illness (i.e., characteristic medical signs and/or symptoms of disease) resulting from the infection, presence and growth of pathogenic biological agents in an individual host organism.

In some embodiments, a compound disclosed herein, or a pharmaceutically acceptable salt or solvate thereof, is used in the treatment of a microbial infection. In some embodiments the microbial infection is a viral infection. In some embodiments the microbial infection is a bacterial infection.

In some embodiments the microbial infection is a viral infection. In some embodiments, the viral infection is caused by a rhinovirus, a picornavirus, an adenovirus, a hepadnavirus, an orthomyxovirus, a paramyxovirus, a rhabdovirus, an alphavirus, a rubivirus, a papillomavirus, an influenzavirus, a herpesvirus, a flavivirus, a coronavirus, an enterovirus, a calicivirus, a norovirus, a retrovirus, an oncovirus, or a lentivirus.

In some embodiments, the viral infection is herpes simplex, type 1, herpes simplex, type 2, varicella-zoster virus, Epstein-barr virus (EBV), human cytomegalovirus (HCMV), human herpesvirus, type 8, human papillomavirus (HPV), smallpox, hepatitis B virus (HBV), human bocavirus, parvovirus, human astrovirus, norwalk virus, coxsackievirus, hepatitis A virus (HAV), poliovirus, rhinovirus, Severe acute respiratory syndrome virus (SARS), hepatitis C virus (HCV), yellow fever virus, dengue virus (DENY), west nile virus (WNV), rubella virus, hepatitis E virus, human immunodeficiency virus (HIV), influenza virus, guanarito virus, junin virus, lassa virus, machupo virus, sabia virus, crimean-congo hemorrhagic fever virus, ebola virus, marburg virus, measles virus, mumps virus, parainfluenza virus, respiratory syncytial virus, human metapneumovirus, hendra virus, nipah virus, rabies virus, hepatitis D, rotavirus, orbivirus, coltivirus, banna virus, or tick-borne encephalitis virus.

In some embodiments, the microbial infection is a bacterial infection. In some embodiments, the bacterial infection is bacterial menengitis, otitis media, pneumonia, a skin infection, acne, an eye infection, sinusitis, an upper respiratory track infection, tuberculosis, gastritis, food poisoning, or a sexually transmitted disease.

In some embodiments, the bacterial infection is caused by *streptococcus, staphylococcus, escherichia coli, salmonella, helicobacter pylori, neisseria gonorrhoeae*, or *meningococcus*.

Obesity/Diabetes

Fatty acids are a major energy source and important constituents of membrane lipids, and they serve as cellular signaling molecules that play an important role in the etiology of metabolic disorders. Acetyl-CoA carboxylases 1 and 2 (ACC1 and ACC2) catalyze the synthesis of malonyl-CoA, the substrate for fatty acid synthesis and the regulator of fatty acid oxidation. They are highly regulated and play important roles in the energy metabolism of fatty acids in animals, including humans. The accumulation of fat in tissues, such as muscle and liver, is associated with insulin resistance throughout the whole body. FASN plays an important role in the development of hepatic steatosis and insulin resistance (Wakil et al. (2009) J. Lipid Res.; 50(Suppl): S138-S143).

In some embodiments, disclosed herein are methods of treating obesity and/or diabetes with a compound disclosed herein.

"Obesity," as used herein, refers to a medical condition in which excess body fat has accumulated to the extent that it may have an adverse effect on health, leading to increased health problems. In some embodiments, "obesity" refers to a weight increase, which is at least 5% of the total body weight. In some embodiments, disclosed herein is a method of treating postmenopausal obesity and/or visceral obesity with a compound disclosed herein.

Compounds

In one aspect, provided herein is a compound of Formula (I), or a pharmaceutically acceptable salt, solvate, thereof:

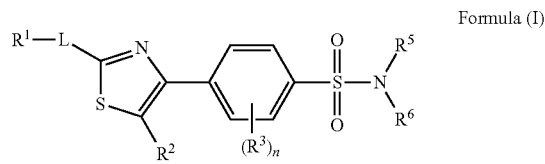

Formula (I)

wherein:
$R^1$ is $C_1$-$C_8$alkyl, substituted or unsubstituted $C_1$-$C_8$haloalkyl, substituted or unsubstituted $C_3$-$C_8$cycloalkyl, substituted or unsubstituted $C_2$-$C_8$heterocycloalkyl, substituted or unsubstituted aryl, substituted or unsubstituted heteroaryl, substituted or unsubstituted —$C_1$-$C_2$alkylene(aryl), or substituted or unsubstituted —$C_1$-$C_2$alkylene(heteroaryl);

L is absent, $C_1$-$C_4$alkylene, —N($R^4$)—, —CH═N—NR$^4$—, —N($R^4$)C(═O)—, or —C(═O)N($R^4$)—, —C(═O)N($R^4$)($C_1$-$C_4$alkylene)-, —N($R^4$)C(═O)($C_1$-$C_4$alkylene)-, —($C_1$-$C_4$alkylene)C(═O) N($R^4$)—, —($C_1$-$C_4$alkylene)N($R^4$)C(═O)—, —C(═O)N($R^4$)($C_1$-$C_4$alkylene)O—, —N($R^4$)C(═O)($C_1$-$C_4$alkylene)

O—, —O(C$_1$-C$_4$alkylene)C(=O)N(R$^4$)—, or —O(C$_1$-C$_4$alkylene) N(R$^4$)C(=O)—;

R$^2$ is hydrogen, halogen, —CN, —OH, substituted or unsubstituted C$_1$-C$_6$alkyl, substituted or unsubstituted C$_1$-C$_6$haloalkyl, substituted or unsubstituted C$_1$-C$_6$alkoxy, or substituted or unsubstituted C$_1$-C$_6$haloalkoxy;

each R$^3$ is independently selected from the group consisting of hydrogen, halogen, —CN, —OH, substituted or unsubstituted C$_1$-C$_6$alkyl, substituted or unsubstituted C$_1$-C$_6$haloalkyl, substituted or unsubstituted C$_1$-C$_6$alkoxy, and substituted or unsubstituted C$_1$-C$_6$haloalkoxy;

n is 0, 1, 2, 3, or 4;

R$^4$ is hydrogen, C$_1$-C$_6$alkyl, C$_1$-C$_6$haloalkyl, C$_3$-C$_8$cycloalkyl, or substituted or unsubstituted aryl;

R$^5$ and R$^6$ are each independently selected from the group consisting of hydrogen, substituted or unsubstituted C$_1$-C$_6$alkyl, substituted or unsubstituted C$_1$-C$_6$haloalkyl, substituted or unsubstituted C$_3$-C$_8$cycloalkyl, substituted or unsubstituted C$_2$-C$_8$heterocycloalkyl, substituted or unsubstituted aryl, substituted or unsubstituted heteroaryl, substituted or unsubstituted —C$_1$-C$_2$alkylene(aryl), and substituted or unsubstituted —C$_1$-C$_2$alkylene(heteroaryl);

or R$^5$ and R$^6$ are taken together with the nitrogen to which they are attached form a substituted or unsubstituted 4-, 5-, 6-, or 7-membered heterocycloalkyl.

Throughout the specification, groups and substituents thereof are chosen by one skilled in the field to provide stable moieties and compounds. For example, in some embodiments, R$^2$ is hydrogen, halogen, —CN, —OH, substituted or unsubstituted C$_1$-C$_6$alkyl, substituted or unsubstituted C$_1$-C$_6$haloalkyl, substituted or unsubstituted C$_1$-C$_6$alkoxy, or substituted or unsubstituted C$_1$-C$_6$haloalkoxy. In other embodiments, R$^2$ is hydrogen, halogen, —CN, C$_1$-C$_6$alkyl, or C$_1$-C$_6$haloalkyl. In some embodiments, R$^2$ is hydrogen, halogen, —CH$_3$, —CH$_2$CH$_3$, —CF$_3$, or —CH$_2$CF$_3$. In some embodiments, R$^2$ is hydrogen, halogen, —CH$_3$, or —CF$_3$. In some embodiments, R$^2$ is hydrogen.

In some embodiments, n is 0, 1, 2, 3, or 4. In some embodiments, n is 1, 2, 3, or 4. In some embodiments, n is 0, 1, 2, or 3. In some embodiments, n is 0, 1, or 2. In some embodiments, n is 0, or 1. In some embodiments, n is 0. In some embodiments, n is 1, 2, 3, or 4. In some embodiments, n is 1, 2, or 3. In some embodiments, n is 1, or 2. In some embodiments, n is 1.

In some embodiments, R$^2$ is hydrogen; R$^3$ is hydrogen; and n is 0.

In some embodiments, the compound of Formula (I) has the structure of Formula (Ia):

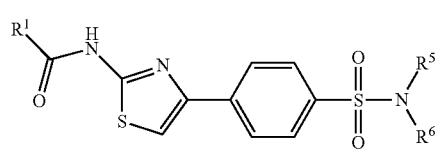

Formula (Ia)

In some embodiments, the compound of Formula (I) has the structure of Formula (Ib), Formula (Ic), or Formula (Id):

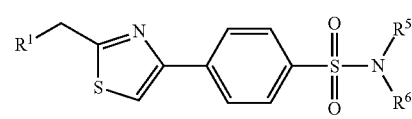

Formula (Ib)

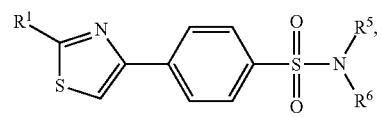

Formula (Ic)

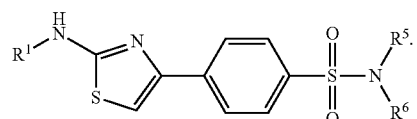

Formula (Id)

In some embodiments, R$^1$ is substituted or unsubstituted C$_1$-C$_8$alkyl.

In some embodiments, R$^1$ is selected from the group consisting of methyl, ethyl, n-propyl, i-propyl, n-butyl, sec-butyl, i-butyl, t-butyl, 1-ethyl-propyl, n-pentyl, n-hexyl, and n-heptyl.

In some embodiments, R$^1$ is 1-ethyl-propyl or sec-butyl.

In some embodiments, R$^1$ is substituted or unsubstituted aryl.

In some embodiments, R$^1$ is phenyl optionally substituted with halogen, —CN, —OH, C$_1$-C$_6$ alkyl, C$_1$-C$_6$haloalkyl, C$_1$-C$_6$alkoxy, or C$_1$-C$_6$haloalkoxy.

In some embodiments, R$^1$ is substituted or unsubstituted C$_3$-C$_8$cycloalkyl.

In some embodiments, R$^1$ is selected from the group consisting of cyclopropyl, cyclobutyl, cyclopentyl, and cyclohexyl.

In some embodiments, R$^5$ and R$^6$ are each independently substituted or unsubstituted C$_1$-C$_6$alkyl.

In some embodiments, R$^5$ and R$^6$ are each independently selected from methyl or ethyl.

In some embodiments, R$^5$ and R$^6$ are taken together with the nitrogen to which they are attached form a substituted or unsubstituted 4-, 5-, 6-, or 7-membered heterocycloalkyl.

In some embodiments, R$^5$ and R$^6$ are taken together with the nitrogen to which they are attached form a pyrrolidinyl, morpholinyl, piperidinyl, 4-methylpiperidinyl, 2-methylpiperidinyl, 3-methylpiperidinyl, thiomorpholinyl, piperazinyl, or 4-methylpiperazinyl.

In some embodiments, R$^1$ is sec-butyl; and R$^5$ and R$^6$ are each ethyl.

In some embodiments, the compound of Formula (I) has one of the following structures:

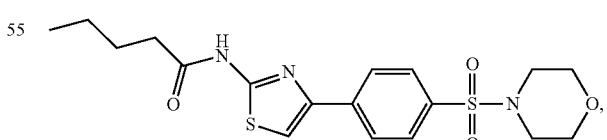

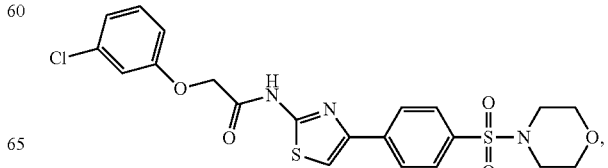

53
-continued
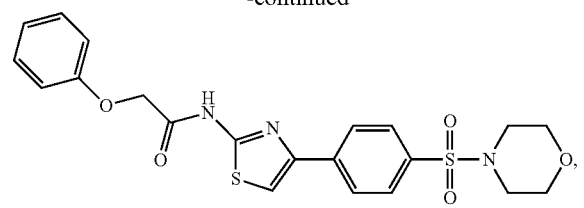
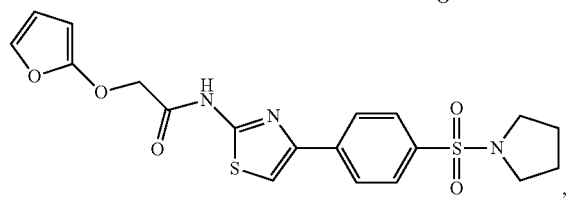
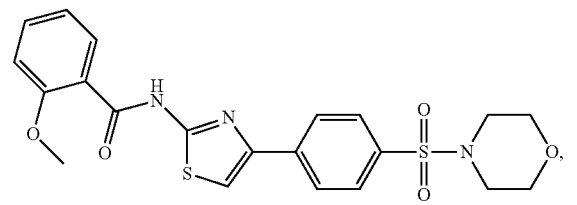
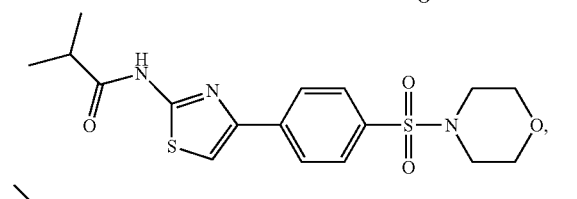
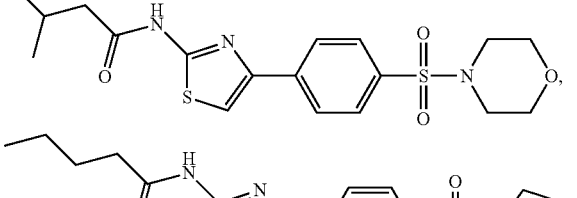
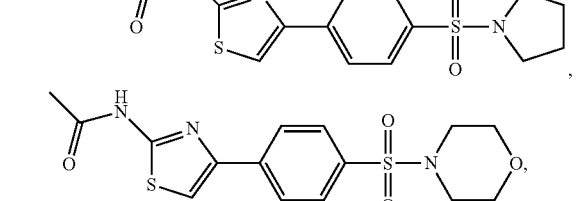
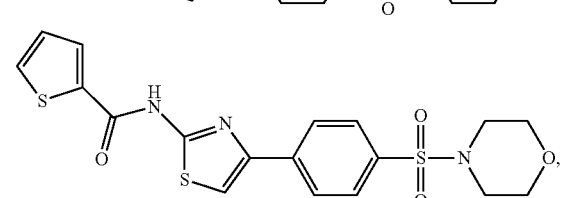
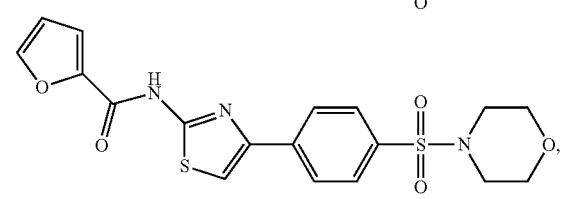
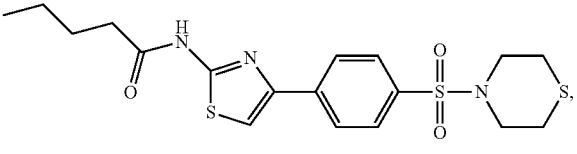
54
-continued
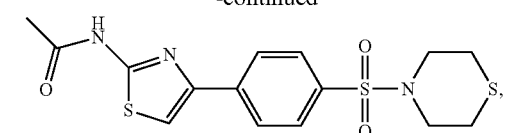
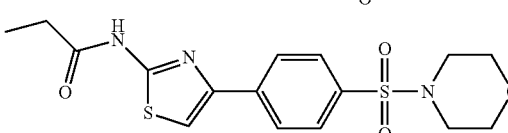
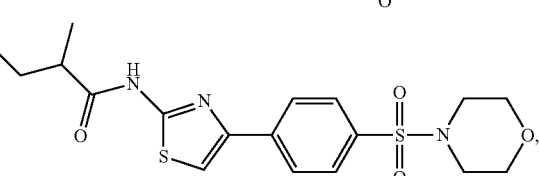
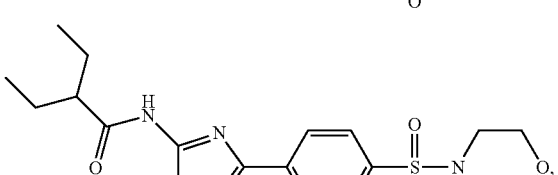
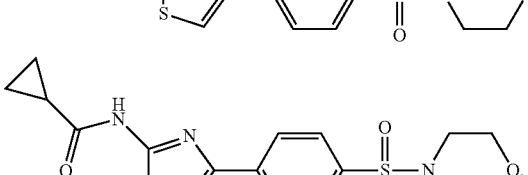
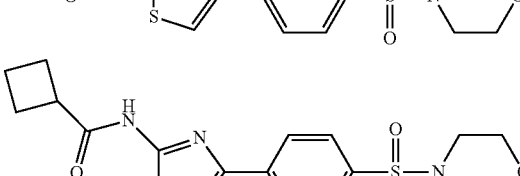
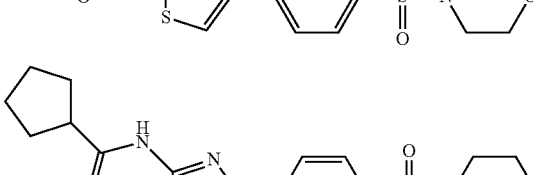
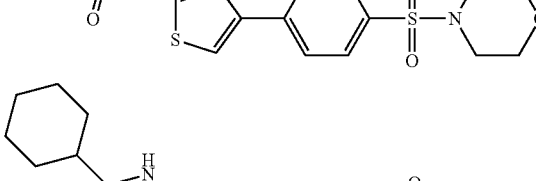
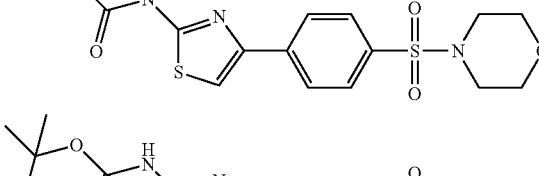
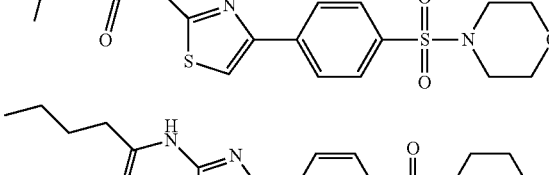
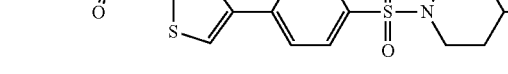

55
-continued
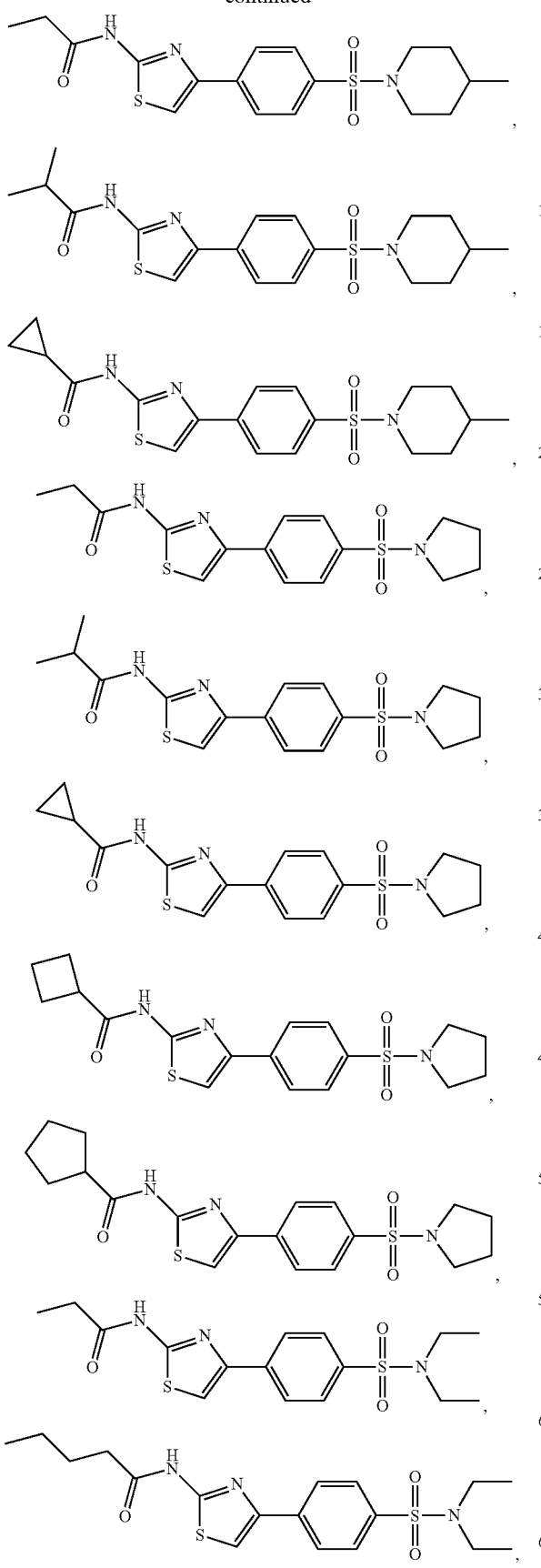
56
-continued
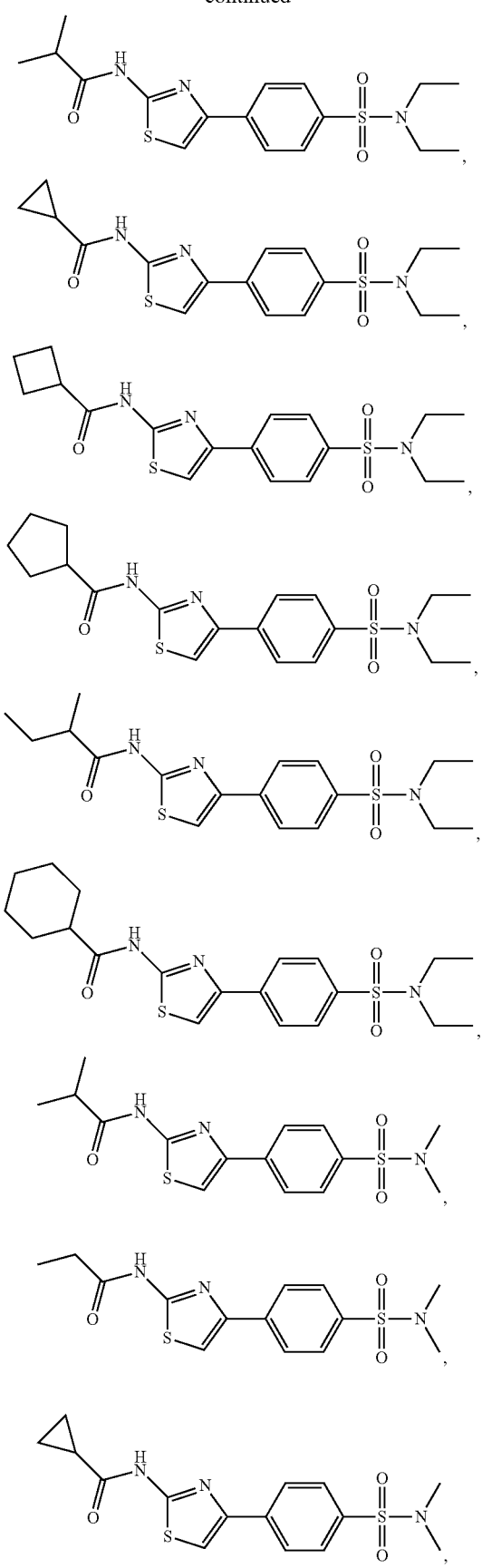

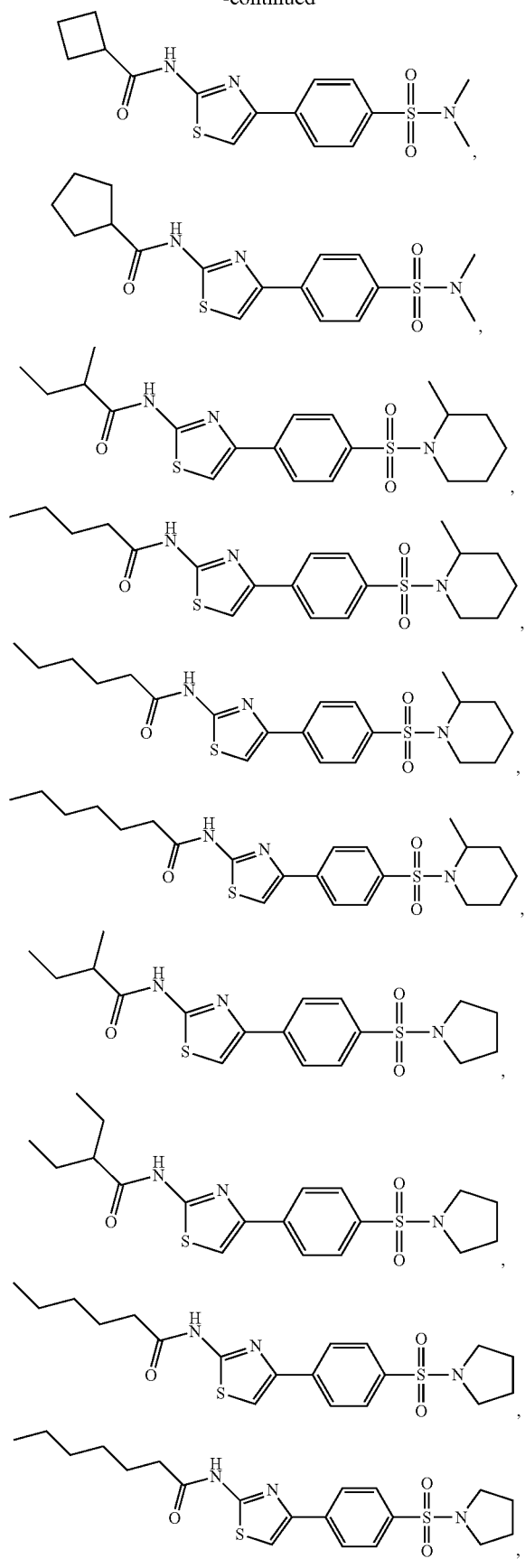
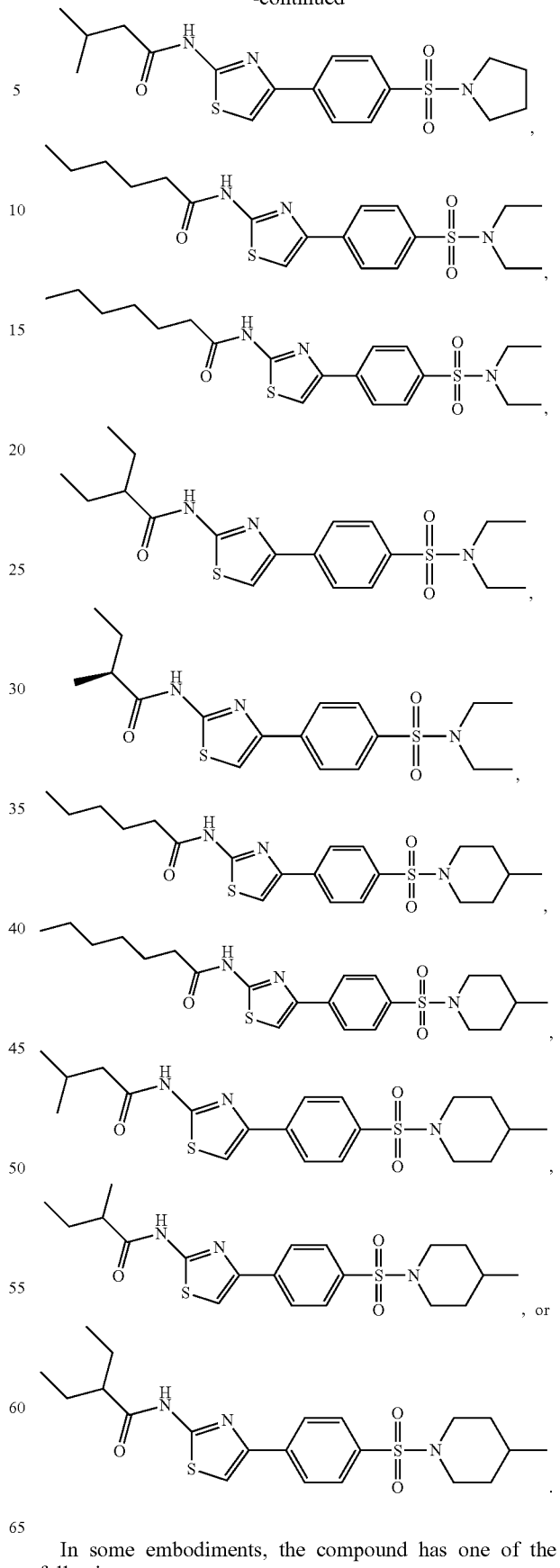
In some embodiments, the compound has one of the following structures:

61
-continued
62
-continued
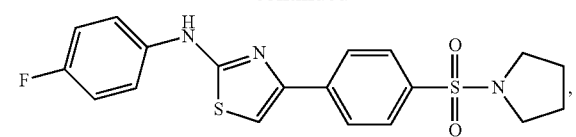
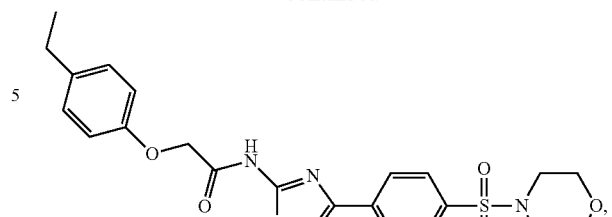

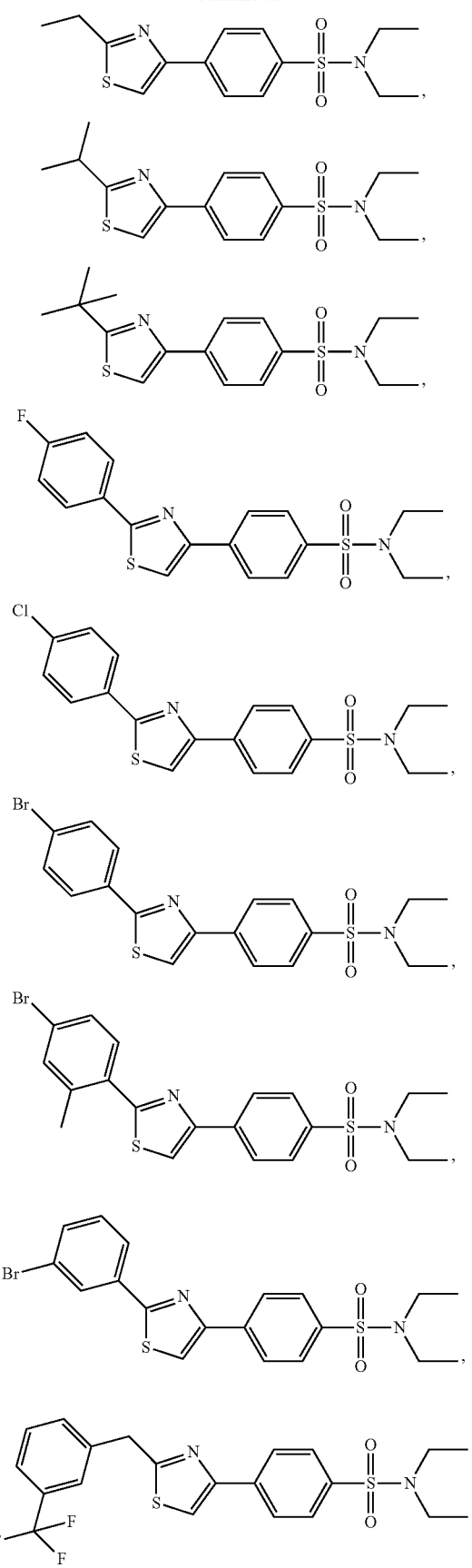
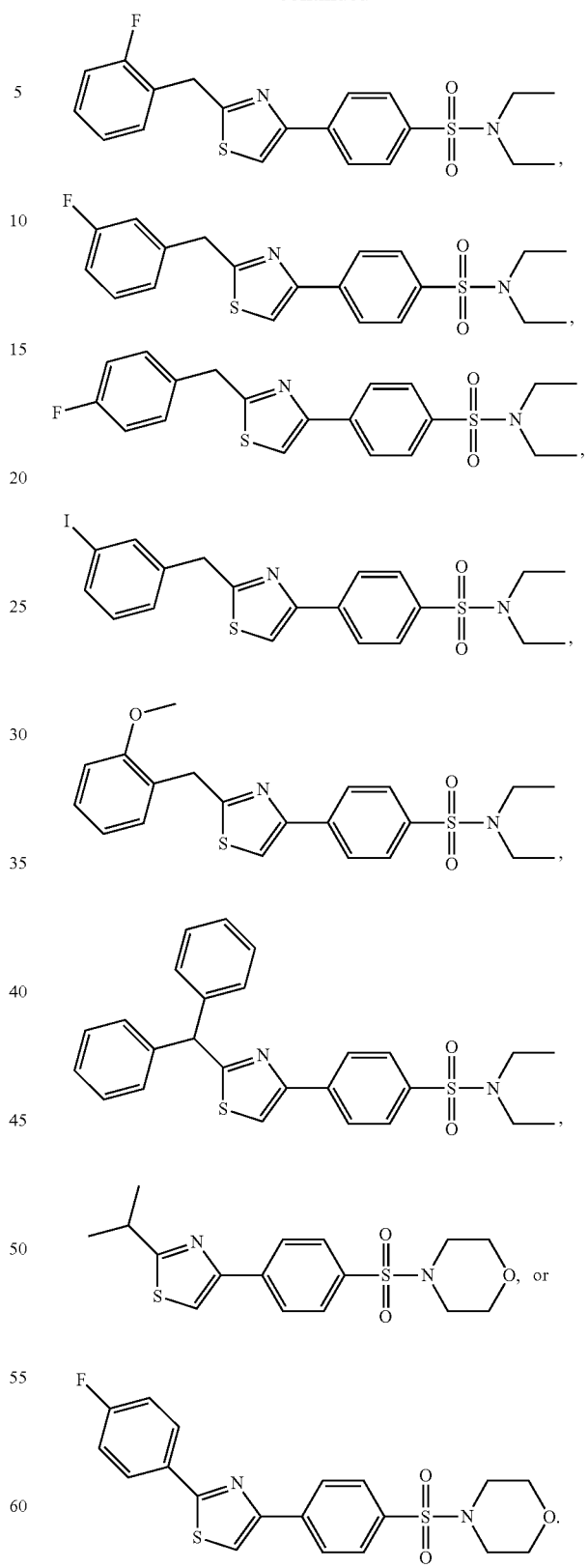
In one aspect, described herein is a compound that has the structure of Formula (II), or a pharmaceutically acceptable salt, or solvate thereof:

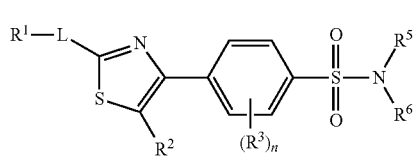

Formula (II)

wherein:

R[1] is substituted or unsubstituted $C_3$-$C_8$cycloalkyl;

L is absent, $C_1$-$C_4$alkylene, —N(R[4])—, —CH=N—N(R[4])—, —N(R[4])C(=O)—, or —C(=O)N(R[4])—, —C(=O)N(R[4])($C_1$-$C_4$alkylene)-, —N(R[4])C(=O)($C_1$-$C_4$alkylene)-, —($C_1$-$C_4$alkylene)C(=O) N(R[4])—, —($C_1$-$C_4$alkylene)N(R[4])C(=O)—, —C(=O)N(R[4])($C_1$-$C_4$alkylene)O—, —N(R[4])C(=O)($C_1$-$C_4$alkylene)O—, —O($C_1$-$C_4$alkylene)C(=O)N(R[4])—, or —O($C_1$-$C_4$alkylene) N(R[4])C(=O)—;

R[2] is hydrogen, halogen, —CN, —OH, substituted or unsubstituted $C_1$-$C_6$alkyl, substituted or unsubstituted $C_1$-$C_6$haloalkyl, substituted or unsubstituted $C_1$-$C_6$alkoxy, or substituted or unsubstituted $C_1$-$C_6$haloalkoxy;

each R[3] is independently selected from the group consisting of hydrogen, halogen, —CN, —OH, substituted or unsubstituted $C_1$-$C_6$alkyl, substituted or unsubstituted $C_1$-$C_6$haloalkyl, substituted or unsubstituted $C_1$-$C_6$alkoxy, and substituted or unsubstituted $C_1$-$C_6$haloalkoxy;

n is 0, 1, 2, 3, or 4;

R[4] is hydrogen, $C_1$-$C_6$alkyl, $C_1$-$C_6$haloalkyl, $C_3$-$C_8$cycloalkyl, or substituted or unsubstituted aryl;

R[5] and R[6] are each independently selected from the group consisting of hydrogen, substituted or unsubstituted $C_1$-$C_6$alkyl, substituted or unsubstituted $C_1$-$C_6$haloalkyl, substituted or unsubstituted $C_3$-$C_8$cycloalkyl, substituted or unsubstituted $C_2$-$C_8$heterocycloalkyl, substituted or unsubstituted aryl, substituted or unsubstituted heteroaryl, substituted or unsubstituted —$C_1$-$C_2$alkylene(aryl), and substituted or unsubstituted —$C_1$-$C_2$alkylene(heteroaryl);

or R[5] and R[6] are taken together with the nitrogen to which they are attached form a substituted or unsubstituted 4-, 5-, 6-, or 7-membered heterocycloalkyl.

In some embodiments, L is —C(=O)N(R[4])—; R[2] is hydrogen; R[3] is hydrogen; R[4] is hydrogen; and n is 0.

In some embodiments, R[1] is cyclopropyl, cyclobutyl, cyclopentyl, or cyclohexyl.

In some embodiments, R[5] and R[6] are each independently substituted or unsubstituted $C_1$-$C_6$alkyl.

In some embodiments, R[5] and R[6] are each methyl or ethyl.

In some embodiments, R[5] and R[6] are taken together with the nitrogen to which they are attached form a substituted or unsubstituted 4-, 5-, 6-, or 7-membered heterocycloalkyl.

In some embodiments, R[5] and R[6] are taken together with the nitrogen to which they are attached form a pyrrolidinyl, morpholinyl, piperidinyl, 4-methylpiperidinyl, 2-methylpiperidinyl, 3-methylpiperidinyl, thiomorpholinyl, piperazinyl, or 4-methylpiperazinyl.

In some embodiments, the compound has one of the following structures:

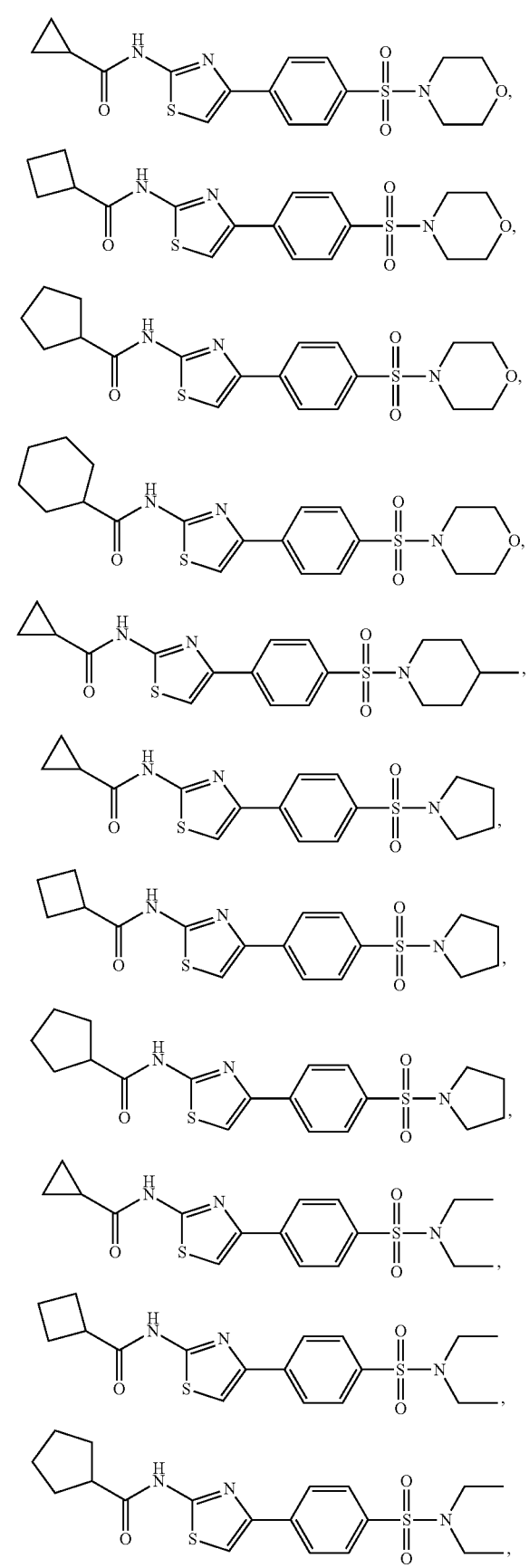

67

-continued

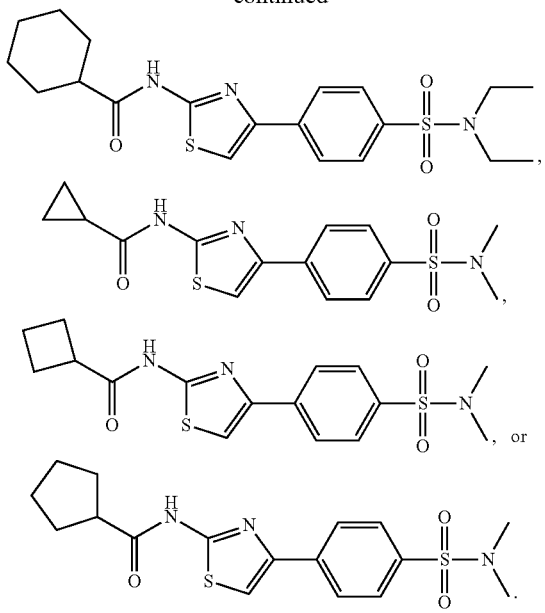

In another aspect, described herein is a compound of formula (III):

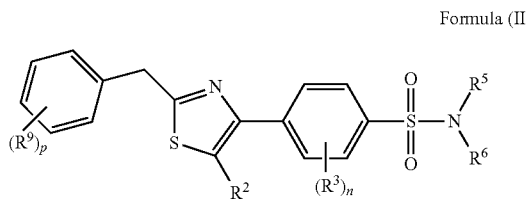

Formula (III)

wherein:
R² is hydrogen, halogen, —CN, —OH, substituted or unsubstituted C₁-C₆alkyl, substituted or unsubstituted C₁-C₆haloalkyl, or substituted or unsubstituted C₁-C₆alkoxy;
each R³ is independently selected from the group consisting of hydrogen, halogen, —CN, —OH, substituted or unsubstituted C₁-C₆alkyl, substituted or unsubstituted C₁-C₆haloalkyl, and substituted or unsubstituted C₁-C₆alkoxy;
R⁵ and R⁶ are each independently selected from the group consisting of hydrogen, substituted or unsubstituted C₁-C₆alkyl, substituted or unsubstituted C₁-C₆haloalkyl, substituted or unsubstituted C₃-C₈cycloalkyl, substituted or unsubstituted C₂-C₈heterocycloalkyl, substituted or unsubstituted aryl, substituted or unsubstituted heteroaryl, substituted or unsubstituted —C₁-C₂alkylene(aryl), and substituted or unsubstituted —C₁-C₂alkylene(heteroaryl);
or R⁵ and R⁶ are taken together with the nitrogen to which they are attached form a substituted or unsubstituted 4-, 5-, 6-, or 7-membered heterocycloalkyl;
each R⁹ is independently selected from the group consisting of hydrogen, halogen, —CN, —OH, substituted or unsubstituted C₁-C₆alkyl, C₁-C₆haloalkyl, substituted or unsubstituted C₁-C₆alkoxy, and substituted or unsubstituted C₁-C₆haloalkoxy;
n is 0, 1, 2, 3, or 4; and

68 p is 1, 2, 3, 4, or 5;
or a pharmaceutically acceptable salt or solvate thereof.
In some embodiments, R² is hydrogen; R³ is hydrogen; and n is 0.
In some embodiments, R⁹ is halogen, C₁-C₆alkyl, C₁-C₆haloalkyl, or C₁-C₆alkoxy.
In some embodiments, R⁵ and R⁶ are each independently substituted or unsubstituted C₁-C₆alkyl.
In some embodiments, R⁵ and R⁶ are each methyl or ethyl.
In some embodiments, R⁵ and R⁶ are taken together with the nitrogen to which they are attached form a substituted or unsubstituted 4-, 5-, 6-, or 7-membered heterocycloalkyl.
In some embodiments, R⁵ and R⁶ are taken together with the nitrogen to which they are attached form a pyrrolidinyl, morpholinyl, piperidinyl, 4-methylpiperidinyl, 2-methylpiperidinyl, 3-methylpiperidinyl, thiomorpholinyl, piperazinyl, or 4-methylpiperazinyl.
In some embodiments, each R⁹ is independently selected from the group consisting of halogen, —CN, —OH, substituted or unsubstituted C₁-C₆alkyl, C₁-C₆haloalkyl, substituted or unsubstituted C₁-C₆alkoxy, and substituted or unsubstituted C₁-C₆haloalkoxy.
In some embodiments, the compound has one of the following structures:

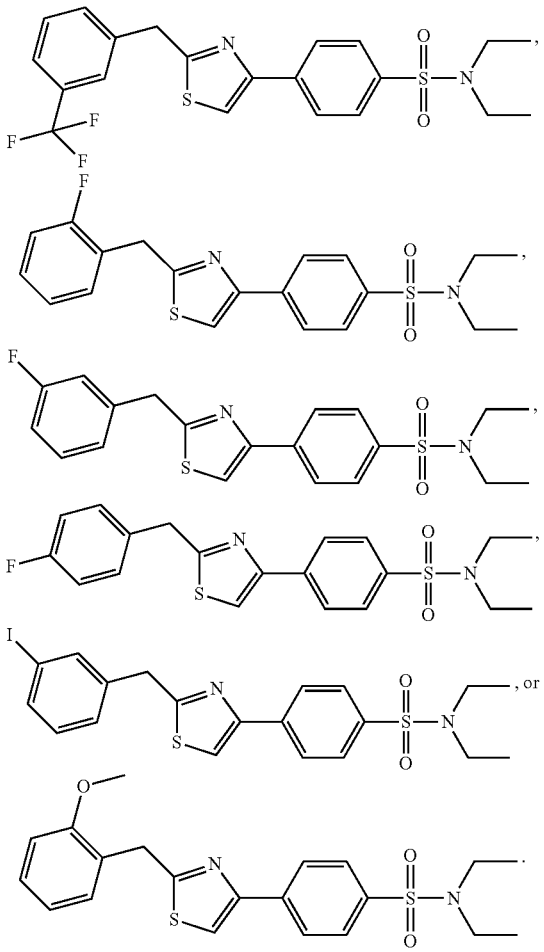

In another aspect, described herein is a compound that has the structure of Formula (IV):

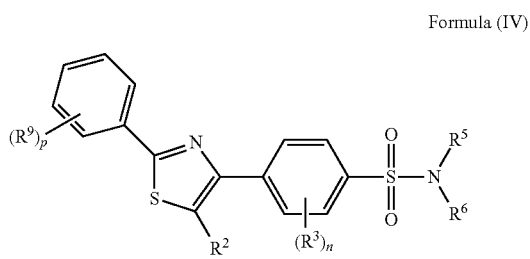

Formula (IV)

wherein:

$R^2$ is hydrogen, halogen, —CN, —OH, substituted or unsubstituted $C_1$-$C_6$alkyl, substituted or unsubstituted $C_1$-$C_6$haloalkyl, substituted or unsubstituted $C_1$-$C_6$alkoxy, or substituted or unsubstituted $C_1$-$C_6$haloalkoxy;

each $R^3$ is independently selected from the group consisting of hydrogen, halogen, —CN, —OH, substituted or unsubstituted $C_1$-$C_6$alkyl, substituted or unsubstituted $C_1$-$C_6$haloalkyl, substituted or unsubstituted $C_1$-$C_6$alkoxy, and substituted or unsubstituted $C_1$-$C_6$haloalkoxy;

$R^5$ and $R^6$ are each independently selected from the group consisting of hydrogen, substituted or unsubstituted $C_1$-$C_6$alkyl, substituted or unsubstituted $C_1$-$C_6$haloalkyl, substituted or unsubstituted $C_3$-$C_8$cycloalkyl, substituted or unsubstituted $C_2$-$C_8$heterocycloalkyl, substituted or unsubstituted aryl, substituted or unsubstituted heteroaryl, substituted or unsubstituted —$C_1$-$C_2$alkylene(aryl), and substituted or unsubstituted —$C_1$-$C_2$alkylene(heteroaryl);

or $R^5$ and $R^6$ are taken together with the nitrogen to which they are attached form a substituted or unsubstituted 4-, 5-, 6-, or 7-membered heterocycloalkyl;

each $R^9$ is independently selected from the group consisting of hydrogen, halogen, —CN, —OH, substituted or unsubstituted $C_1$-$C_6$alkyl, $C_1$-$C_6$haloalkyl, substituted or unsubstituted $C_1$-$C_6$alkoxy, and substituted or unsubstituted $C_1$-$C_6$haloalkoxy;

n is 0, 1, 2, 3, or 4; and p is 0, 1, 2, 3, 4, or 5;

or a pharmaceutically acceptable salt, or solvate thereof.

In some embodiments, $R^3$ is hydrogen; $R^4$ is hydrogen; and n is 0.

In some embodiments, each $R^9$ is independently halogen or substituted or unsubstituted $C_1$-$C_6$alkyl; and p is 1 or 2.

In some embodiments, $R^5$ and $R^6$ are each independently substituted or unsubstituted $C_1$-$C_6$alkyl.

In some embodiments, $R^5$ and $R^6$ are each methyl or ethyl.

In some embodiments, $R^5$ and $R^6$ are taken together with the nitrogen to which they are attached form a substituted or unsubstituted 4-, 5-, 6-, or 7-membered heterocycloalkyl.

In some embodiments, $R^5$ and $R^6$ are taken together with the nitrogen to which they are attached form a pyrrolidinyl, morpholinyl, piperidinyl, 4-methylpiperidinyl, 2-methylpiperidinyl, 3-methylpiperidinyl, thiomorpholinyl, piperazinyl, or 4-methylpiperazinyl.

In some embodiments, the compound has one of the following structures:

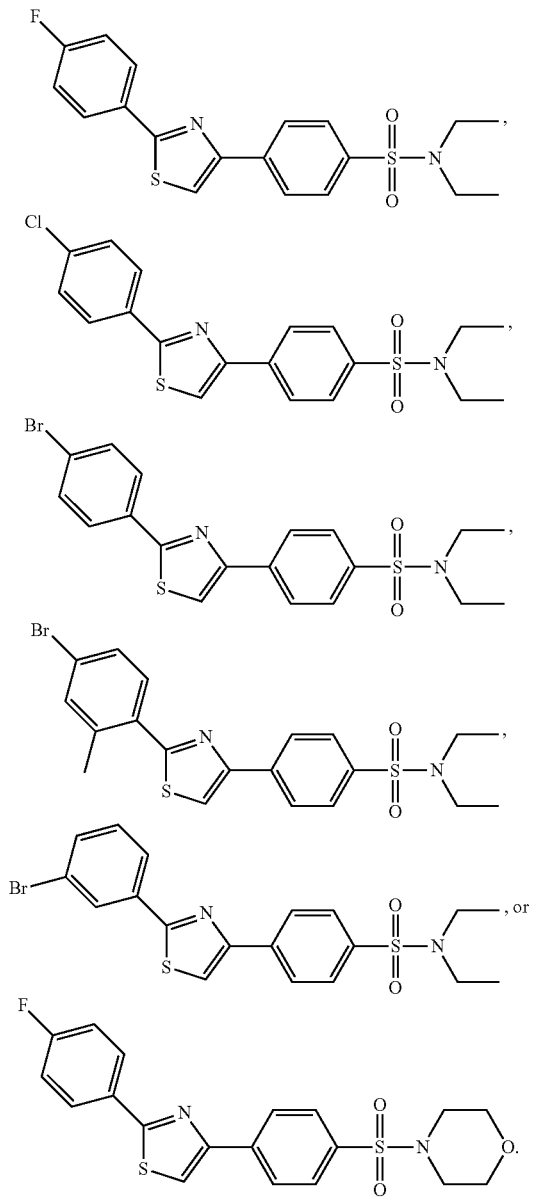

In yet another aspect, described herein is a compound that has the structure of Formula (V):

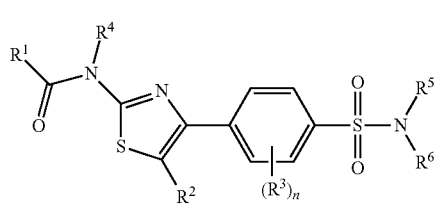

Formula (V)

wherein:

$R^1$ is substituted or unsubstituted $C_1$-$C_8$alkyl, substituted or unsubstituted $C_1$-$C_8$haloalkyl, substituted or unsubstituted $C_3$-$C_8$cycloalkyl, substituted or unsubstituted $C_2$-$C_8$heterocycloalkyl, substituted or unsubstituted aryl, substituted or unsubstituted heteroaryl, substituted or unsubstituted —C$_1$-C$_2$alkylene(aryl), or substituted or unsubstituted —C$_1$-C$_2$alkylene(heteroaryl);

R$^2$ is hydrogen, halogen, —CN, —OH, substituted or unsubstituted C$_1$-C$_6$alkyl, substituted or unsubstituted C$_1$-C$_6$haloalkyl, substituted or unsubstituted C$_1$-C$_6$alkoxy, or substituted or unsubstituted C$_1$-C$_6$haloalkoxy;

each R$^3$ is independently selected from the group consisting of hydrogen, halogen, —CN, —OH, substituted or unsubstituted C$_1$-C$_6$alkyl, substituted or unsubstituted C$_1$-C$_6$haloalkyl, substituted or unsubstituted C$_1$-C$_6$alkoxy, and substituted or unsubstituted C$_1$-C$_6$haloalkoxy;

R$^4$ is hydrogen, C$_1$-C$_6$alkyl, C$_1$-C$_6$haloalkyl, C$_3$-C$_8$cycloalkyl, or substituted or unsubstituted aryl;

R$^5$ and R$^6$ are each independently selected from the group consisting of methyl or ethyl;

or R$^5$ and R$^6$ are taken together with the nitrogen to which they are attached form a piperidinyl, 4-methylpiperidinyl, 2-methylpiperidinyl, 3-methylpiperidinyl, piperazinyl, or 4-methylpiperazinyl; and n is 0, 1, 2, 3, or 4;

or a pharmaceutically acceptable salt or solvate thereof.

In some embodiments, R$^2$ is hydrogen; R$^3$ is hydrogen; R$^4$ is hydrogen; and n is 0.

In some embodiments, R$^1$ is substituted or unsubstituted C$_1$-C$_8$alkyl.

In some embodiments, R$^1$ is methyl, ethyl, n-propyl, i-propyl, n-butyl, sec-butyl, i-butyl, t-butyl, 1-ethyl-propyl, n-pentyl, n-hexyl, or n-heptyl.

In some embodiments, R$^1$ is 1-ethyl-propyl or sec-butyl.

In some embodiments, R$^5$ and R$^6$ are each methyl or ethyl.

In some embodiments, R$^5$ and R$^6$ are taken together with the nitrogen to which they are attached form a 4-methylpiperidinyl or 2-methylpiperidinyl.

In some embodiments, the compound has one of the following structures:

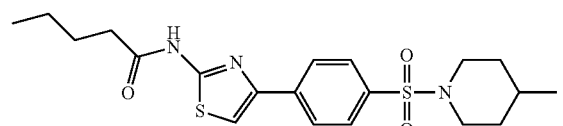

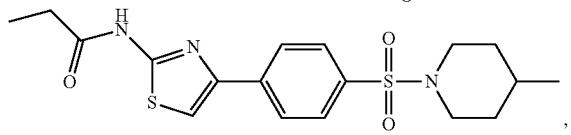

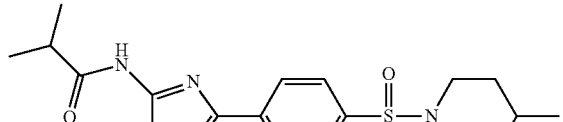

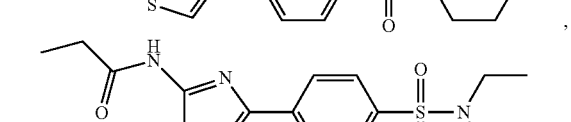

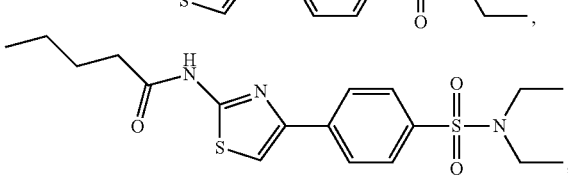

-continued

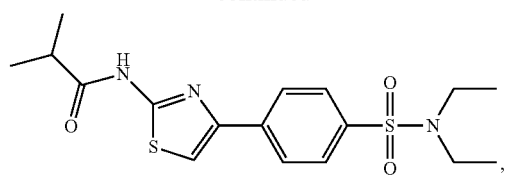

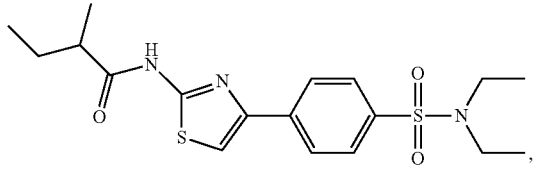

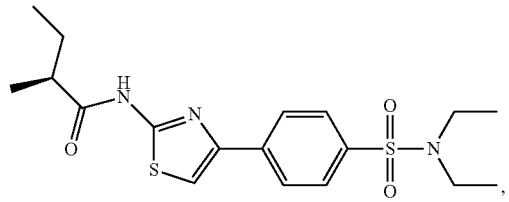

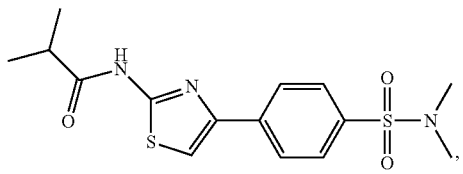

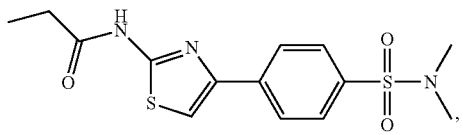

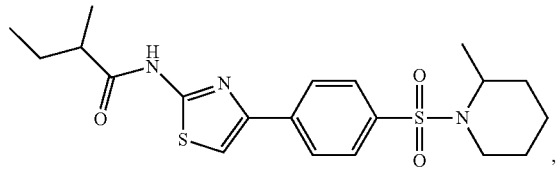

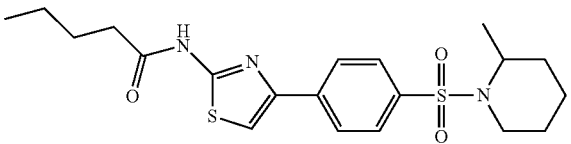

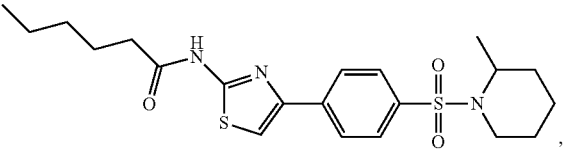

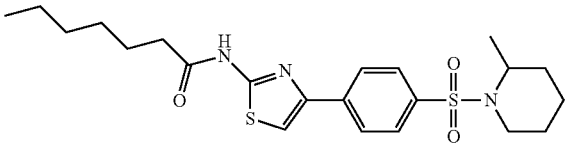

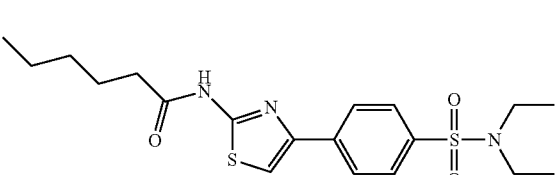

-continued
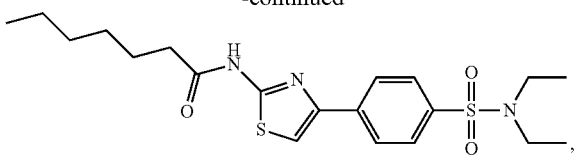
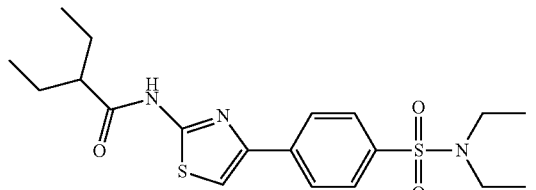
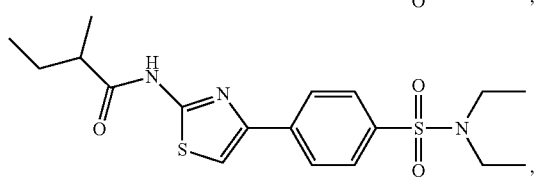
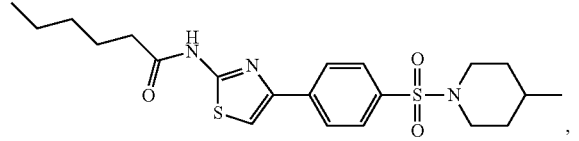
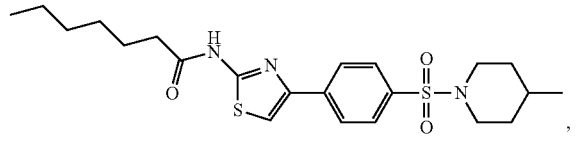
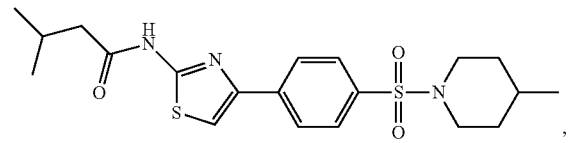
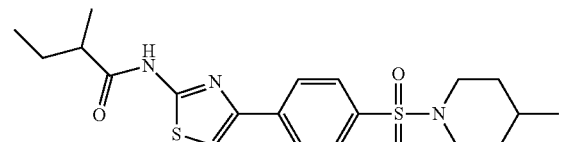
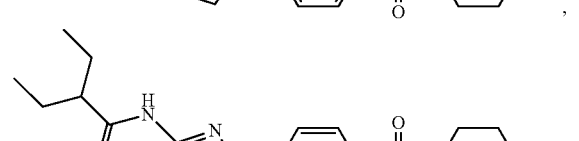
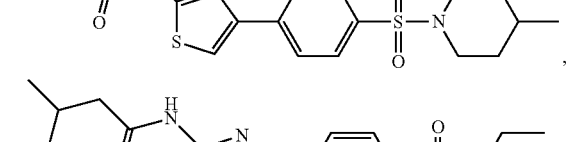
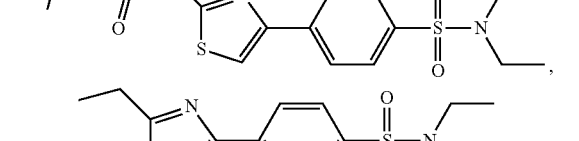
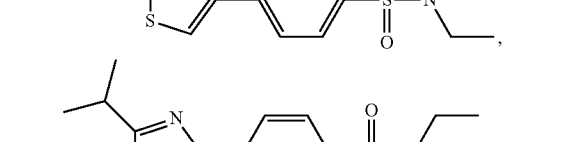
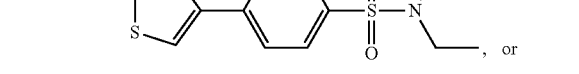
-continued
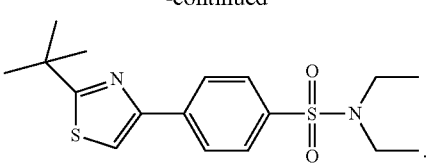
In another aspect, described herein is a compound or a pharmaceutically acceptable salt or solvate thereof selected that has one of the following structures:
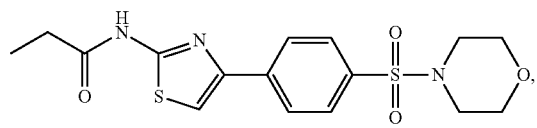
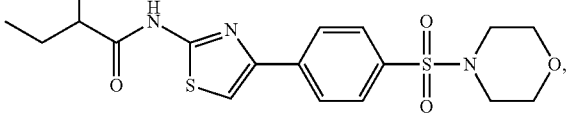
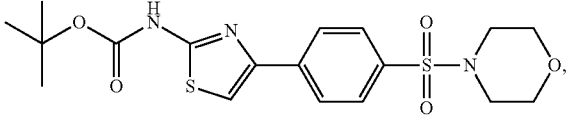
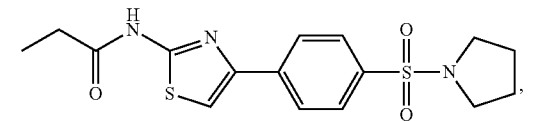
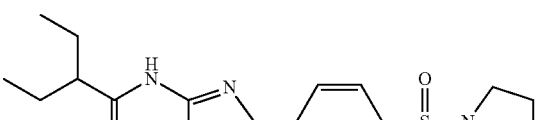
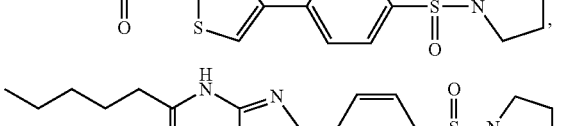
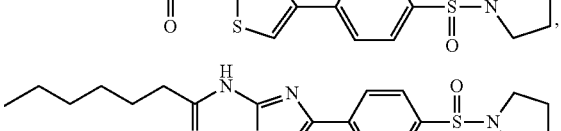
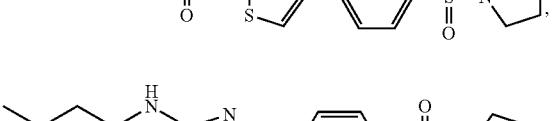
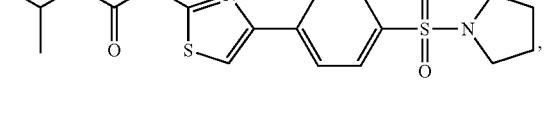
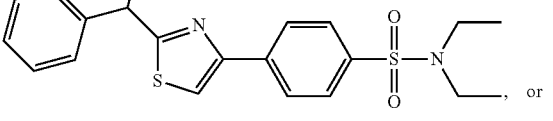

-continued

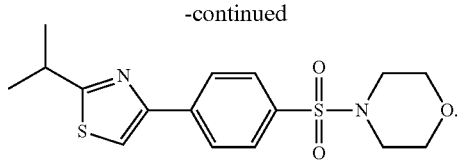

In some embodiments, compounds described herein have the following structure:

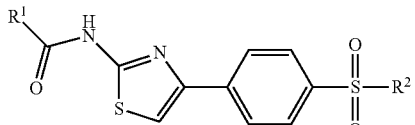

In some embodiments, R¹ is as described in Table 1. In some embodiments, R² is as described in Table 1. In some embodiments, R¹ and R² are as described in Table 1.

In some embodiments, compounds described herein have the following structure:

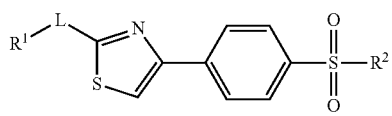

In some embodiments, -L-R¹ is as described in Table 2. In some embodiments, R² is as described in Table 2. In some embodiments, -L-R¹ and R² are as described in Table 2.

Any combination of the groups described above or below for the various variables is contemplated herein.

Non-limiting examples of compounds described herein are presented in Table 1 and Table 2.

TABLE 1

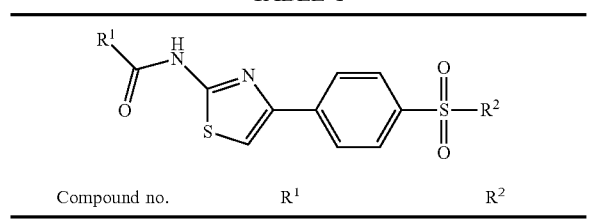

| Compound no. | R¹ | R² |
|---|---|---|
| 1 | n-butyl | morpholine |
| 2 | 3ClPhOCH₂ | morpholine |
| 3 | PhOCH₂ | morpholine |
| 4 | 2-furan | pyrrolidine |
| 5 | 2-OMePh | morpholine |
| 6 | i-propyl | morpholine |
| 7 | i-butyl | morpholine |
| 8 | n-butyl | pyrrolidine |
| 9 | methyl | morpholine |
| 10 | 2-thiophene | morpholine |
| 11 | 2-furan | morpholine |
| 12 | n-butyl | thiomorpholine |
| 13 | methyl | thiomorpholine |
| 14 | ethyl | morpholine |
| 15 | sec-butyl | morpholine |
| 16 | 1-Et-propyl | morpholine |
| 17 | cyclo-propyl | morpholine |
| 18 | cyclo-butyl | morpholine |
| 19 | cyclo-pentyl | morpholine |
| 20 | cyclo-hexyl | morpholine |
| 21 | O-t-butyl | morpholine |
| 22 | n-butyl | 4methylpiperidyl |

TABLE 1-continued

| Compound no. | R¹ | R² |
|---|---|---|
| 23 | ethyl | 4methylpiperidyl |
| 24 | i-propyl | 4methylpiperidyl |
| 25 | cyclo-propyl | 4methylpiperidyl |
| 26 | ethyl | pyrrolidine |
| 27 | i-propyl | pyrrolidine |
| 28 | cyclo-propyl | pyrrolidine |
| 29 | cyclo-butyl | pyrrolidine |
| 30 | cyclo-pentyl | pyrrolidine |
| 31 | ethyl | N(Et)₂ |
| 32 | n-butyl | N(Et)₂ |
| 33 | i-propyl | N(Et)₂ |
| 34 | cyclo-propyl | N(Et)₂ |
| 35 | cyclo-butyl | N(Et)₂ |
| 36 | cyclo-pentyl | N(Et)₂ |
| 37 | sec-butyl | N(Et)₂ |
| 38 | cyclo-hexyl | N(Et)₂ |
| 39 | i-propyl | N(Me)₂ |
| 40 | ethyl | N(Me)₂ |
| 41 | cyclo-propyl | N(Me)₂ |
| 42 | cyclo-butyl | N(Me)₂ |
| 43 | cyclo-pentyl | N(Me)₂ |
| 44 | sec-butyl | 2methylpiperidyl |
| 45 | n-butyl | 2methylpiperidyl |
| 46 | n-propyl | 2methylpiperidyl |
| 47 | n-heptyl | 2methylpiperidyl |
| 48 | sec-butyl | pyrrolidine |
| 49 | 1-Et-propyl | pyrrolidine |
| 50 | n-pentyl | pyrrolidine |
| 51 | n-hexyl | pyrrolidine |
| 52 | i-butyl | pyrrolidine |
| 53 | n-pentyl | N(Et)₂ |
| 54 | n-hexyl | N(Et)₂ |
| 55 | 1-Et-propyl | N(Et)₂ |
| 56 | (S) sec-butyl | N(Et)₂ |
| 57 | n-pentyl | 4methylpiperidyl |
| 58 | n-hexyl | 4methylpiperidyl |
| 59 | i-butyl | 4methylpiperidyl |
| 60 | sec-butyl | 4methylpiperidyl |
| 61 | 1-Et-propyl | 4methylpiperidyl |
| 62 | thien-2-yl | azepane |
| 63 | 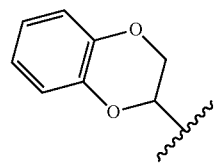 [SMILES: *C1COc2ccccc2O1] | pyrrolidine |
| 65 | 3-ethoxyphenyl | morpholine |
| 66 | 3-methoxyphenyl | morpholine |
| 67 | thien-2-yl | pyrrolidine |
| 70 | phenyl | azepane |
| 71 | 4-chlorophenoxymethyl | morpholine |
| 72 | phenyl | morpholine |
| 73 | 4-methoxyphenyl | morpholine |
| 74 | 1-(2-methoxyphenoxy)ethyl | morpholine |
| 75 | 2-methoxyphenoxymethyl | morpholine |
| 91 | 4-ethylphenoxymethyl | morpholine |
| 92 | 4-methylphenoxymethyl | morpholine |
| 93 | 2-methylphenoxymethyl | morpholine |
| 94 | 3-methylphenoxymethyl | morpholine |

TABLE 1-continued

Structure: R¹-C(O)-NH-[thiazole]-phenyl-S(O)₂-R²

| Compound no. | R¹ | R² |
|---|---|---|
| 95 | (2,3-dihydrobenzo[1,4]dioxin-2-yl) | morpholine |
| 99 | 2-methylpropyl | N(Et)₂ |
| 117 | n-pentyl | 2methylpiperidyl |
| 118 | n-hexyl | 2methylpiperidyl |

TABLE 2

Structure: R¹-L-[thiazole]-phenyl-S(O)₂-R²

| Compound no. | R¹—L— | R² |
|---|---|---|
| 64 | Pyridin-3-yl | piperidine |
| 68 | methyl | azepane |
| 69 | Pyridin-3-yl | pyrrolidine |
| 76 | 3,4-dimethylphenylamino | pyrrolidine |
| 77 | 3,5-dimethylphenylamino | pyrrolidine |
| 78 | 4-bromophenylamino | pyrrolidine |
| 79 | 3-chloro-4-methylphenylamino | morpholine |
| 80 | 4-fluorophenylamino | pyrrolidine |
| 81 | Pyridin-3-yl | morpholine |
| 82 | methyl | N(Et)₂ |
| 83 | Pyridin-3-yl | N(Me)₂ |
| 84 | (furan-2-yl-methylidene-hydrazinyl) | N(Me)₂ |
| 85 | 4-methylphenylamino | morpholine |
| 86 | methyl | morpholine |
| 87 | (4-hydroxy-3-methoxybenzylidene-hydrazinyl) | N(Me)₂ |
| 88 | (4-hydroxybenzylidene-hydrazinyl) | N(Me)₂ |
| 89 | amino | piperidine |
| 90 | methylamino | piperidine |
| 96 | benzyl | morpholine |
| 97 | (4-methylphenyl-NH-C(O)-CH₂-) | morpholine |
| 98 | pyrrolidine | morpholine |
| 100 | ethyl | N(Et)₂ |
| 101 | isopropyl | N(Et)₂ |
| 102 | Tert-butyl | N(Et)₂ |
| 103 | 4-fluorophenyl | N(Et)₂ |
| 104 | 4-chlorophenyl | N(Et)₂ |
| 105 | 4-bromophenyl | N(Et)₂ |
| 106 | 4-bromo-2-methylphenyl | N(Et)₂ |
| 107 | 3-bromophenyl | N(Et)₂ |
| 108 | 3-trifluoromethylphenylmethyl | N(Et)₂ |
| 109 | 2-fluorophenylmethyl | N(Et)₂ |
| 110 | 3-fluorophenylmethyl | N(Et)₂ |
| 111 | 4-fluorophenylmethyl | N(Et)₂ |
| 112 | 3-iodophenylmethyl | N(Et)₂ |
| 113 | 2-methoxyphenylmethyl | N(Et)₂ |
| 114 | (diphenylmethyl) | N(Et)₂ |
| 115 | isopropyl | morpholine |
| 116 | 4-fluorophenyl | morpholine |

Further Forms of Compounds

In one aspect, the compound of Formula (I), Formula (Ia), Formula (Ib), Formula (Ic), Formula (Id), Formula (II), Formula (III), Formula (IV), or Formula (V), possesses one or more stereocenters and each stereocenter exists independently in either the R or S configuration. The compounds presented herein include all diastereomeric, enantiomeric, and epimeric forms as well as the appropriate mixtures thereof. The compounds and methods provided herein include all cis, trans, syn, anti, entgegen (E), and zusammen (Z) isomers as well as the appropriate mixtures thereof. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In one aspect, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug. In some embodiments, the design of a prodrug increases the effective water solubility. An example, without limitation, of a prodrug is a compound described herein, which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. A further example of a prodrug might be a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

In one aspect, prodrugs are designed to alter the metabolic stability or the transport characteristics of a drug, to mask side effects or toxicity, to improve the flavor of a drug or to alter other characteristics or properties of a drug. By virtue of knowledge of pharmacokinetic, pharmacodynamic processes and drug metabolism in vivo, once a pharmaceutically active compound is known, the design prodrugs of the compound is possible. (see, for example, Nogrady (1985) *Medicinal Chemistry A Biochemical Approach*, Oxford University Press, New York, pages 388-392; Silverman (1992), The Organic Chemistry of Drug Design and Drug Action, Academic Press, Inc., San Diego, pages 352-401, Rooseboom et al., Pharmacological Reviews, 56:53-102, 2004; Aesop Cho, "Recent Advances in Oral Prodrug Discovery", *Annual Reports in Medicinal Chemistry*, Vol. 41, 395-407, 2006; T. Higuchi and V. Stella, *Pro-drugs as Novel Delivery Systems*, Vol. 14 of the A.C.S. Symposium Series).

In some cases, some of the herein-described compounds may be a prodrug for another derivative or active compound.

In some embodiments, sites on the aromatic ring portion of compounds described herein are susceptible to various metabolic reactions Therefore incorporation of appropriate substituents on the aromatic ring structures will reduce, minimize or eliminate this metabolic pathway. In specific embodiments, the appropriate substituent to decrease or eliminate the susceptibility of the aromatic ring to metabolic reactions is, by way of example only, a halogen, or an alkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In additional or further embodiments, the compounds described herein are metabolized upon administration to an organism in need to produce a metabolite that is then used to produce a desired effect, including a desired therapeutic effect.

"Pharmaceutically acceptable" as used herein, refers a material, such as a carrier or diluent, which does not abrogate the biological activity or properties of the compound, and is relatively nontoxic, i.e., the material may be administered to an individual without causing undesirable biological effects or interacting in a deleterious manner with any of the components of the composition in which it is contained.

The term "pharmaceutically acceptable salt" refers to a formulation of a compound that does not cause significant irritation to an organism to which it is administered and does not abrogate the biological activity and properties of the compound. In some embodiments, pharmaceutically acceptable salts are obtained by reacting a compound of Formula (I), Formula (Ia), Formula (Ib), Formula (Ic), Formula (Id), Formula (II), Formula (III), Formula (IV), or Formula (V) with acids. Pharmaceutically acceptable salts are also obtained by reacting a compound of Formula (I), Formula (Ia), Formula (Ib), Formula (Ic), Formula (Id), Formula (II), Formula (III), Formula (IV), or Formula (V) with a base to form a salt.

Compounds described herein may be formed as, and/or used as, pharmaceutically acceptable salts. The type of pharmaceutical acceptable salts, include, but are not limited to: (1) acid addition salts, formed by reacting the free base form of the compound with a pharmaceutically acceptable: inorganic acid, such as, for example, hydrochloric acid, hydrobromic acid, sulfuric acid, phosphoric acid, metaphosphoric acid, and the like; or with an organic acid, such as, for example, acetic acid, propionic acid, hexanoic acid, cyclopentanepropionic acid, glycolic acid, pyruvic acid, lactic acid, malonic acid, succinic acid, malic acid, maleic acid, fumaric acid, trifluoroacetic acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, toluenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, butyric acid, phenylacetic acid, phenylbutyric acid, valproic acid, and the like; (2) salts formed when an acidic proton present in the parent compound is replaced by a metal ion, e.g., an alkali metal ion (e.g. lithium, sodium, potassium), an alkaline earth ion (e.g. magnesium, or calcium), or an aluminum ion. In some cases, compounds described herein may coordinate with an organic base, such as, but not limited to, ethanolamine, diethanolamine, triethanolamine, tromethamine, N-methylglucamine, dicyclohexylamine, tris(hydroxymethyl)methylamine. In other cases, compounds described herein may form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, sodium hydroxide, and the like.

It should be understood that a reference to a pharmaceutically acceptable salt includes the solvent addition forms, particularly solvates. Solvates contain either stoichiometric or non-stoichiometric amounts of a solvent, and may be formed during the process of crystallization with pharmaceutically acceptable solvents such as water, ethanol, and the like. Hydrates are formed when the solvent is water, or alcoholates are formed when the solvent is alcohol. Solvates of compounds described herein can be conveniently prepared or formed during the processes described herein. In addition, the compounds provided herein can exist in unsolvated as well as solvated forms. In general, the solvated forms are considered equivalent to the unsolvated forms for the purposes of the compounds and methods provided herein.

Synthesis of Compounds

In some embodiments, the synthesis of compounds described herein are accomplished using means described in the chemical literature, using the methods described herein, or by a combination thereof. In addition, solvents, temperatures and other reaction conditions presented herein may vary.

In other embodiments, the starting materials and reagents used for the synthesis of the compounds described herein are synthesized or are obtained from commercial sources, such as, but not limited to, Sigma-Aldrich, Fisher Scientific (Fisher Chemicals), and Acros Organics.

In further embodiments, the compounds described herein, and other related compounds having different substituents are synthesized using techniques and materials described herein as well as those that are recognized in the field, such as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4$^{th}$ Ed., Vols. A and B (Plenum 2000, 2001), and Green and Wuts, Protective Groups in Organic Synthesis 3$^{rd}$ Ed., (Wiley 1999) (all of which are incorporated by reference for such disclosure). General methods for the preparation of compounds as disclosed herein may be derived from reactions and the reactions may be modified by the use of appropriate reagents and conditions, for the introduction of the various moieties found in the formulae as provided herein. As a guide the following synthetic methods may be utilized.

In the reactions described, it may be necessary to protect reactive functional groups, for example hydroxy, amino, imino, thio or carboxy groups, where these are desired in the final product, in order to avoid their unwanted participation in reactions. A detailed description of techniques applicable to the creation of protecting groups and their removal are described in Greene and Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure).

In some embodiments, compounds described herein are prepared as shown in Scheme A or Scheme B.

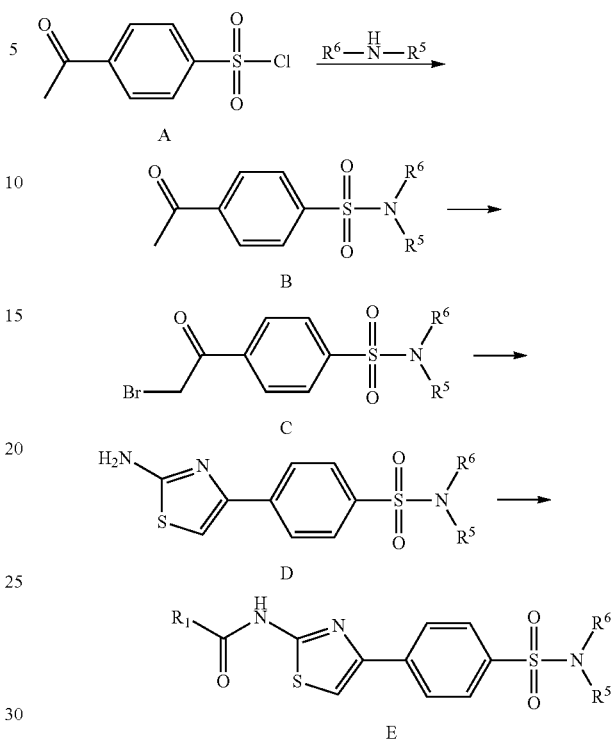

Scheme A

In some embodiments, sulfonyl chloride A is reacted with an amine in the presence of a base (such as DIEA) in a solvent (such as dichloromethane) at room temperature overnight to yield sulfonamides of formula B. Sulfonamides of structure B are brominated to give bromides of general formula C. In some embodiments, sulfonamides of structure B are brominated with for example bromine, HBr 45% solution. A subsequent cyclization reaction with thiourea in the presence of a base at room temperature affords a compound of formula D. In some embodiments, the base is NaHCO$_3$. In some embodiments, a compound of formula D is reacted with an appropriate acid chloride to obtain a compound of formula E.

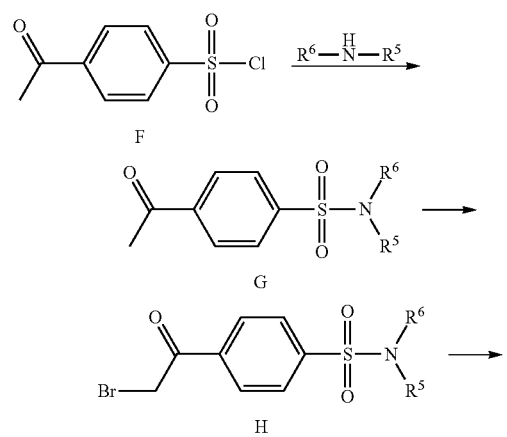

Scheme B

-continued

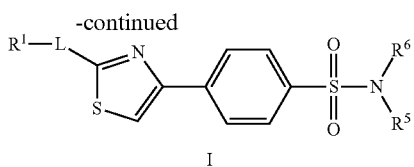

I

In another embodiment, sulfonyl chloride F is reacted with an amine in the presence of a base in a suitable solvent at room temperature to yield a compound of formula G. In some embodiments, the base is N,N-diisopropylethylamine (DIEA). In some embodiments, the suitable solvent is dichloromethane. In some embodiments, compounds G are brominated to give a compound of formula H. In some embodiments, compounds G are brominated with bromine, HBr 45% solution to give a compound of formula H. A subsequent cyclization reaction with the appropriate thioamide in the presence of a suitable base and in a suitable solvent at room temperature affords compounds of general formula I. In some embodiments, the suitable base is $NaHCO_3$. In some embodiments, L is absent. In some embodiments, L is alkylene. In some embodiments, $R^1$ is substituted or unsubstituted aryl. In some embodiments, $R^1$ is substituted phenyl.

It will be understood that the reactions shown above are illustrative.

In one aspect, compounds are synthesized as described in the Examples section.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"Oxo" refers to the =O substituent.

"Thioxo" refers to the =S substituent.

"Alkyl" refers to a straight or branched hydrocarbon chain radical, having from one to twenty carbon atoms, and which is attached to the rest of the molecule by a single bond. An alkyl comprising up to 10 carbon atoms is referred to as a $C_1$-$C_{10}$ alkyl, likewise, for example, an alkyl comprising up to 6 carbon atoms is a $C_1$-$C_6$ alkyl. Alkyls (and other moieties defined herein) comprising other numbers of carbon atoms are represented similarly. Alkyl groups include, but are not limited to, $C_1$-$C_{10}$ alkyl, $C_1$-$C_9$ alkyl, $C_1$-$C_8$ alkyl, $C_1$-$C_7$ alkyl, $C_1$-$C_6$ alkyl, $C_1$-$C_5$ alkyl, $C_1$-$C_4$ alkyl, $C_1$-$C_3$ alkyl, $C_1$-$C_2$ alkyl, $C_2$-$C_8$ alkyl, $C_3$-$C_8$ alkyl and $C_4$-$C_8$ alkyl. Representative alkyl groups include, but are not limited to, methyl, ethyl, n-propyl, 1-methylethyl (i-propyl), n-butyl, i-butyl, s-butyl, n-pentyl, 1,1-dimethylethyl (t-butyl), 3-methylhexyl, 2-methylhexyl, 1-ethyl-propyl, and the like. In some embodiments, the alkyl is methyl, ethyl, s-butyl, or 1-ethyl-propyl. Unless stated otherwise specifically in the specification, an alkyl group may be optionally substituted as described below. "Alkylene" or "alkylene chain" refers to a straight or branched divalent hydrocarbon chain linking the rest of the molecule to a radical group. In some embodiments, the alkylene is —$CH_2$—, —$CH_2CH_2$—, or —$CH_2CH_2CH_2$—. In some embodiments, the alkylene is —$CH_2$—. In some embodiments, the alkylene is —$CH_2CH_2$—. In some embodiments, the alkylene is —$CH_2CH_2CH_2$—.

"Alkoxy" refers to a radical of the formula —OR where R is an alkyl radical as defined. Unless stated otherwise specifically in the specification, an alkoxy group may be optionally substituted as described below. Representative alkoxy groups include, but are not limited to, methoxy, ethoxy, propoxy, butoxy, pentoxy. In some embodiments, the alkoxy is methoxy. In some embodiments, the alkoxy is ethoxy.

"Heteroalkylene" refers to an alkyl radical as described above where one or more carbon atoms of the alkyl is replaced with a 0, N or S atom. "Heteroalkylene" or "heteroalkylene chain" refers to a straight or branched divalent heteroalkyl chain linking the rest of the molecule to a radical group. Unless stated otherwise specifically in the specification, the heteroalkyl or heteroalkylene group may be optionally substituted as described below. Representative heteroalkyl groups include, but are not limited to —$OCH_2OMe$, —$OCH_2CH_2OMe$, or —$OCH_2CH_2OCH_2CH_2NH_2$. Representative heteroalkylene groups include, but are not limited to —$OCH_2CH_2O$—, —$OCH_2CH_2OCH_2CH_2O$—, or —$OCH_2CH_2OCH_2CH_2OCH_2CH_2O$—.

"Alkylamino" refers to a radical of the formula —NHR or —NRR where each R is, independently, an alkyl radical as defined above. Unless stated otherwise specifically in the specification, an alkylamino group may be optionally substituted as described below.

The term "aromatic" refers to a planar ring having a delocalized π-electron system containing 4n+2 π electrons, where n is an integer. Aromatics can be optionally substituted. The term "aromatic" includes both aryl groups (e.g., phenyl, naphthalenyl) and heteroaryl groups (e.g., pyridinyl, quinolinyl).

"Aryl" refers to an aromatic ring wherein each of the atoms forming the ring is a carbon atom. Aryl groups can be optionally substituted. Examples of aryl groups include, but are not limited to phenyl, and naphthalenyl. In some embodiments, the aryl is phenyl. Depending on the structure, an aryl group can be a monoradical or a diradical (i.e., an arylene group). Unless stated otherwise specifically in the specification, the term "aryl" or the prefix "ar-" (such as in "aralkyl") is meant to include aryl radicals that are optionally substituted.

"Carboxy" refers to —$CO_2H$. In some embodiments, carboxy moieties may be replaced with a "carboxylic acid bioisostere", which refers to a functional group or moiety that exhibits similar physical and/or chemical properties as a carboxylic acid moiety. A carboxylic acid bioisostere has similar biological properties to that of a carboxylic acid group. A compound with a carboxylic acid moiety can have the carboxylic acid moiety exchanged with a carboxylic acid bioisostere and have similar physical and/or biological properties when compared to the carboxylic acid-containing compound. For example, in one embodiment, a carboxylic acid bioisostere would ionize at physiological pH to roughly the same extent as a carboxylic acid group. Examples of bioisosteres of a carboxylic acid include, but are not limited to:

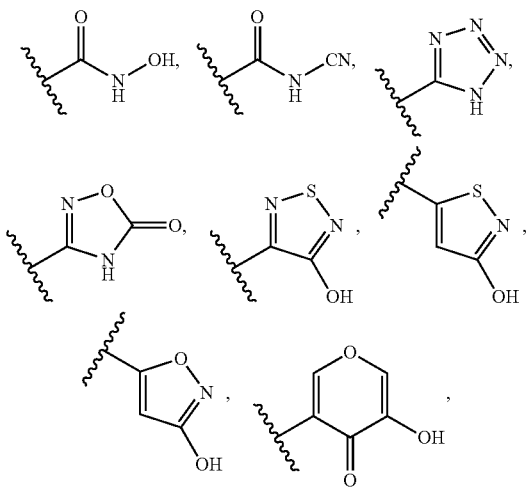

and the like.

"Cycloalkyl" refers to a monocyclic or polycyclic non-aromatic radical, wherein each of the atoms forming the ring (i.e. skeletal atoms) is a carbon atom. Cycloalkyls may be saturated, or partially unsaturated. Cycloalkyls may be fused with an aromatic ring (in which case the cycloalkyl is bonded through a non-aromatic ring carbon atom). Cycloalkyl groups include groups having from 3 to 10 ring atoms. Representative cycloalkyls include, but are not limited to, cycloakyls having from three to ten carbon atoms, from three to eight carbon atoms, from three to six carbon atoms, or from three to five carbon atoms. Monocyclic cycloalkyl radicals include, for example, cyclopropyl, cyclobutyl, cyclopentyl, cyclohexyl, cycloheptyl, and cyclooctyl. In some embodiments, the monocyclic cycloalkyl is cyclopropyl, cyclobutyl, cyclopentyl or cyclohexyl. Polycyclic radicals include, for example, adamantyl, norbornyl, decalinyl, and 3,4-dihydronaphthalen-1(2H)-one. Unless otherwise stated specifically in the specification, a cycloalkyl group may be optionally substituted.

"Fused" refers to any ring structure described herein which is fused to an existing ring structure. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Haloalkoxy" refers to an alkoxy radical, as defined above, that is substituted by one or more halo radicals, as defined above, e.g., trifluoromethoxy, difluoromethoxy, fluoromethoxy, trichloromethoxy, 2,2,2-trifluoroethoxy, 1,2-difluoroethoxy, 3-bromo-2-fluoropropoxy, 1,2-dibromoeth-oxy, and the like. Unless stated otherwise specifically in the specification, a haloalkoxy group may be optionally substituted.

"Heterocycloalkyl" or "heterocyclyl" or "heterocyclic ring" refers to a stable 3- to 14-membered non-aromatic ring radical comprising 2 to 13 carbon atoms and from one to 6 heteroatoms selected from the group consisting of nitrogen, oxygen, and sulfur. Unless stated otherwise specifically in the specification, the heterocycloalkyl radical may be a monocyclic, or bicyclic ring system, which may include fused (when fused with an aryl or a heteroaryl ring, the heterocycloalkyl is bonded through a non-aromatic ring atom) or bridged ring systems. The nitrogen, carbon or sulfur atoms in the heterocyclyl radical may be optionally oxidized. The nitrogen atom may be optionally quaternized. The heterocycloalkyl radical is partially or fully saturated. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl. In some embodiments the heterocycloalkyl is morpholinyl, thiomorpholinyl, piperidinyl, or pyrrolidinyl. In some embodiments the heterocycloalkyl is morpholinyl. The term heterocycloalkyl also includes all ring forms of carbohydrates, including but not limited to monosaccharides, disaccharides and oligosaccharides. Unless otherwise noted, heterocycloalkyls have from 2 to 10 carbons in the ring. In some embodiments, heterocycloalkyls have from 2 to 8 carbons in the ring. In some embodiments, heterocycloalkyls have from 2 to 8 carbons in the ring and 1 or 2 N atoms. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). Unless stated otherwise specifically in the specification, a heterocycloalkyl group may be optionally substituted.

Heteroaryl" refers to an aryl group that includes one or more ring heteroatoms selected from nitrogen, oxygen and sulfur. The heteroaryl is monocyclic or bicyclic. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, furazanyl, indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. Illustrative examples of monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Illustrative examples of bicyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, heteroaryl is pyridinyl, thienyl or furanyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, a bicyclic heteroaryl is a $C_6$-$C_9$heteroaryl.

The term "optionally substituted" or "substituted" means that the referenced group may be substituted with one or more additional group(s) individually and independently selected from alkyl, haloalkyl, cycloalkyl, aryl, heteroaryl, heterocycloalkyl, —OH, alkoxy, aryloxy, alkylthio, arylthio, alkylsulfoxide, arylsulfoxide, alkylsulfone, arylsulfone, —CN, alkyne, $C_1$-$C_6$alkylalkyne, halogen, acyl, acyloxy, —$CO_2H$, —$CO_2$alkyl, nitro, and amino, including mono- and di-substituted amino groups (e.g. —$NH_2$, —NHR, —N(R)$_2$), and the protected derivatives thereof. In some embodiments, optional substituents are independently selected from alkyl, alkoxy, haloalkyl, cycloalkyl, halogen, —CN, —$NH_2$, —NH(CH$_3$), —N(CH$_3$)$_2$, —OH, —$CO_2H$, and —$CO_2$alkyl. In some embodiments, optional substituents are independently selected from fluoro, chloro, bromo, iodo, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic, saturated or unsaturated carbon atoms, excluding aromatic carbon atoms) includes oxo (=O).

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), Formula (Ia), Formula (Ib), Formula (Ic), Formula (Id), Formula (II), Formula (III), Formula (IV), or Formula (V) and a co-agent, are both administered to a patient simultaneously in the form of a single entity or dosage. The term "non-fixed combination" means that the active ingredients, e.g. a compound of Formula (I), Formula (Ia), Formula (Ib), Formula (Ic), Formula (Id), Formula (II), Formula (III), Formula (IV), or Formula (V) and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The term "subject" or "patient" encompasses mammals. Examples of mammals include, but are not limited to, humans. In one embodiment, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

A "tautomer" refers to a proton shift from one atom of a molecule to another atom of the same molecule. The compounds presented herein may exist as tautomers. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH. Some examples of tautomeric interconversions include:

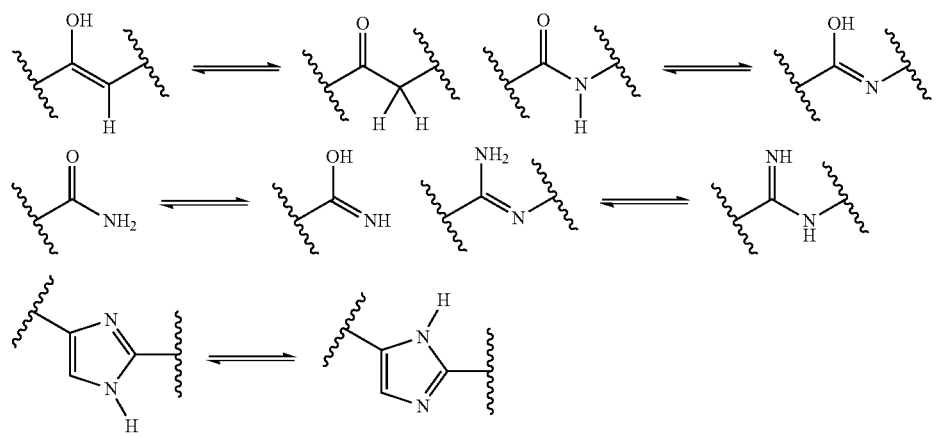

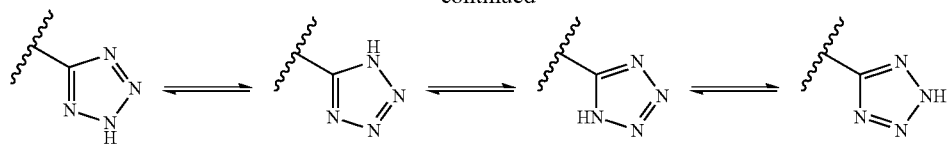

Administration and Pharmaceutical Composition

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

A pharmaceutical composition, as used herein, refers to a mixture of a compound of Formula (I), Formula (Ia), Formula (Ib), Formula (Ic), Formula (Id), Formula (II), Formula (III), Formula (IV), or Formula (V) with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism.

Pharmaceutical formulations described herein are administerable to a subject in a variety of ways by multiple administration routes, including but not limited to, oral, parenteral (e.g., intravenous, subcutaneous, intramuscular, intramedullary injections, intrathecal, direct intraventricular, intraperitoneal, intralymphatic, intranasal injections), intranasal, buccal, topical or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

In some embodiments, the compounds of Formula (I), Formula (Ia), Formula (Ib), Formula (Ic), Formula (Id), Formula (II), Formula (III), Formula (IV), or Formula (V) are administered orally.

In some embodiments, the compounds of Formula (I), Formula (Ia), Formula (Ib), Formula (Ic), Formula (Id), Formula (II), Formula (III), Formula (IV), or Formula (V) are administered topically. In such embodiments, the compound of Formula (I), Formula (Ia), Formula (Ib), Formula (Ic), Formula (Id), Formula (II), Formula (III), Formula (IV), or Formula (V) is formulated into a variety of topically administrable compositions, such as solutions, suspensions, lotions, gels, pastes, shampoos, scrubs, rubs, smears, medicated sticks, medicated bandages, balms, creams or ointments. In one aspect, the compounds of Formula (I), Formula (Ia), Formula (Ib), Formula (Ic), Formula (Id), Formula (II), Formula (III), Formula (IV), or Formula (V) are administered topically to the skin.

In another aspect, the compounds of Formula (I), Formula (Ia), Formula (Ib), Formula (Ic), Formula (Id), Formula (II), Formula (III), Formula (IV), or Formula (V) are administered by inhalation.

In another aspect, the compounds of Formula (I), Formula (Ia), Formula (Ib), Formula (Ic), Formula (Id), Formula (II), Formula (III), Formula (IV), or Formula (V) are formulated for intranasal adminstration. Such formulations include nasal sprays, nasal mists, and the like.

In another aspect, the compounds of Formula (I), Formula (Ia), Formula (Ib), Formula (Ic), Formula (Id), Formula (II), Formula (III), Formula (IV), or Formula (V) are formulated as eye drops.

In any of the aforementioned aspects are further embodiments in which the effective amount of the compound of Formula (I), Formula (Ia), Formula (Ib), Formula (Ic), Formula (Id), Formula (II), Formula (III), Formula (IV), or Formula (V) is: (a) systemically administered to the mammal; and/or (b) administered orally to the mammal; and/or (c) intravenously administered to the mammal; and/or (d) administered by inhalation to the mammal; and/or (e) administered by nasal administration to the mammal; or and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which (i) the compound is administered once; (ii) the compound is administered to the mammal multiple times over the span of one day; (iii) continually; or (iv) continuously.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain embodiments, a compound as described herein is administered in a local rather than systemic manner.

In some embodiments, the compound described herein is administered topically. In some embodiments, the compound described herein is administered systemically.

In some embodiments, the pharmaceutical formulation is in the form of a tablet. In other embodiments, pharmaceutical formulations of the compounds of Formula (I), Formula (Ia), Formula (Ib), Formula (Ic), Formula (Id), Formula (II), Formula (III), Formula (IV), or Formula (V) are in the form of a capsule.

In one aspect, liquid formulation dosage forms for oral administration are in the form of aqueous suspensions or solutions selected from the group including, but not limited to, aqueous oral dispersions, emulsions, solutions, elixirs, gels, and syrups.

For administration by inhalation, a compound of Formula (I), Formula (Ia), Formula (Ib), Formula (Ic), Formula (Id), Formula (II), Formula (III), Formula (IV), or Formula (V) is formulated for use as an aerosol, a mist or a powder.

For buccal or sublingual administration, the compositions may take the form of tablets, lozenges, or gels formulated in a conventional manner.

In some embodiments, compounds of Formula (I), Formula (Ia), Formula (Ib), Formula (Ic), Formula (Id), Formula (II), Formula (III), Formula (IV), or Formula (V) are prepared as transdermal dosage forms.

In one aspect, a compound of Formula (I), Formula (Ia), Formula (Ib), Formula (Ic), Formula (Id), Formula (II), Formula (III), Formula (IV), or Formula (V) is formulated into a pharmaceutical composition suitable for intramuscular, subcutaneous, or intravenous injection.

In some embodiments, the compounds described herein may be administered topically and can be formulated into a variety of topically administrable compositions, such as solutions, suspensions, lotions, gels, pastes, medicated sticks, balms, creams or ointments.

In some embodiments, the compounds of Formula (I), Formula (Ia), Formula (Ib), Formula (Ic), Formula (Id), Formula (II), Formula (III), Formula (IV), or Formula (V) are formulated in rectal compositions such as enemas, rectal gels, rectal foams, rectal aerosols, suppositories, jelly suppositories, or retention enemas.

Methods of Dosing and Treatment Regimens

In one embodiment, the compounds of Formula (I), Formula (Ia), Formula (Ib), Formula (Ic), Formula (Id), Formula (II), Formula (III), Formula (IV), or Formula (V) are used in the preparation of medicaments for the treatment of diseases or conditions described herein. In addition, a method for treating any of the diseases or conditions described herein in a subject in need of such treatment, involves administration of pharmaceutical compositions that include at least one compound of Formula (I), Formula (Ia), Formula (Ib), Formula (Ic), Formula (Id), Formula (II), Formula (III), Formula (IV), or Formula (V) or a pharmaceutically acceptable salt, active metabolite, prodrug, or solvate thereof, in therapeutically effective amounts to said subject.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation clinical trial.

In prophylactic applications, compositions containing the compounds described herein are administered to a patient susceptible to or otherwise at risk of a particular disease, disorder or condition.

In certain embodiments, the dose of drug being administered may be temporarily reduced or temporarily suspended for a certain length of time (i.e., a "drug holiday").

Doses employed for adult human treatment are typically in the range of 0.01 mg-5000 mg per day or from about 1 mg to about 1000 mg per day. In one embodiment, the desired dose is conveniently presented in a single dose or in divided doses.

Combination Treatments

In certain instances, it is appropriate to administer at least one compound of Formula (I), Formula (Ia), Formula (Ib), Formula (Ic), Formula (Id), Formula (II), Formula (III), Formula (IV), or Formula (V) in combination with another therapeutic agent.

In one specific embodiment, a compound of Formula (I), Formula (Ia), Formula (Ib), Formula (Ic), Formula (Id), Formula (II), Formula (III), Formula (IV), or Formula (V) is co-administered with a second therapeutic agent, wherein the compound of Formula (I), Formula (Ia), Formula (Ib), Formula (Ic), Formula (Id), Formula (II), Formula (III), Formula (IV), or Formula (V) and the second therapeutic agent modulate different aspects of the disease, disorder or condition being treated, thereby providing a greater overall benefit than administration of either therapeutic agent alone.

For combination therapies described herein, dosages of the co-administered compounds vary depending on the type of co-drug(s) employed, on the specific drug(s) employed, on the disease or condition being treated and so forth. In additional embodiments, when co-administered with one or more other therapeutic agents, the compound provided herein is administered either simultaneously with the one or more other therapeutic agents, or sequentially.

If administration is simultaneous, the multiple therapeutic agents are, by way of example only, provided in a single, unified form, or in multiple forms.

In some embodiments, compounds of Formula (I), Formula (Ia), Formula (Ib), Formula (Ic), Formula (Id), Formula (II), Formula (III), Formula (IV), or Formula (V) are administered to a mammal in combination with one or more additional antiviral agent.

In some embodiments, the additional antiviral agent is a fusion inhibitor, integrase inhibitor, nucleoside analogues, protease inhibitor, reverse transcriptase inhibitor, synergistic enhancer or antiretroviral.

In some embodiments, the additional antiviral agent is selected from Abacavir, Acyclovir, Adefovir, Amantadine, Amprenavir, Ampligen, Arbidol, Atazanavir, Atripla, Balavir, Boceprevirertet, Cidofovir, Combivir, Dolutegravir, Darunavir, Delavirdine, Didanosine, Docosanol, Edoxudine, Efavirenz, Emtricitabine, Enfuvirtide, Entecavir, Ecoliever, Famciclovir, Fomivirsen, Fosamprenavir, Foscarnet, Fosfonet, Ganciclovir, Ibacitabine, Imunovir, Idoxuridine, Imiquimod, Indinavir, Inosine, Interferon type III, Interferon type II, Interferon type I, Interferon, Lamivudine, Lopinavir, Loviride, Maraviroc, Moroxydine, Methisazone, Nelfinavir, Nevirapine, Nexavir, Oseltamivir, Peginterferon alfa-2a, Penciclovir, Peramivir, Pleconaril, Podophyllotoxin, Raltegravir, Ribavirin, Rimantadine, Ritonavir, Pyramidine, Saquinavir, Sofosbuvir, Stavudine, Tea tree oil, Telaprevir, Tenofovir, Tenofovir disoproxil, Tipranavir, Trifluridine, Trizivir, Tromantadine, Truvada, traporved, Valaciclovir, Valganciclovir, Vicriviroc, Vidarabine, Viramidine, Zalcitabine, Zanamivir, and Zidovudine.

In some embodiments, compounds of Formula (I), Formula (Ia), Formula (Ib), Formula (Ic), Formula (Id), Formula (II), Formula (III), Formula (IV), or Formula (V) are administered to a mammal in combination with one or more additional antibacterial agent.

In some embodiments, the additional antibacterial agent is an aminoglycoside, ansamycin, carbacephem, carbapenem, cephalosporin, glycopeptides, lincosamide, lipopeptide, macrolide, monobactam, nitrofuran, oxazolidinone, penicillin, polypeptides, quinolone, fluoroquinolone, sulfonamide, tetracycline, or a drug against mycobacteria.

In some embodiments, the additional antibacterial agent is Amikacin, Gentamicin, Kanamycin, Neomycin, Netilmicin, Tobramycin, Paromomycin, Streptomycin, Spectinomycin, Geldanamycin, Herbimycin, Rifaximin, Loracarbef, Ertapenem, Doripenem Doribax, Imipenem, Meropenem Merrem, Cefadroxil, Cefazolin, Cefalotin, Cefalexin, Cefaclor, Cefamandole, Cefoxitin, Cefprozil, Cefuroxime, Cefixime, Cefdinir, Cefditoren, Cefoperazone, Cefotaxime, Cefpodoxime, Ceftazidime, Ceftibuten, Ceftizoxime, Ceftriaxone, Cefepime, Ceftaroline, Ceftobiprole, Teicoplanin, Vancomycin, Televancin, Dalbavancin, Oritavancin, Clindamycin, Lincomycin, Daptomycin, Azithromycin, Clarithromycin, Dirithromycin, Erythromycin, Roxithromycin, Troleandomycin, Telithromycin, Spiramycin, Aztreonam, Furazolidone, Nitrofurantoin, Linezolid, Posizolid, Radezolid, Torezolid, Amoxicillin, Ampicillin, Azlocillin, Flucloxacillin, Bacitracin, Colistin, Polymyxin B, Ciprofloxacin, Enoxacin, Gatifloxacin, Gemifloxacin, Levofloxacin, Lomefloxacin, Moxifloxacin, Nalidixic acid, Norfloxacin, Ofloxacin, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole, Sulfonamidochrysoidine, Demeclocycline, Doxycycline, Minocycline, Oxytetracycline, Clofazimine, Dapsone, Capreomycin, Cycloserine, Ethambutol, Ethionamide, Pyrazinamide, Rifapentine, Arsphenamine, ChloramphenicolFosfomycin Fusidic acid, Metronidazole., Mupirocin, Platensimycin, Quinupristin, Thiamphenicol Tigecycline, or Trimethoprim.

In some embodiments, compounds of Formula (I), Formula (Ia), Formula (Ib), Formula (Ic), Formula (Id), Formula (II), Formula (III), Formula (IV), or Formula (V), are administered in combination with one or more additional anti-cancer agent.

In some embodiments, the additional anti-cancer agent is a chemotherapeutic agent, a steroid, an immunotherapeutic agent, a targeted therapy, or a combination thereof. In some embodiments, the additional therapeutic agent is a B cell receptor pathway inhibitor. In some embodiments, the B cell receptor pathway inhibitor is a CD79A inhibitor, a CD79B inhibitor, a CD19 inhibitor, a Lyn inhibitor, a Syk inhibitor, a PI3K inhibitor, a Blnk inhibitor, a PLCγ inhibitor, a PKCβ inhibitor, or a combination thereof. In some embodiments, the additional therapeutic agent is an antibody, B cell receptor signaling inhibitor, a PI3K inhibitor, an IAP inhibitor, an mTOR inhibitor, a radioimmunotherapeutic, a DNA damaging agent, a proteosome inhibitor, a histone deacetylase inhibitor, a protein kinase inhibitor, a hedgehog inhibitor, an Hsp90 inhibitor, a telomerase inhibitor, a Jak1/2 inhibitor, a protease inhibitor, a PKC inhibitor, a PARP inhibitor, or a combination thereof.

In some embodiments, the additional anti-cancer agent comprises an agent selected from: an inhibitor of LYN, SYK, JAK, PI3K, PLCγ, MAPK, MEK or NFκB.

In some embodiments, the additional anti-cancer agent comprises an agent selected from: bendamustine, bortezomib, lenalidomide, idelalisib (GS-1101), vorinostat, ofatumumab, everolimus, panobinostat, temsirolimus, romidepsin, vorinostat, fludarabine, cyclophosphamide, mitoxantrone, pentostatine, prednisone, etopside, procarbazine, and thalidomide.

In some embodiments the additional anti-cancer agent comprises radioimmunotherapy with $^{90}$Y-ibritumomab tiuxetan or $^{131}$I-tositumomab.

In some embodiments, the additional anti-cancer agent is an autologous stem cell transplant.

In some embodiments, the additional anti-cancer agent is selected from: Nitrogen Mustards such as for example, bendamustine, chlorambucil, chlormethine, cyclophosphamide, ifosfamide, melphalan, prednimustine, trofosfamide; Alkyl Sulfonates like busulfan, mannosulfan, treosulfan; Ethylene Imines like carboquone, thiotepa, triaziquone; Nitrosoureas like carmustine, fotemustine, lomustine, nimustine, ranimustine, semustine, streptozocin; Epoxides such as for example, etoglucid; other Alkylating Agents such as for example dacarbazine, mitobronitol, pipobroman, temozolomide; Folic Acid Analogues such as for example methotrexate, permetrexed, pralatrexate, raltitrexed; Purine Analogs such as for example cladribine, clofarabine, fludarabine, mercaptopurine, nelarabine, tioguanine; Pyrimidine Analogs such as for example azacitidine, capecitabine, carmofur, cytarabine, decitabine, fluorouracil, gemcitabine, tegafur; Vinca Alkaloids such as for example vinblastine, vincristine, vindesine, vinflunine, vinorelbine; Podophyllotoxin Derivatives such as for example etoposide, teniposide; Colchicine derivatives such as for example demecolcine; Taxanes such as for example docetaxel, paclitaxel, paclitaxel poliglumex; Other Plant Alkaloids and Natural Products such as for example trabectedin; Actinomycines such as for example dactinomycin; Antracyclines such as for example aclarubicin, daunorubicin, doxorubicin, epirubicin, idarubicin, mitoxantrone, pirarubicin, valrubicin, zorubincin; Other Cytotoxic Antibiotics such as for example bleomycin, ixabepilone, mitomycin, plicamycin; Platinum Compounds such as for example carboplatin, cisplatin, oxaliplatin, satraplatin; Methylhydrazines such as for example procarbazine; Sensitizers such as for example aminolevulinic acid, efaproxiral, methyl aminolevulinate, porfimer sodium, temoporfin; Protein Kinase Inhibitors such as for example dasatinib, erlotinib, everolimus, gefitinib, imatinib, lapatinib, nilotinib, pazonanib, sorafenib, sunitinib, temsirolimus; Other Antineoplastic Agents such as for example alitretinoin, altretamine, amzacrine, anagrelide, arsenic trioxide, asparaginase, bexarotene, bortezomib, celecoxib, denileukin diftitox, estramustine, hydroxycarbamide, irinotecan, lonidamine, masoprocol, miltefosein, mitoguazone, mitotane, oblimersen, pegaspargase, pentostatin, romidepsin, sitimagene ceradenovec, tiazofurine, topotecan, tretinoin, vorinostat; Estrogens such as for example diethylstilbenol, ethinylestradiol, fosfestrol, polyestradiol phosphate; Progestogens such as for example gestonorone, medroxyprogesterone, megestrol; Gonadotropin Releasing Hormone Analogs such as for example buserelin, goserelin, leuprorelin, triptorelin; Anti-Estrogens such as for example fulvestrant, tamoxifen, toremifene; Anti-Androgens such as for example bicalutamide, flutamide, nilutamide, Enzyme Inhibitors, aminoglutethimide, anastrozole, exemestane, formestane, letrozole, vorozole; Other Hormone Antagonists such as for example abarelix, degarelix; Immunostimulants such as for example histamine dihydrochloride, mifamurtide, pidotimod, plerixafor, roquinimex, thymopentin; Immunosuppressants such as for example everolimus, gusperimus, leflunomide, mycophenolic acid, sirolimus; Calcineurin Inhibitors such as for example ciclosporin, tacrolimus; Other Immunosuppressants such as for example azathioprine, lenalidomide, methotrexate, thalidomide; and Radiopharmaceuticals such as for example, iobenguane.

In some embodiments, the additional anti-cancer agent is selected from: interferons, interleukins, Tumor Necrosis Factors, Growth Factors, or the like.

In some embodiments, the additional anti-cancer agent is selected from: ancestim, filgrastim, lenograstim, molgramostim, pegfilgrastim, sargramostim; Interferons such as for example interferon alfa natural, interferon alfa-2a, interferon alfa-2b, interferon alfacon-1, interferon alfa-n1, interferon beta natural, interferon beta-1a, interferon beta-1b, interferon gamma, peginterferon alfa-2a, peginterferon alfa-2b; Interleukins such as for example aldesleukin, oprelvekin; Other Immunostimulants such as for example BCG vaccine, glatiramer acetate, histamine dihydrochloride, immunocyanin, lentinan, melanoma vaccine, mifamurtide, pegademase, pidotimod, plerixafor, poly I:C, poly ICLC, roquinimex, tasonermin, thymopentin; Immunosuppressants such as for example abatacept, abetimus, alefacept, antilymphocyte immunoglobulin (horse), antithymocyte immunoglobulin (rabbit), eculizumab, efalizumab, everolimus, gusperimus, leflunomide, muromab-CD3, mycophenolic acid, natalizumab, sirolimus; TNF alpha Inhibitors such as for example adalimumab, afelimomab, certolizumab pegol, etanercept, golimumab, infliximab; Interleukin Inhibitors such as for example anakinra, basiliximab, canakinumab, daclizumab, mepolizumab, rilonacept, tocilizumab, ustekinumab; Calcineurin Inhibitors such as for example ciclosporin, tacrolimus; Other Immunosuppressants such as for example azathioprine, lenalidomide, methotrexate, thalidomide.

In some embodiments, the additional anti-cancer agent is selected from: Monoclonal Antibodies such as for example alemtuzumab, bevacizumab, catumaxomab, cetuximab, edrecolomab, gemtuzumab, ofatumumab, panitumumab, rituximab, trastuzumab; Immunosuppressants, eculizumab, efalizumab, muromab-CD3, natalizumab; TNF alpha Inhibitors such as for example adalimumab, afelimomab, certolizumab pegol, golimumab, infliximab; Interleukin Inhibitors, basiliximab, canakinumab, daclizumab, mepolizumab, tocilizumab, ustekinumab; Radiopharmaceuticals, ibritumomab tiuxetan, tositumomab; Others Monoclonal Antibodies such as for example abagovomab, adecatumumab, alemtuzumab, anti-CD30 monoclonal antibody Xmab2513, anti-MET monoclonal antibody MetMab, apolizumab, apomab, arcitumomab, basiliximab, bispecific antibody 2B1, blinatumomab, brentuximab vedotin, capromab pendetide, cixutumumab, claudiximab, conatumumab, dacetuzumab, denosumab, eculizumab, epratuzumab, epratuzumab, ertumaxomab, etaracizumab, figitumumab, fresolimumab, galiximab, ganitumab, gemtuzumab ozogamicin, glembatumumab, ibritumomab, inotuzumab ozogamicin, ipilimumab, lexatumumab, lintuzumab, lintuzumab, lucatumumab, mapatumumab, matuzumab, milatuzumab, monoclonal antibody CC49, necitumumab, nimotuzumab, ofatumumab, oregovomab, pertuzumab, ramacurimab, ranibizumab, siplizumab, sonepcizumab, tanezumab, tositumomab, trastuzumab, tremelimumab, tucotuzumab celmoleukin, veltuzumab, visilizumab, volociximab, zalutumumab.

In some embodiments, the additional anti-cancer agent is selected from: agents that affect the tumor micro-environment such as cellular signaling network (e.g. phosphatidylinositol 3-kinase (PI3K) signaling pathway, signaling from the B-cell receptor and the IgE receptor). In some embodiments, the additional therapeutic agent is a PI3K signaling inhibitor or a syc kinase inhibitor. In one embodiment, the syk inhibitor is R788. In another embodiment is a PKCγ inhibitor such as by way of example only, enzastaurin.

Examples of agents that affect the tumor micro-environment include PI3K signaling inhibitor, syc kinase inhibitor, Protein Kinase Inhibitors such as for example dasatinib, erlotinib, everolimus, gefitinib, imatinib, lapatinib, nilotinib, pazonanib, sorafenib, sunitinib, temsirolimus; Other Angiogenesis Inhibitors such as for example GT-111, JI-101, R1530; Other Kinase Inhibitors such as for example AC220, AC480, ACE-041, AMG 900, AP24534, Any-614, AT7519, AT9283, AV-951, axitinib, AZD1152, AZD7762, AZD8055, AZD8931, bafetinib, BAY 73-4506, BGJ398, BGT226, BI 811283, BI6727, BIBF 1120, BIBW 2992, BMS-690154, BMS-777607, BMS-863233, BSK-461364, CAL-101, CEP-11981, CYC116, DCC-2036, dinaciclib, dovitinib lactate, E7050, EMD 1214063, ENMD-2076, fostamatinib disodium, GSK2256098, GSK690693, INCB18424, INNO-406, JNJ-26483327, JX-594, KX2-391, linifanib, LY2603618, MGCD265, MK-0457, MK1496, MLN8054, MLN8237, MP470, NMS-1116354, NMS-1286937, ON 01919.Na, OSI-027, OSI-930, Btk inhibitor, PF-00562271, PF-02341066, PF-03814735, PF-04217903, PF-04554878, PF-04691502, PF-3758309, PHA-739358, PLC3397, progenipoietin, R547, R763, ramucirumab, regorafenib, R05185426, SAR103168, SCH 727965, SGI-1176, SGX523, SNS-314, TAK-593, TAK-901, TKI258, TLN-232, TTP607, XL147, XL228, XL281R05126766, XL418, XL765.

In some embodiments, the additional anti-cancer agent is selected from inhibitors of mitogen-activated protein kinase signaling, e.g., U0126, PD98059, PD184352, PD0325901, ARRY-142886, SB239063, SP600125, BAY 43-9006, wortmannin, or LY294002; Syk inhibitors; mTOR inhibitors; and antibodies (e.g., rituxan).

In some embodiments, the additional anti-cancer agent is selected from: Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ibrutinib; ifosfamide; iimofosine; interleukin Il (including recombinant interleukin II, or rIL2), interferon alfa-2a; interferon alfa-2b; interferon alfa-n1; interferon alfa-n3; interferon beta-1 a; interferon gamma-1 b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride.

In some embodiments, the additional anti-cancer agent is selected from: 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; betaalethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclixiimab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-such as for example growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer.

In some embodiments, the additional anti-cancer agent is selected from: alkylating agents, antimetabolites, natural products, or hormones, e.g., nitrogen mustards (e.g., mechloroethamine, cyclophosphamide, chlorambucil, etc.), alkyl sulfonates (e.g., busulfan), nitrosoureas (e.g., carmustine, lomusitne, etc.), or triazenes (decarbazine, etc.). Examples of antimetabolites include but are not limited to folic acid analog (e.g., methotrexate), or pyrimidine analogs (e.g., Cytarabine), purine analogs (e.g., mercaptopurine, thioguanine, pentostatin).

In some embodiments, the additional anti-cancer agent is selected from: nitrogen mustards (e.g., mechloroethamine, cyclophosphamide, chlorambucil, meiphalan, etc.), ethylenimine and methylmelamines (e.g., hexamethlymelamine, thiotepa), alkyl sulfonates (e.g., busulfan), nitrosoureas (e.g., carmustine, lomusitne, semustine, streptozocin, etc.), or triazenes (decarbazine, etc.). Examples of antimetabolites include, but are not limited to folic acid analog (e.g., methotrexate), or pyrimidine analogs (e.g., fluorouracil, floxouridine, Cytarabine), purine analogs (e.g., mercaptopurine, thioguanine, pentostatin.

In some embodiments, the additional anti-cancer agent is selected from: agents which act by arresting cells in the G2-M phases due to stabilized microtubules, e.g., Erbulozole (also known as R-55104), Dolastatin 10 (also known as DLS-10 and NSC-376128), Mivobulin isethionate (also known as CI-980), Vincristine, NSC-639829, Discodermolide (also known as NVP-XX-A-296), ABT-751 (Abbott, also known as E-7010), Altorhyrtins (such as Altorhyrtin A and Altorhyrtin C), Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (also known as LU-103793 and NSC-D-669356), Epothilones (such as Epothilone A, Epothilone B, Epothilone C (also known as desoxyepothilone A or dEpoA), Epothilone D (also referred to as KOS-862, dEpoB, and desoxyepothilone B), Epothilone E, Epothilone F, Epothilone B N-oxide, Epothilone A N-oxide, 16-aza-epothilone B, 21-aminoepothilone B (also known as BMS-310705), 21-hydroxyepothilone D (also known as Desoxyepothilone F and dEpoF), 26-fluoroepothilone), Auristatin PE (also known as NSC-654663), Soblidotin (also known as TZT-1027), LS-4559-P (Pharmacia, also known as LS-4577), LS-4578 (Pharmacia, also known as LS-477-P), LS-4477 (Pharmacia), LS-4559 (Pharmacia), RPR-112378 (Aventis), Vincristine sulfate, DZ-3358 (Daiichi), FR-182877 (Fujisawa, also known as WS-9885B), GS-164 (Takeda), GS-198 (Takeda), KAR-2 (Hungarian Academy of Sciences), BSF-223651 (BASF, also known as ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (also known as LY-355703), AC-7739 (Ajinomoto, also known as AVE-8063A and CS-39.HCl), AC-7700 (Ajinomoto, also known as AVE-8062, AVE-8062A, CS-39-L-Ser.HCl, and RPR-258062A), Vitilevuamide, Tubulysin A, Canadensol, Centaureidin (also known as NSC-106969), T-138067 (Tularik, also known as T-67, TL-138067 and TI-138067), COBRA-1 (Parker Hughes Institute, also known as DDE-261 and WHI-261), H10 (Kansas State University), H16 (Kansas State University), Oncocidin A1 (also known as BTO-956 and DIME), DDE-313 (Parker Hughes Institute), Fijianolide B, Laulimalide, SPA-2 (Parker Hughes Institute), SPA-1 (Parker Hughes Institute, also known as SPIKET-P), 3-IAABU (Cytoskeleton/Mt. Sinai School of Medicine, also known as MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, also known as MF-191), TMPN (Arizona State University), Vanadocene acetylacetonate, T-138026 (Tularik), Monsatrol, Inanocine (also known as NSC-698666), 3-1AABE (Cytoskeleton/Mt. Sinai School of Medicine), A-204197 (Abbott), T-607 (Tuiarik, also known as T-900607), RPR-115781 (Aventis), Eleutherobins (such as Desmethyleleutherobin, Desaetyleleutherobin, lsoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI-2350 (Nereus), Taccalonolide A, TUB-245 (Aventis), A-259754 (Abbott), Diozostatin, (–)-Phenylahistin (also known as NSCL-96F037), D-68838 (Asta Medica), D-68836 (Asta Medica), Myoseverin B, D-43411 (Zentaris, also known as D-81862), A-289099 (Abbott), A-318315 (Abbott), HTI-286 (also known as SPA-110, trifluoroacetate salt) (Wyeth), D-82317 (Zentaris), D-82318 (Zentaris), SC-12983 (NCI), Resverastatin phosphate sodium, BPR-OY-007 (National Health Research Institutes), and SSR-250411 (Sanofi).

EXAMPLES

The following examples are intended to illustrate but not limit the disclosed embodiments.

Example 1: 2-Ethyl-N-(4-(4-(morpholinosulfonyl)phenyl)thiazol-2-yl)butanamide (Compound 16)

Step 1: Preparation of 1-(4-(morpholinosulfonyl)phenyl)ethanone

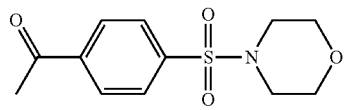 [SMILES: CC(=O)c1ccc(S(=O)(=O)N2CCOCC2)cc1]

4-Acetylbenzenesufonyl chloride (3.5 g, 16 mmol) and 3 ml of DIPEA were dissolved in 100 ml of dichloromethane. To the resulting mixture was added morpholine (4.0 mL, 46 mmol) and the reaction was stirred at room temperature overnight. When the reaction was determined to be complete by HPLC, the reaction mixture was concentrated under reduced pressure. The resulting oil was chromatographed on silica gel and eluted with ethyl acetate and dichloromethane (0:100 to 30:70 gradient) to yield 3.4 g of the title compound (78% yield). MS (EI) m/z 270 (M+1).

Step 2: Preparation of 2-Bromo-1-(4-(morpholinosulfonyl)phenyl)ethanone

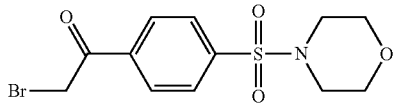 [SMILES: O=C(CBr)c1ccc(S(=O)(=O)N2CCOCC2)cc1]

1-(4-(Morpholinosulfonyl)phenyl)ethanone (3.4 g, 12.6 mmol) and 3 drops of HBr 45% solution were dissolved in 100 ml of chloroform in an ice-water bath. To the resulting mixture was added dropwise bromine (0.64 ml, 12.4 mmol) in 5 mL of chloroform and the reaction was stirred overnight, gradually warming to room temperature. When the reaction was determined to be complete by HPLC, the reaction mixture was washed with a saturated sodium thiosulfate solution and separated. The organic layer was dried and concentrated under reduced pressure. The resulting oil was chromatographed on silica gel and eluted with ethyl acetate and dichloromethane (0:100 to 30:70 gradient) to yield 2.6 g of the title compound (60% yield). MS (EI) m/z 350 (M+1). $^1$H NMR (400 MHz, CDCl$_3$) δ (ppm) 3.04 (m, 4H), 3.75 (m, 4H), 4.45 (m, 2H), 7.87 (d, 2H), 8.15 (d, 2H).

Step 3: Preparation of 4-(4-(Morpholinosulfonyl)phenyl)thiazol-2-amine

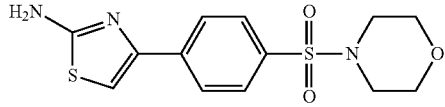 [SMILES: Nc1nc(-c2ccc(S(=O)(=O)N3CCOCC3)cc2)cs1]

2-Bromo-1-(4-(morpholinosulfonyl)phenyl)ethanone (2.6 g, 7.4 mmol) and sodium bicarbonate (1.3 g, 16 mmol) were mixed in 100 mL of dry THF. To the resulting mixture was added thiourea (1.0 g, 13 mmol) and the reaction was stirred at room temperature overnight. When the reaction was determined to be complete by HPLC, the reaction mixture was concentrated under reduced pressure. The residue was dissolved in dichloromethane and washed with water. The organic layer was dried and concentrated in vacuo. The residue was chromatographed on silica gel eluting with ethyl acetate and dichloromethane (0:100 to 40:60 gradient) to yield 2.0 g of the title compound (83% yield). $^1$H NMR (400 MHz, DMSO-d$_6$) δ (ppm) 2.86 (m, 4H), 3.62 (m, 4H), 7.18 (s, 2H), 7.30 (s, 1H), 7.70 (d, 2H), 8.03 (d, 2H). $^{13}$C NMR (400 MHz, DMSO-d6) δ (ppm) 39.9, 65.2, 105.0, 126.1, 128.1, 132.4, 139.2, 148.1, 168.5. MS (EI) m/z 326 (M+1).

Step 4: Preparation of 2-Ethyl-N-(4-(4-(morpholinosulfonyl)phenyl)thiazol-2-yl)butanamide

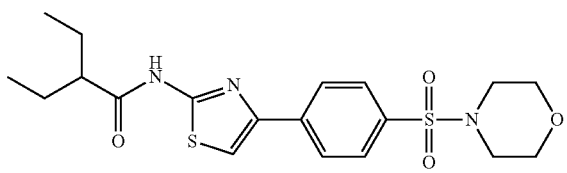 [SMILES: CCC(CC)C(=O)Nc1nc(-c2ccc(S(=O)(=O)N3CCOCC3)cc2)cs1]

4-(4-(Morpholinosulfonyl)phenyl)thiazol-2-amine (0.5 g, 1.5 mmol) and 1.0 mL of dry pyridine were dissolved in dry dichloromethane (50 mL). To the resulting mixture was added 2-ethylbutyryl chloride (0.5 mL, 3.7 mmol) and the reaction heated under reflux at 60° C. overnight. When the reaction was determined to be complete by HPLC, the reaction mixture was cooled to room temperature and concentrated under reduced pressure. The resulting oil was chromatographed on silica gel and eluted with ethyl acetate and dichloromethane (0:100 to 20:80 gradient) to yield 0.42 g of the title compound (65% yield). $^1$H NMR (400 MHz, CDCl$_3$) δ (ppm) 0.91 (m, 6H), 1.61 (m, 2H), 1.71 (m, 2H), 2.20 (m, 1H), 3.04 (m, 4H), 3.75 (m, 4H), 7.33 (s, 1H), 7.85 (d, 2H), 8.02 (d, 2H), 9.57 (s, 1H). $^{13}$C NMR (100 MHz, CDCl$_3$) δ (ppm) 11.9, 25.5, 46.0, 50.9, 66.1, 110.6, 126.5, 128.4, 133.9, 138.8, 147.7, 158.3, 174.2. MS (EI) m/z 424 (M+1).

Example 2: Preparation of (S)—N-(4-(4-(N,N-Diethylsulfamoyl)phenyl)thiazol-2-yl)-2-methylbutanamide (Compound 56)

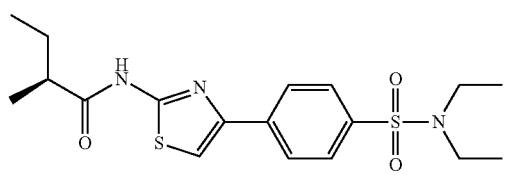 [SMILES: CC[C@H](C)C(=O)Nc1nc(-c2ccc(S(=O)(=O)N(CC)CC)cc2)cs1]

Prepared in a similar manner as described in Example 1. $^1$H NMR (400 MHz, CDCl$_3$) δ (ppm): 9.18 (s, 1H), 7.94 (d, 2H), 7.88 (d, 2H), 7.28 (s, 1H), 3.26 (qd, 4H), 2.43 (m, 1H), 1.78 (m, 1H) 1.58 (m, 1H), 1.26 (dd, 3H), 1.13 (td, 6H), 0.95 (td, 3H). $^{13}$C NMR (100 MHz, CDCl$_3$) δ (ppm): 174.85, 158.43, 147.93, 139.09, 138.15, 127.58, 126.43, 110.09, 42.58, 42.01, 27.10, 16.87, 14.07, 11.67. HRMS (ESI): m/z calcd for $C_{18}H_{25}N_3O_3S_2$ 395.54. found (M+H)$^+$ 396.14.

Compounds 14, 17, 18, 19, 20, 21, 22, 23, 24, 25, 26, 28, 29, 30, 31, 32, 33, 34, 35, 36, 37, 38, 39, 40, 41, 42, 43, 44, 45, 46, 47, 49, 50, 51, 52, 53, 54, 55, 57, 58, 59, 60, 61, 117 and 118 were also prepared in a similar manner as described in Example 1.

Example 3: Preparation of Compound 82

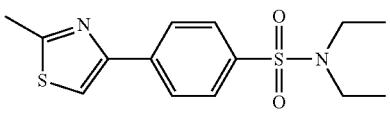 [SMILES: CCN(CC)S(=O)(=O)c1ccc(-c2csc(C)n2)cc1]

Prepared in a similar manner as described in Example 1.
$^1$H NMR (400 MHz, CDCl$_3$) δ (ppm): 7.97 (d, 2H), 7.81 (d, 2H), 7.43 (s, 1H), 3.23 (q, 4H), 2.76 (s, 3H), 1.10 (t, 6H). $^{13}$C NMR (100 MHz, CDCl$_3$) δ (ppm): 167.10, 152.85, 139.64, 137.41, 127.54, 126.81, 114.69, 41.96, 19.11, 14.06.

Example 4: Preparation of Compound 100

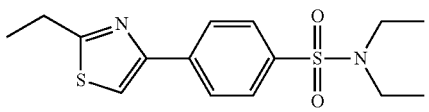 [SMILES: CCc1nc(-c2ccc(S(=O)(=O)N(CC)CC)cc2)cs1]

Prepared in a similar manner as described in Example 1.
$^1$H NMR (400 MHz, CDCl$_3$) δ (ppm): 8.01 (d, 2H), 7.84 (d, 2H), 7.48 (s, 1H), 3.23 (q, 4H), 3.08 (q, 2H), 1.45 (t, 3H), 1.14 (t, 6H). $^{13}$C NMR (100 MHz, CDCl$_3$) δ (ppm): 174.17, 152.56, 139.62, 137.37, 127.53, 126.85, 114.24, 41.96, 34.72, 26.80, 14.07. HRMS (ESI): m/z calcd for $C_{15}H_{20}N_2O_2S_2$ 324.10. found (M+H)$^+$ 325.10.

Example 5: Preparation of Compound 101

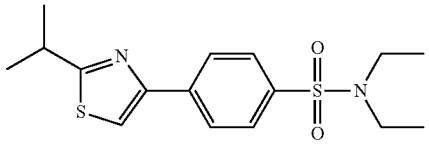 [SMILES: CCN(CC)S(=O)(=O)c1ccc(-c2csc(C(C)C)n2)cc1]

Prepared in a similar manner as described in Example 1.
$^1$H NMR (400 MHz, CDCl$_3$) δ (ppm): 8.02 (d, 2H), 7.84 (d, 2H), 7.48 (s, 1H), 3.35 (pentet, 1H), 3.23 (q, 4H), 1.46 (d, 6H), 1.14 (t, 6H). $^{13}$C NMR (100 MHz, CDCl$_3$) δ (ppm): 179.07, 152.57, 139.43, 137.70, 127.50, 126.83, 113.89, 41.96, 33.28, 23.17, 14.07. HRMS (ESI): m/z calcd for $C_{16}H_{22}N_2O_2S_2$ 338.11. found (M+H)$^+$ 339.12.

Example 6: Preparation of Compound 102

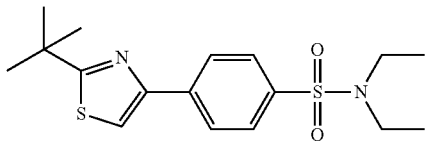 [SMILES: CCN(CC)S(=O)(=O)c1ccc(-c2csc(C(C)(C)C)n2)cc1]

Prepared in a similar manner as described in Example 1.
$^1$H NMR (400 MHz, CDCl$_3$) δ (ppm): 8.04 (d, 4H), 7.84 (d, 2H), 7.48 (s, 1H), 3.25 (q, 4H), 1.50 (s, 9H), 1.14 (t, 6H). $^{13}$C NMR (100 MHz, CDCl$_3$) δ (ppm): 181.94, 152.67, 139.16, 138.19, 127.44, 126.78, 113.87, 41.97, 37.91, 30.83, 14.1. HRMS (ESI): m/z calcd for $C_{17}H_{24}N_2O_2S_2$ 352.13. found (M+H)$^+$ 353.13.

Example 7: Preparation of Compound 103

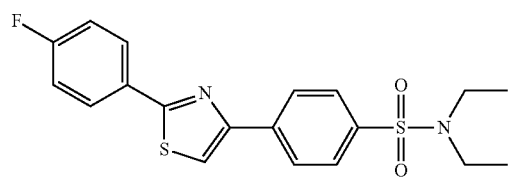 [SMILES: CCN(CC)S(=O)(=O)c1ccc(-c2csc(-c3ccc(F)cc3)n2)cc1]

Prepared in a similar manner as described in Example 1.
$^1$H NMR (400 MHz, CDCl$_3$) δ (ppm): 8.12 (d, 2H), 8.04 (m, 2H), 7.88 (d, 2H), 7.61 (s, 1H), 7.17 (t, 2H), 3.27 (q, 4H), 1.15 (t, 6H). $^{13}$C NMR (100 MHz, CDCl$_3$) δ (ppm): 167.30, 165.30, 162.80, 154.45, 139.62, 137.89, 128.52, 127.53, 126.82, 116.22, 116.00, 114.78, 41.98, 14.10. HRMS (ESI): m/z calcd for $C_{19}H_{19}FN_2O_2S_2$ 390.09. found (M+H)$^+$ 391.09.

Example 8: Preparation of Compound 104

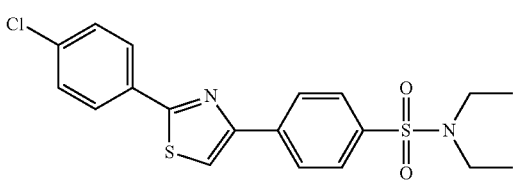

Prepared in a similar manner as described in Example 1.
$^1$H NMR (400 MHz, CDCl$_3$) δ (ppm): 8.08 (d, 2H), 7.98 (d, 2H), 7.89 (d, 2H), 7.62 (s, 1H), 7.46 (d, 2H), 3.28 (q, 4H), 1.15 (t, 6H). $^{13}$C NMR (100 MHz, CDCl$_3$) δ (ppm): 167.27, 154.50, 139.76, 137.66, 136.47, 131.64, 129.26, 127.87, 127.54, 126.88, 115.07, 41.99, 14.1. HRMS (ESI): m/z calcd for $C_{19}H_{19}ClN_2O_2S_2$ 406.06. found (M+H)$^+$ 407.06.

Example 9: Preparation of Compound 105

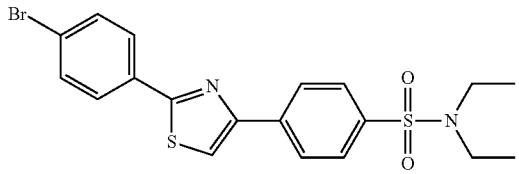 [SMILES: CCN(CC)S(=O)(=O)c1ccc(-c2csc(-c3ccc(Cl)cc3)n2)cc1]

Prepared in a similar manner as described in Example 1. $^1$H NMR (400 MHz, CDCl$_3$) δ (ppm): 8.11 (d, 2H), 7.87 (dd, 4H), 7.59 (m, 3H), 3.27 (t, 4H), 1.15 (t, 6H). $^{13}$C NMR (100 MHz, CDCl$_3$) δ (ppm): 167.36, 154.54, 139.79, 137.64, 132.22, 167.35, 154.54, 139.79, 137.64, 132.22, 128.78, 128.09, 127.56, 127.05, 126.90, 124.83, 115.11, 42.00, 14.11. HRMS (ESI): m/z calcd for C$_{19}$H$_{19}$BrN$_2$O$_2$S$_2$ 450.01. found (M+H)$^+$ 451.01.

Example 10: Preparation of Compound 106

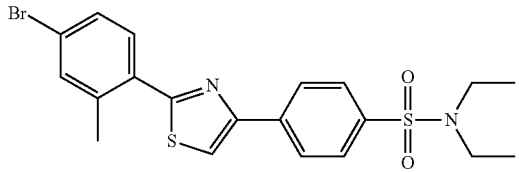

Prepared in a similar manner as described in Example 1. $^1$H NMR (400 MHz, CDCl$_3$) δ (ppm): 8.07 (d, 2H), 7.85 (d, 2H), 7.67 (s, 1H), 7.63 (d, 1H), 7.48 (s, 1H), 7.40 (dd, 1H), 3.25 (q, 4H), 2.64 (s, 3H), 1.12 (t, 6H). $^{13}$C NMR (100 MHz, CDCl$_3$) δ (ppm): 167.06, 154.00, 139.60, 138.71, 137.90, 134.45, 131.46, 131.18, 129.32, 127.55, 126.76, 123.86, 115.49, 41.99, 21.60, 14.10. HRMS (ESI): m/z calcd for C$_{20}$H$_{21}$BrN$_2$O$_2$S$_2$ 464.02. found (M+H)$^+$ 465.03.

Example 11: Preparation of Compound 107

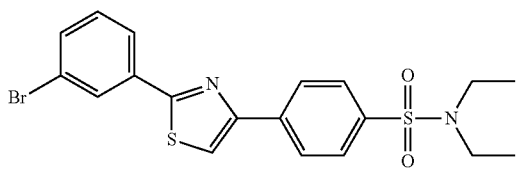 [SMILES: CCN(CC)S(=O)(=O)c1ccc(-c2csc(-c3cccc(Br)c3)n2)cc1]

Prepared in a similar manner as described in Example 1. $^1$H NMR (400 MHz, CDCl$_3$) δ (ppm): 8.14 (m, 3H), 7.89 (m, 3H), 7.62 (br s, 1H), 7.57 (d, 1H), 7.32 (m, 1H), 3.26 (q, 4H), 1.13 (t, 6H). $^{13}$C NMR (100 MHz, CDCl$_3$) δ (ppm): 139.77, 137.74, 133.20, 130.48, 129.41, 128.98, 128.78, 127.59, 127.13, 126.83, 125.21, 123.15, 115.31, 42.06, 14.07. HRMS (ESI): m/z calcd for C$_{19}$H$_{19}$BrN$_2$O$_2$S$_2$ 450.01. found (M+H)$^+$ 451.01.

Example 12: Preparation of Compound 108

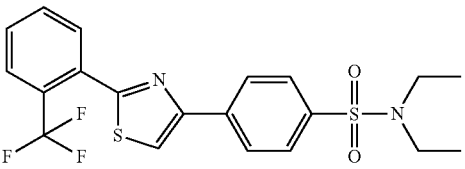 [SMILES: CCN(CC)S(=O)(=O)c1ccc(-c2csc(-c3ccccc3C(F)(F)F)n2)cc1]

Prepared in a similar manner as described in Example 1. $^1$H NMR (400 MHz, CDCl$_3$) δ (ppm): 8.02 (d, 2H), 7.85 (d, 2H), 7.49 (s, 1H), 7.37 (td, 1H), 7.29 (m, 1H), 7.12 (m, 2H), 4.43 (s, 2H), 3.25 (q, 4H), 1.13 (t, 6H). $^{13}$C NMR (100 MHz, CDCl$_3$) δ (ppm): 169.53, 162.03, 159.58, 153.47, 139.40, 138.05, 131.20, 129.32, 127.50, 126.74, 124.41, 115.76, 115.54, 115.18, 41.94, 32.82, 14.05. HRMS (ESI): m/z calcd for C$_{21}$H$_{21}$F$_3$N$_2$O$_2$S$_2$ 454.53. found (M+H)$^+$ 455.11.

Example 13: Preparation of Compound 109

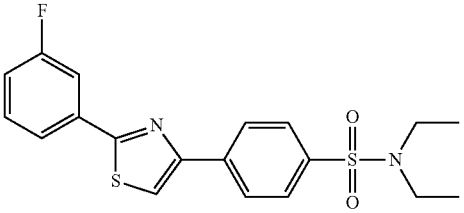 [SMILES: CCN(CC)S(=O)(=O)c1ccc(-c2csc(-c3cccc(F)c3)n2)cc1]

Prepared in a similar manner as described in Example 1. $^1$H NMR (400 MHz, CDCl$_3$) δ (ppm): 8.02 (d, 2H), 7.86 (d, 2H), 7.64 (s, 1H), 7.51 (m, 4H), 4.45 (s, 2H), 3.26 (m, 4H), 1.13 (m, 6H). $^{13}$C NMR (100 MHz, CDCl$_3$) δ (ppm): 169.32, 153.71, 139.54, 138.35, 137.89, 132.42, 129.30, 127.51, 126.74, 125.76, 124.13, 115.31, 41.95, 39.36, 14.06. HRMS (ESI): m/z calcd for C$_{20}$H$_{21}$FN$_2$O$_2$S$_2$ 404.52. found (M+H)$^+$ 405.11.

Example 14: Preparation of Compound 110

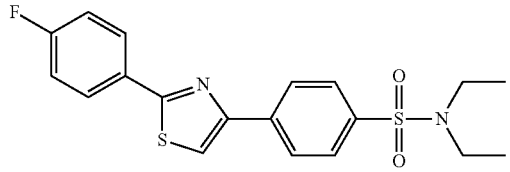 [SMILES: CCN(CC)S(=O)(=O)c1ccc(-c2csc(-c3ccc(F)cc3)n2)cc1]

Prepared in a similar manner as described in Example 1. $^1$H NMR (400 MHz, CDCl$_3$) δ (ppm): 8.02 (d, 2H), 7.86 (d, 2h), 7.50 (s, 1H), 7.32 (ddd, 1H), 7.13 (d, 1H), 7.06 (dt, 1H), 6.99 (td, 1H), 4.38 (s, 2H), 3.26 (q, 4H), 1.13 (t, 6H). $^{13}$C NMR (100 MHz, CDCl$_3$) δ (ppm): 169.79, 164.19, 161.72, 153.60, 139.85, 139.50, 137.97, 130.36, 127.51, 126.74, 124.68, 116.11, 115.90, 115.28, 114.34, 114.13, 41.95, 39.35, 14.06. HRMS (ESI): m/z calcd for C$_{20}$H$_{21}$FN$_2$O$_2$S$_2$ 404.52. found (M+H)$^+$ 405.11.

Example 15: Preparation of Compound 111

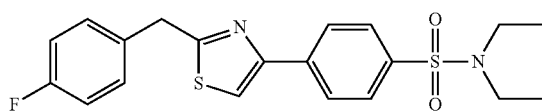 [SMILES: CCN(CC)S(=O)(=O)c1ccc(-c2csc(Cc3ccc(F)cc3)n2)cc1]

Prepared in a similar manner as described in Example 1. $^1$H NMR (400 MHz, CDCl$_3$) δ (ppm): 8.02 (d, 2H), 7.86 (d, 2H), 7.49 (s, 1H), 7.32 (dd, 2H), 7.05 (t, 2H), 4.36 (s, 2H), 3.26 (q, 4H), 1.13 (t, 6H). $^{13}$C NMR (100 MHz, CDCl$_3$) δ (ppm): 170.82, 163.30, 160.86, 153.57, 139.49, 138.02, 133.24, 130.67, 127.52, 126.73, 115.82, 115.61, 115.19, 41.95, 38.94, 14.07. HRMS (ESI): m/z calcd for C$_{20}$H$_{21}$FN$_2$O$_2$S$_2$ 404.52. found (M+H)$^+$ 405.11.

Example 16: Preparation of Compound 112

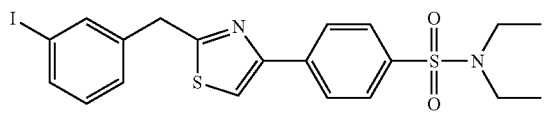 [SMILES: CCN(CC)S(=O)(=O)c1ccc(-c2csc(Cc3cccc(I)c3)n2)cc1]

Prepared in a similar manner as described in Example 1. $^1$H NMR (400 MHz, CDCl$_3$) δ (ppm): 8.02 (d, 2H), 7.86 (d, 2H), 7.72 (s, 1H), 7.62 (d, 1H), 7.50 (s, 1H), 7.32 (d, 1H), 7.09 (t, 1H), 4.33 (d, 2H), 3.26 (q, 4H), 1.14 (t, 6H). $^{13}$C NMR (100 MHz, CDCl$_3$) δ (ppm): 169.76, 153.65, 139.75, 139.54, 137.95, 136.39, 130.52, 128.32, 127.54, 126.77, 115.32, 94.66, 41.97, 39.15, 14.09. HRMS (ESI): m/z calcd for C$_{20}$H$_{21}$IN$_2$O$_2$S$_2$ 512.43. found (M+H)$^+$ 513.02.

Example 17: Preparation of Compound 113

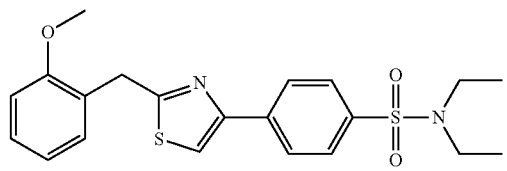 [SMILES: CCN(CC)S(=O)(=O)c1ccc(-c2csc(Cc3ccccc3OC)n2)cc1]

Prepared in a similar manner as described in Example 1. $^1$H NMR (400 MHz, CDCl$_3$) δ (ppm): 8.02 (d, 2H), 7.84 (d, 2H), 7.44 (s, 1H), 7.29 (m, 2H), 6.94 (m, 2H), 4.39 (s, 2H), 3.86 (s, 3H), 3.25 (q, 4H), 1.13 (t, 6H). $^{13}$C NMR (100 MHz, CDCl$_3$) δ (ppm): 171.40, 157.27, 153.03, 139.75, 138.39, 130.82, 128.70, 127.49, 126.78, 126.07, 120.73, 114.87, 110.53, 55.13, 41.71, 34.37, 13.98. HRMS (ESI): m/z calcd for C$_{21}$H$_{24}$N$_2$O$_3$S$_2$ 416.56. found (M+H)$^+$ 417.13.

Example 18: Preparation of Compound 114

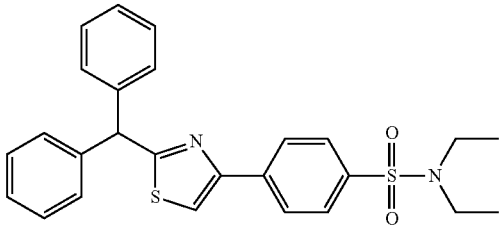 [SMILES: CCN(CC)S(=O)(=O)c1ccc(-c2csc(C(c3ccccc3)c3ccccc3)n2)cc1]

Prepared in a similar manner as described in Example 1. $^1$H NMR (400 MHz, CDCl$_3$) δ (ppm): 8.02 (d, 2H), 7.83 (d, 2H), 7.55 (s, 1H), 7.30 (m, 10H), 5.89 (s, 1H), 3.24 (q, 4H), 1.12 (t, 6H). $^{13}$C NMR (100 MHz, CDCl$_3$) δ (ppm): 173.91, 153.75, 141.75, 139.37, 138.10, 128.90, 128.61, 127.44, 127.24, 126.79, 115.41, 55.12, 41.94, 14.06.

Example 19: Preparation of Compound 115

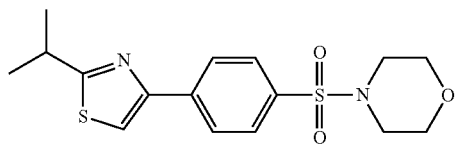 [SMILES: CC(C)c1nc(-c2ccc(S(=O)(=O)N3CCOCC3)cc2)cs1]

Prepared in a similar manner as described in Example 1. $^1$H NMR (400 MHz, CDCl$_3$) δ (ppm): 8.08 (d, 2H), 7.78 (d, 2H), 7.51 (s, 1H), 7.75 (dd, 4H), 3.39 (septet, 1H), 3.02 (dd, 4H), 1.46 (d, 6H). $^{13}$C NMR (100 MHz, CDCl$_3$) δ (ppm): 178.63, 152.72, 139.19, 133.80, 128.32, 126.81, 114.24, 66.08, 45.99, 33.44, 23.11. HRMS (ESI): m/z calcd for C$_{16}$H$_{20}$N$_2$O$_3$S$_2$ 352.47. found (M+H)$^+$ 353.10.

Example 20: Preparation of Compound 116

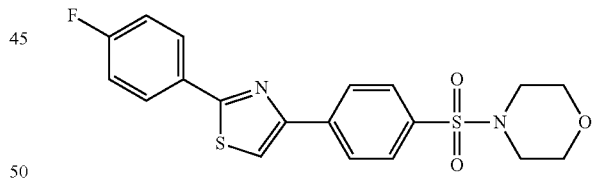

Prepared in a similar manner as described in Example 1. $^1$H NMR (400 MHz, CDCl$_3$) δ (ppm): 8.17 (d, 2H), 8.03 (dd. 2H), 7.83 (d, 2H), 7.64 (s, 1H), 7.18 (t, 2H), 3.75 (dd, 4H), 3.04 (dd, 4H). $^{13}$C NMR (100 MHz, CDCl$_3$) δ (ppm): 167.45, 165.40, 162.82, 154.28, 138.72, 134.19, 128.66, 128.56, 128.41, 126.92, 116.33, 116.01, 115.15, 66.11, 46.02. HRMS (ESI): m/z calcd for C$_{19}$H$_{17}$FN$_2$O$_3$S$_2$ 404.48. found (M+H)$^+$ 405.08.

PHARMACEUTICAL COMPOSITION EXAMPLES

Example A1: Parenteral Composition

To prepare a parenteral pharmaceutical composition suitable for administration by injection, 100 mg of a watersoluble salt of a compound of Formula (I), Formula (Ia), Formula (Ib), Formula (Ic), Formula (Id), Formula (II), Formula (III), Formula (IV), or Formula (V), or pharmaceutically acceptable salt, N-oxide, racemate or stereoisomer thereof, is dissolved in 2% HPMC, 1% Tween 80 in DI water, pH 2.2 with MSA, q.s. to at least 20 mg/mL. The mixture is incorporated into a dosage unit form suitable for administration by injection.

Example A2: Oral Composition

To prepare a pharmaceutical composition for oral delivery, 100 mg of a compound of Formula (I), Formula (Ia), Formula (Ib), Formula (Ic), Formula (Id), Formula (II), Formula (III), Formula (IV), or Formula (V), or pharmaceutically acceptable salt, N-oxide, racemate or stereoisomer thereof, is mixed with 750 mg of starch. The mixture is incorporated into an oral dosage unit for, such as a hard gelatin capsule, which is suitable for oral administration.

BIOLOGY EXAMPLES

Example B1: In-Vitro Biochemical Assay Measuring FAS-TE Inhibition

Assay Components:

| RXN Buffer | | | |
|---|---|---|---|
| | [Stock] | [2x] | [Assay] (20 μL final) |
| Tris, pH 7.5 | 1M | 200 mM | 100 mM |
| NaCl | 3M | 100 mM | 50 mM |
| Brij-35 | 10% | 0.01% | 0.005% |
| TCEP | 500 mM | 2 mM | 1 mM |
| Sarcosine | 5M | 1000 mM | 500 mM |

| Substrate/Enzyme | | | |
|---|---|---|---|
| | [Stock] | [2x] | [Assay] (20 μL final) |
| OMFH | 10 mM in DMSO | 20 μM | 10 μM |
| FASN-TE | 68.42 μM | 1.8 μM | 0.9 μM |

Prepare OMFH in diH$_2$O + 10% DMSO
Prepare FASN-TE in RXN Buffer

Min wells: Substrate+No enzyme+DMSO, Max wells: Substrate+Enzyme+DMSO, Sample wells: Substrate+Enzyme+Test compounds, Reference compound: Orlistat (make a fresh 10 mM stock in DMSO each time). 384-well black, low-volume plate (Greiner #784076)

Assay Protocol:
1) ECHO transfer 160 nL of 125× Compound (or DMSO for control wells) per well.
2) For Max and Sample wells: Add 10 μL of Enzyme (2×; 1.8 μM) prepared in RXN Buffer. For Min wells: Add 10 μL of RXN Buffer (No Enzyme).
3) For all wells: Add 10 μL of Substrate (2×; 20 μM) prepared in diH$_2$O+10% DMSO.
4) Centrifuge plate for 1 minute at 1,000 rpm.
5) Measure fluorescence every 5 minutes for 1-1.5 hours using the BMG POLARstar (ex 485 nm/em 520 nm; Gain=1015; 25 flashes).
6) All volumes can be adjusted but the final DMSO concentration should be kept at about 6%.

Data Analysis:
1) Calculate slopes and express as % Activity (Min wells=0%; Max wells=100%).
2) Then, using Prism, calculate the IC$_{50}$ values.

Representative in vitro biochemical data is presented in Table 4.

TABLE 4

| Comp. | Structure | FAS-TE inhibition (IC$_{50}$) (μM) | n | SEM |
|---|---|---|---|---|
| 1 | 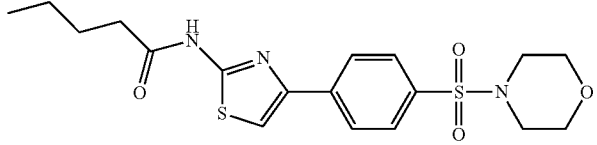 [SMILES: CCCCC(=O)Nc1nc(-c2ccc(S(=O)(=O)N3CCOCC3)cc2)cs1] | 0.199<br>0.204<br>0.555 | 1<br><br> | —<br>0.004<br>0.038 |
| 2 | 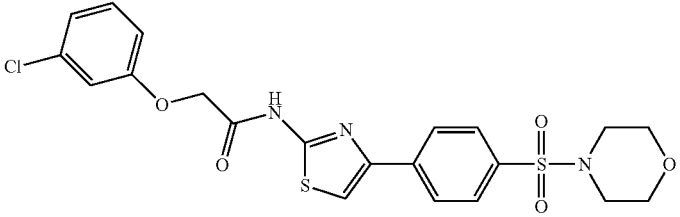 [SMILES: O=C(COc1cccc(Cl)c1)Nc1nc(-c2ccc(S(=O)(=O)N3CCOCC3)cc2)cs1] | 4.5 | 1 | — |

TABLE 4-continued

| Comp. | Structure | FAS-TE inhibition (IC$_{50}$) (μM) | n | SEM |
|---|---|---|---|---|
| 3 | 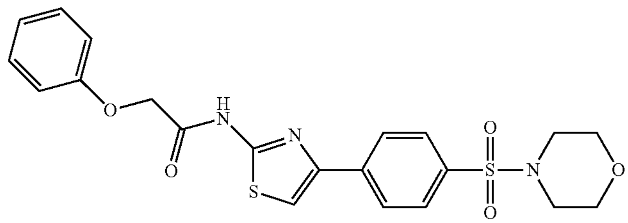 [SMILES: O=C(COc1ccccc1)Nc1nc(-c2ccc(S(=O)(=O)N3CCOCC3)cc2)cs1] | 0.42 | 1 | — |
| 4 | 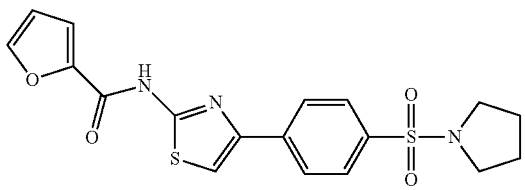 [SMILES: O=C(Nc1nc(-c2ccc(S(=O)(=O)N3CCCC3)cc2)cs1)c1ccco1] | 4.68 | 1 | — |
| 5 | 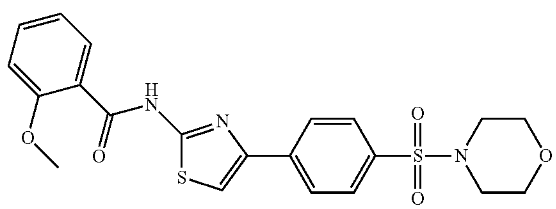 [SMILES: COc1ccccc1C(=O)Nc1nc(-c2ccc(S(=O)(=O)N3CCOCC3)cc2)cs1] | 11.88 | 1 | — |
| 6 | 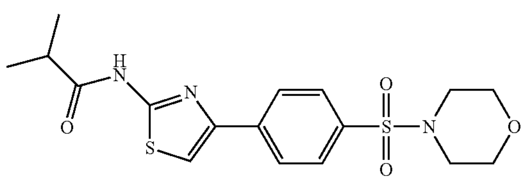 [SMILES: CC(C)C(=O)Nc1nc(-c2ccc(S(=O)(=O)N3CCOCC3)cc2)cs1] | 0.82 | 5 | 0.066 |
| 7 | 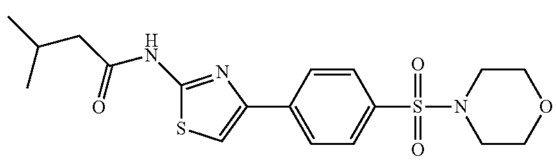 [SMILES: CC(C)CC(=O)Nc1nc(-c2ccc(S(=O)(=O)N3CCOCC3)cc2)cs1] | 11.6 | 4 | 4.02 |
| 8 | 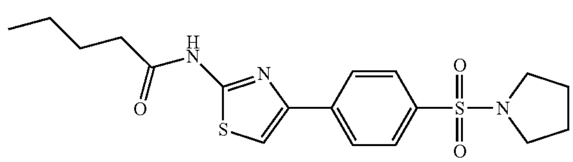 [SMILES: CCCCC(=O)Nc1nc(-c2ccc(S(=O)(=O)N3CCCC3)cc2)cs1] | 0.20 | 4 | 0.002 |
| 9 | 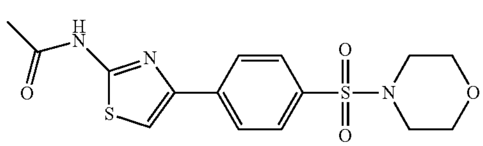 [SMILES: CC(=O)Nc1nc(-c2ccc(S(=O)(=O)N3CCOCC3)cc2)cs1] | 13.4 | 8 | 3.92 |
| 10 | 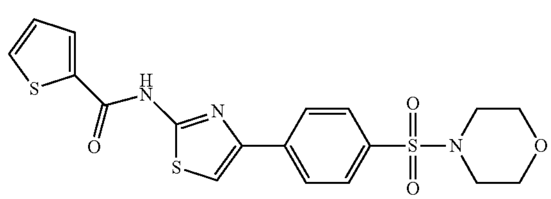 [SMILES: O=C(Nc1nc(-c2ccc(S(=O)(=O)N3CCOCC3)cc2)cs1)c1ccco1] | 32.9 | 3 | 3.781 |

TABLE 4-continued

| Comp. | Structure | FAS-TE inhibition (IC$_{50}$) (μM) | n SEM |
|---|---|---|---|
| 11 | 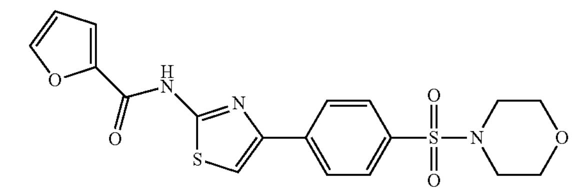 | 37.4 | 4 4.100 |
| 12 | 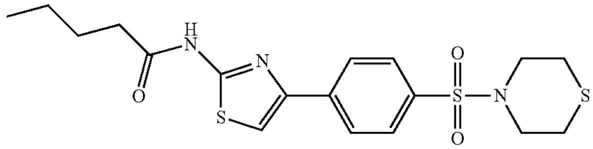 [SMILES: CCCCC(=O)Nc1nc(-c2ccc(S(=O)(=O)N3CCSCC3)cc2)cs1] | 0.71 | 4 0.043 |
| 13 | 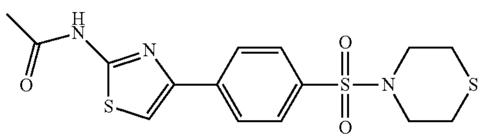 [SMILES: CC(=O)Nc1nc(-c2ccc(S(=O)(=O)N3CCSCC3)cc2)cs1] | >80 | 4 — |
| 14 | 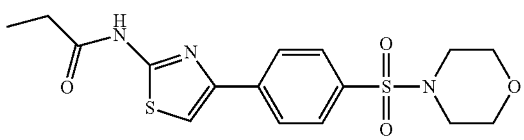 [SMILES: CCC(=O)Nc1nc(-c2ccc(S(=O)(=O)N3CCOCC3)cc2)cs1] | 4.5 | 4 0.705 |
| 15 | 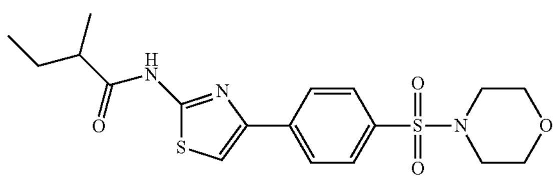 [SMILES: CCC(C)C(=O)Nc1nc(-c2ccc(S(=O)(=O)N3CCOCC3)cc2)cs1] | 0.31 | 4 0.021 |
| 16 | 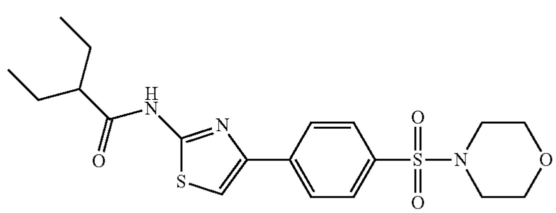 [SMILES: CCC(CC)C(=O)Nc1nc(-c2ccc(S(=O)(=O)N3CCOCC3)cc2)cs1] | 0.334 | 4 0.030 |
| 17 | 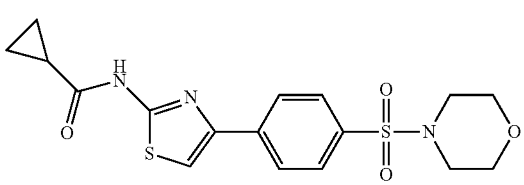 [SMILES: O=C(Nc1nc(-c2ccc(S(=O)(=O)N3CCOCC3)cc2)cs1)C1CC1] | 5.2 | 3 1.114 |
| 18 | 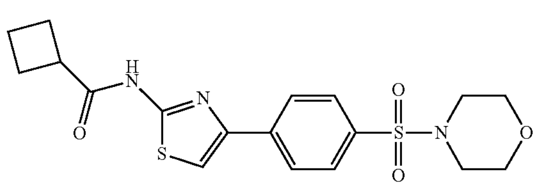 [SMILES: O=C(Nc1nc(-c2ccc(S(=O)(=O)N3CCOCC3)cc2)cs1)C1CCC1] | 3.6 | 4 0.324 |

TABLE 4-continued

| Comp. | Structure | FAS-TE inhibition (IC$_{50}$) (μM) | n | SEM |
|---|---|---|---|---|
| 19 | cyclopentanecarbonyl-NH-thiazole-phenyl-SO$_2$-morpholine | >80 | 4 | — |
| 20 | cyclohexanecarbonyl-NH-thiazole-phenyl-SO$_2$-morpholine | >80 | 4 | — |
| 21 | tBuO-C(O)-NH-thiazole-phenyl-SO$_2$-morpholine | 29.0 | 4 | 3.720 |
| 22 | pentanoyl-NH-thiazole-phenyl-SO$_2$-(4-methylpiperidine) | 0.501 | 4 | 0.032 |
| 23 | propanoyl-NH-thiazole-phenyl-SO$_2$-(4-methylpiperidine) | >80 | 4 | — |
| 24 | isobutyryl-NH-thiazole-phenyl-SO$_2$-(4-methylpiperidine) | 0.66 | 4 | 0.063 |
| 25 | cyclopropanecarbonyl-NH-thiazole-phenyl-SO$_2$-(4-methylpiperidine) | >80 | 4 | — |
| 26 | propanoyl-NH-thiazole-phenyl-SO$_2$-pyrrolidine | 0.65 | 1 | — |
| 27 | isobutyryl-NH-thiazole-phenyl-SO$_2$-pyrrolidine | 0.277 | 4 | 0.028 |

TABLE 4-continued
| Comp. | Structure | FAS-TE inhibition (IC$_{50}$) (μM) | n | SEM |
|---|---|---|---|---|
| 28 | 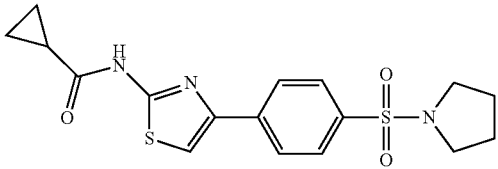 [SMILES: O=C(Nc1nc(-c2ccc(S(=O)(=O)N3CCCC3)cc2)cs1)C1CC1] | 0.56 | 2 | 0.124 |
| 29 | 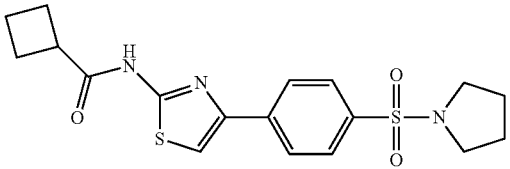 [SMILES: O=C(Nc1nc(-c2ccc(S(=O)(=O)N3CCCC3)cc2)cs1)C1CCC1] | 0.40 | 4 | 0.020 |
| 30 | 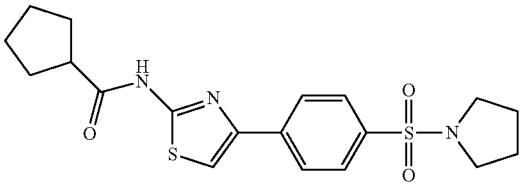 [SMILES: O=C(Nc1nc(-c2ccc(S(=O)(=O)N3CCCC3)cc2)cs1)C1CCCC1] | 0.73 | 4 | 0.036 |
| 31 | 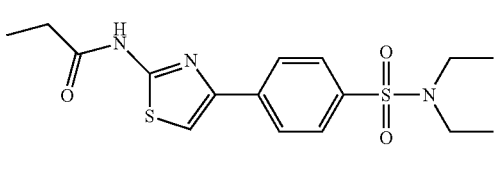 [SMILES: CCC(=O)Nc1nc(-c2ccc(S(=O)(=O)N(CC)CC)cc2)cs1] | 4.25 | 3 | 0.417 |
| 32 | 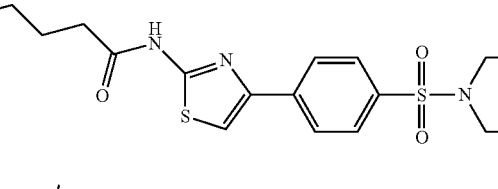 | 0.172 | 4 | 0.009 |
| 33 | 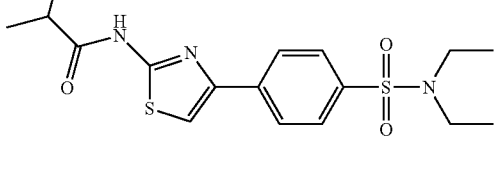 | 0.28 | 4 | 0.038 |
| 34 | 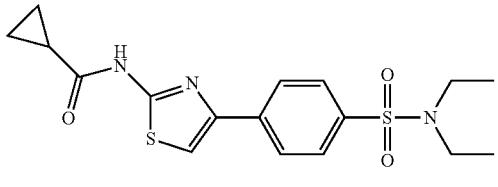 [SMILES: CCN(CC)S(=O)(=O)c1ccc(-c2csc(NC(=O)C3CC3)n2)cc1] | 2.3 | 3 | 0.052 |
| 35 | 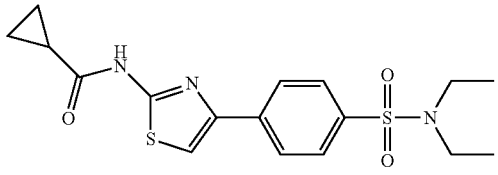 [SMILES: CCN(CC)S(=O)(=O)c1ccc(-c2csc(NC(=O)C3CC3)n2)cc1] | 0.99 | 4 | 0.077 |

TABLE 4-continued
| Comp. | Structure | FAS-TE inhibition (IC$_{50}$) (μM) | n SEM |
|---|---|---|---|
| 36 | 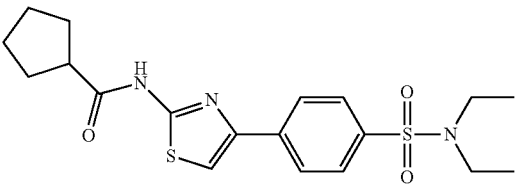 [SMILES: CCN(CC)S(=O)(=O)c1ccc(-c2csc(NC(=O)C3CCCC3)n2)cc1] | 1.2 | 4 0.189 |
| 37 | 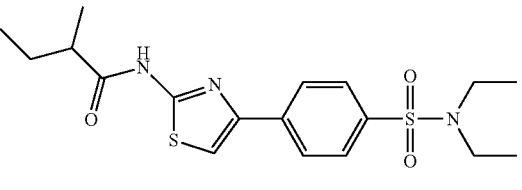 [SMILES: CCC(C)C(=O)Nc1nc(-c2ccc(S(=O)(=O)N(CC)CC)cc2)cs1] | 0.30 | 4 0.042 |
| 38 | 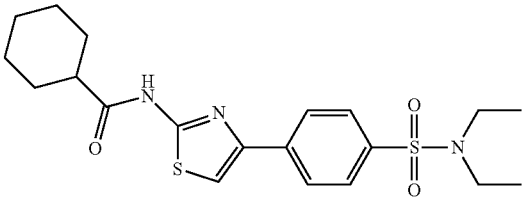 [SMILES: CCN(CC)S(=O)(=O)c1ccc(-c2csc(NC(=O)C3CCCCC3)n2)cc1] | 2.9 | 4 0.170 |
| 39 | 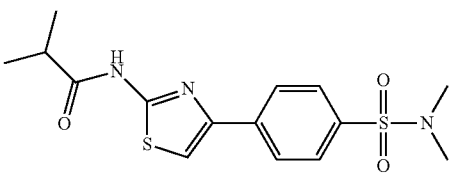 [SMILES: CC(C)C(=O)Nc1nc(-c2ccc(S(=O)(=O)N(C)C)cc2)cs1] | 0.58 | 4 0.032 |
| 40 | 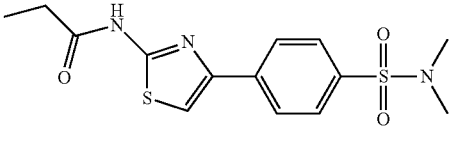 [SMILES: CCC(=O)Nc1nc(-c2ccc(S(=O)(=O)N(C)C)cc2)cs1] | 1.1 | 4 0.169 |
| 41 | 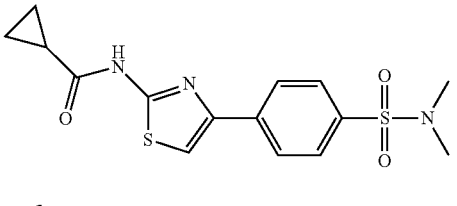 | 1.2 | 4 0.080 |
| 42 | 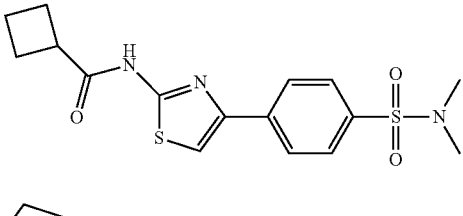 | 1.4 | 4 0.045 |
| 43 | 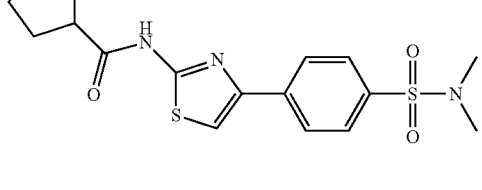 | 1.6 | 4 0.119 |

TABLE 4-continued

| Comp. | Structure | FAS-TE inhibition (IC$_{50}$) (μM) | n | SEM |
|---|---|---|---|---|
| 44 | 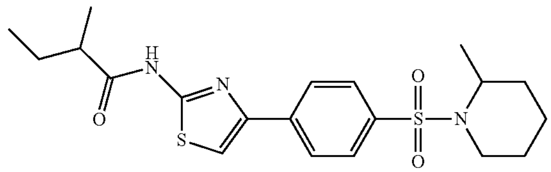 [SMILES: CCC(C)C(=O)Nc1nc(-c2ccc(S(=O)(=O)N3CCCCC3C)cc2)cs1] | 0.29 | 4 | 0.009 |
| 45 | 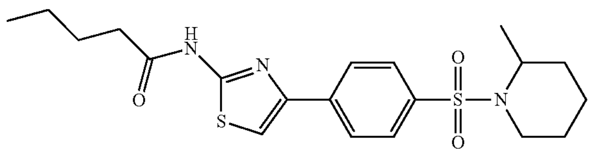 [SMILES: CCCCC(=O)Nc1nc(-c2ccc(S(=O)(=O)N3CCCCC3C)cc2)cs1] | 0.38 | 4 | 0.015 |
| 46 | 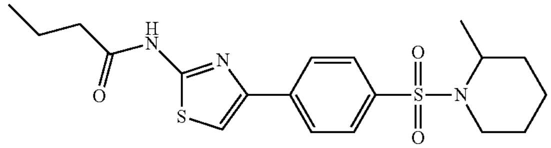 [SMILES: CCCC(=O)Nc1nc(-c2ccc(S(=O)(=O)N3CCCCC3C)cc2)cs1] | 0.58 | 4 | 0.011 |
| 47 | 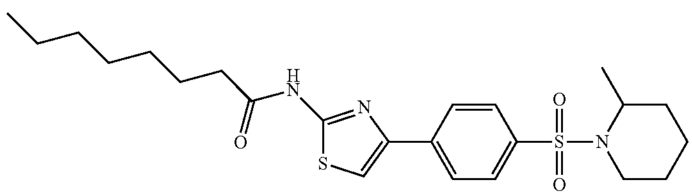 [SMILES: CCCCCCCC(=O)Nc1nc(-c2ccc(S(=O)(=O)N3CCCCC3C)cc2)cs1] | 4.3 | 4 | 0.213 |
| 48 | 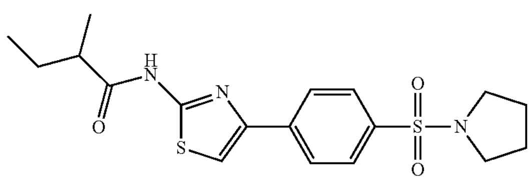 [SMILES: CCC(C)C(=O)Nc1nc(-c2ccc(S(=O)(=O)N3CCCC3)cc2)cs1] | 0.15 | 4 | 0.002 |
| 49 | 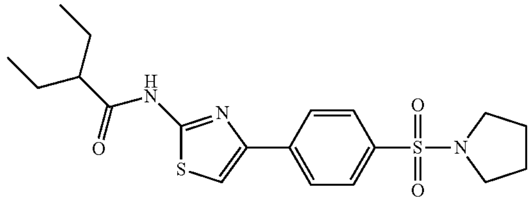 [SMILES: CCC(CC)C(=O)Nc1nc(-c2ccc(S(=O)(=O)N3CCCC3)cc2)cs1] | 0.26 | 4 | 0.004 |
| 50 | 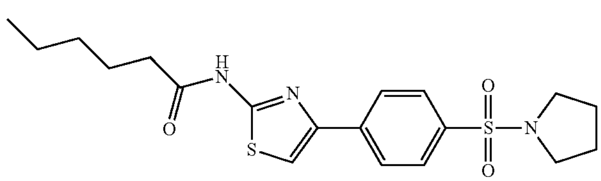 [SMILES: CCCCCC(=O)Nc1nc(-c2ccc(S(=O)(=O)N3CCCC3)cc2)cs1] | 0.14 | 4 | 0.003 |
| 51 | 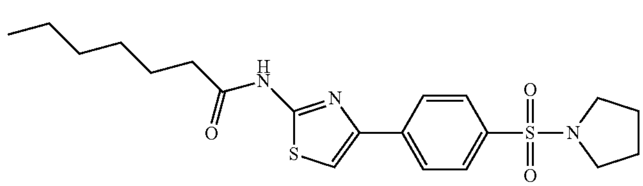 [SMILES: CCCCCCC(=O)Nc1nc(-c2ccc(S(=O)(=O)N3CCCC3)cc2)cs1] | 0.85 | 4 | 0.041 |

TABLE 4-continued

| Comp. | Structure | FAS-TE inhibition (IC$_{50}$) (μM) | n | SEM |
|---|---|---|---|---|
| 52 | 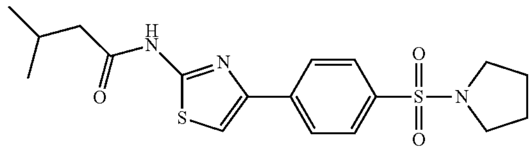 [SMILES: CC(C)CC(=O)Nc1nc(-c2ccc(S(=O)(=O)N3CCCC3)cc2)cs1] | 1.6 | 4 | 0.062 |
| 53 | 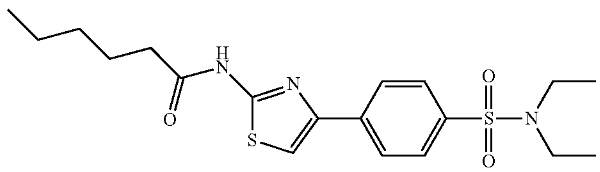 [SMILES: CCCCCC(=O)Nc1nc(-c2ccc(S(=O)(=O)N(CC)CC)cc2)cs1] | 0.20 | 4 | 0.006 |
| 54 | 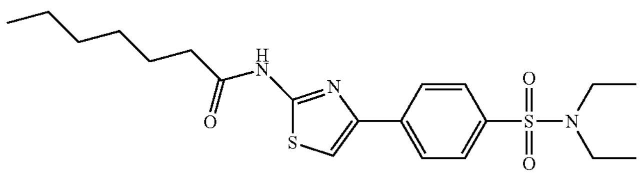 [SMILES: CCCCCCC(=O)Nc1nc(-c2ccc(S(=O)(=O)N(CC)CC)cc2)cs1] | 1.4 | 4 | 0.028 |
| 55 | 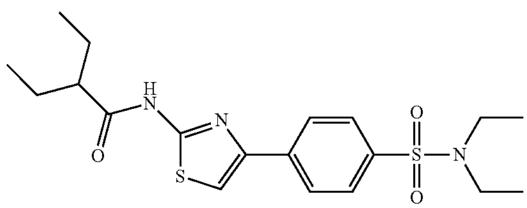 [SMILES: CCC(CC)C(=O)Nc1nc(-c2ccc(S(=O)(=O)N(CC)CC)cc2)cs1] | 0.33 | 4 | 0.004 |
| 56 | 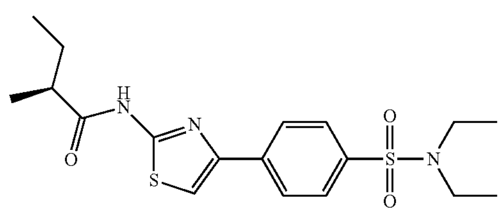 [SMILES: CC[C@H](C)C(=O)Nc1nc(-c2ccc(S(=O)(=O)N(CC)CC)cc2)cs1] | NT | | NT |
| 57 | 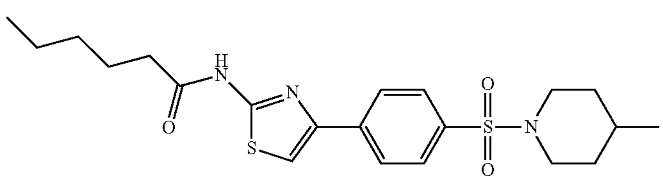 [SMILES: CCCCCC(=O)Nc1nc(-c2ccc(S(=O)(=O)N3CCC(C)CC3)cc2)cs1] | 0.75 | 4 | 0.031 |
| 58 | 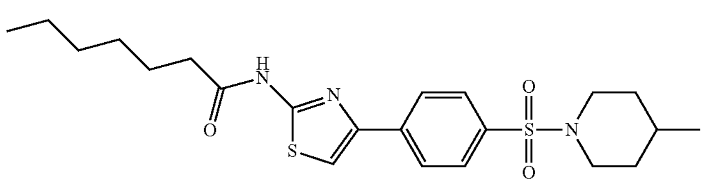 [SMILES: CCCCCCC(=O)Nc1nc(-c2ccc(S(=O)(=O)N3CCC(C)CC3)cc2)cs1] | 4.5 | 4 | 0.367 |
| 59 | 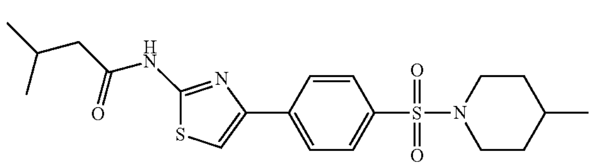 [SMILES: CC(C)CC(=O)Nc1nc(-c2ccc(S(=O)(=O)N3CCC(C)CC3)cc2)cs1] | 60.4 | 2 | 2.786 |

TABLE 4-continued
| Comp. | Structure | FAS-TE inhibition (IC$_{50}$) (μM) | n SEM |
|---|---|---|---|
| 60 | 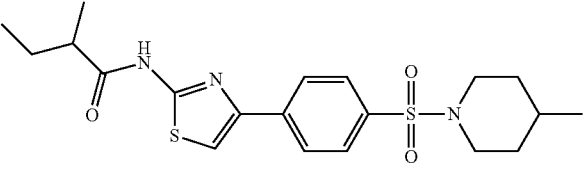 [SMILES: CCC(C)C(=O)Nc1nc(-c2ccc(S(=O)(=O)N3CCC(C)CC3)cc2)cs1] | 0.41 | 4 0.004 |
| 61 | 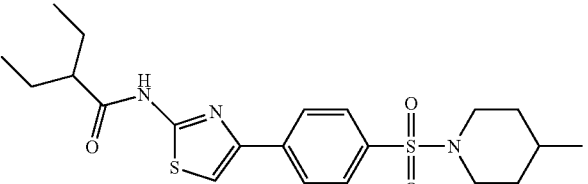 | 1.8 | 4 0.091 |
| 62 | 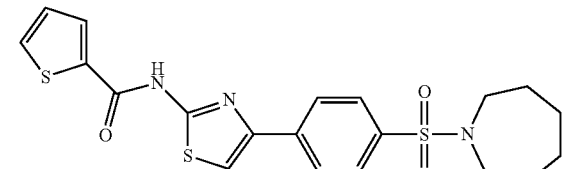 | NT | NT |
| 63 | 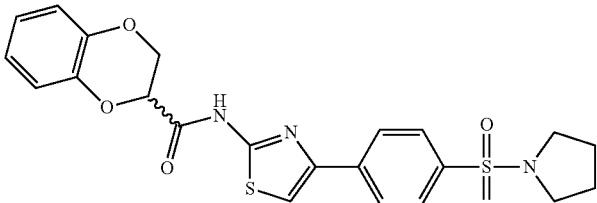 | 1.31 | 1 0.27 |
| 64 | 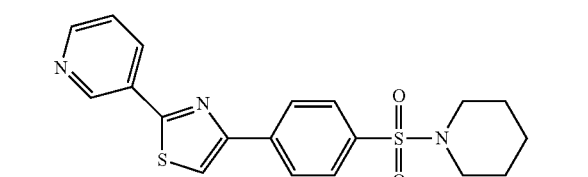 | 2.68 | 1 0.27 |
| 65 | 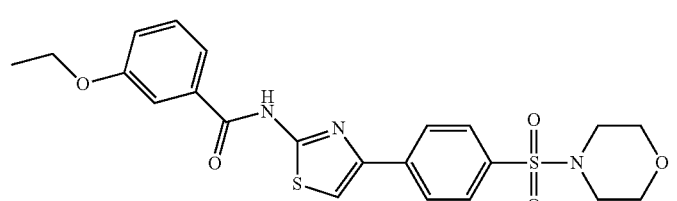 | NT | NT |
| 66 | 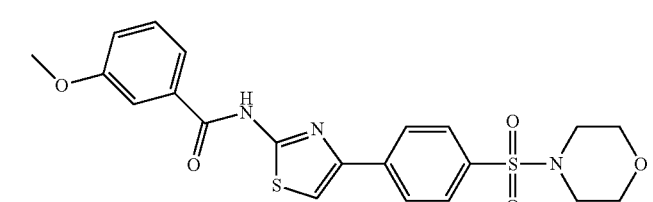 | NT | NT |

TABLE 4-continued

| Comp. | Structure | FAS-TE inhibition (IC$_{50}$) (μM) | n SEM |
|---|---|---|---|
| 67 | 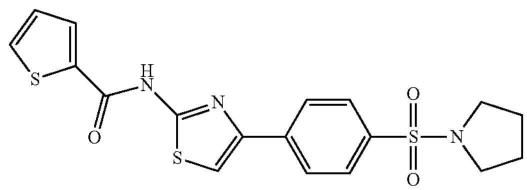 | NT | NT |
| 68 | 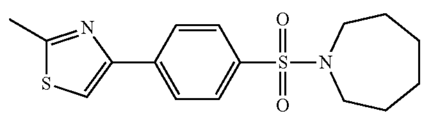 [SMILES: Cc1nc(-c2ccc(S(=O)(=O)N3CCCCCC3)cc2)cs1] | NT | NT |
| 69 | 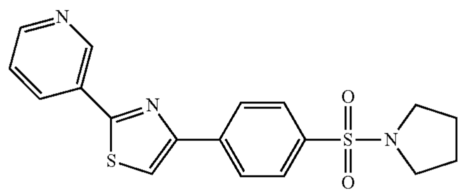 [SMILES: O=S(=O)(c1ccc(-c2csc(-c3cccnc3)n2)cc1)N1CCCC1] | 1.51 | 1 0.11 |
| 70 | 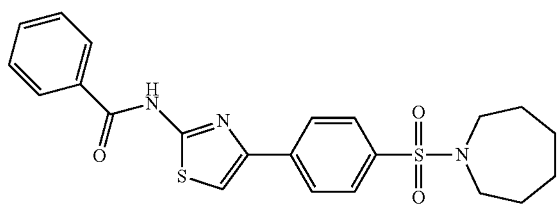 [SMILES: O=C(Nc1nc(-c2ccc(S(=O)(=O)N3CCCCCC3)cc2)cs1)c1ccccc1] | NT | NT |
| 71 | 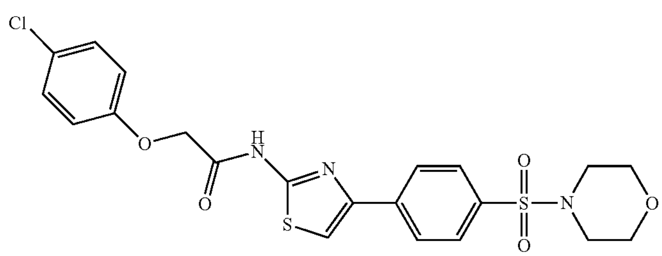 [SMILES: O=C(COc1ccc(Cl)cc1)Nc1nc(-c2ccc(S(=O)(=O)N3CCOCC3)cc2)cs1] | NT | NT |
| 72 | 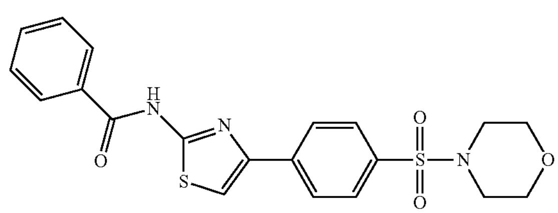 [SMILES: O=C(Nc1nc(-c2ccc(S(=O)(=O)N3CCOCC3)cc2)cs1)c1ccccc1] | NT | NT |
| 73 | 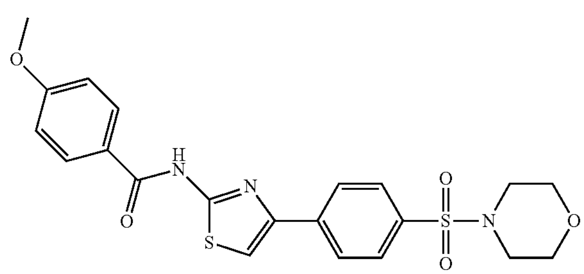 [SMILES: COc1ccc(C(=O)Nc2nc(-c3ccc(S(=O)(=O)N4CCOCC4)cc3)cs2)cc1] | NT | NT |

TABLE 4-continued

| Comp. | Structure | FAS-TE inhibition (IC$_{50}$) (μM) | n SEM |
|---|---|---|---|
| 74 | 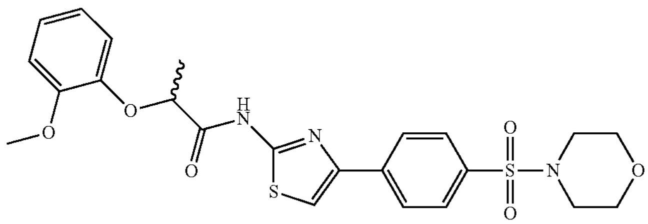 [SMILES: COc1ccccc1OC(C)C(=O)Nc1nc(-c2ccc(S(=O)(=O)N3CCOCC3)cc2)cs1] | NT | NT |
| 75 | 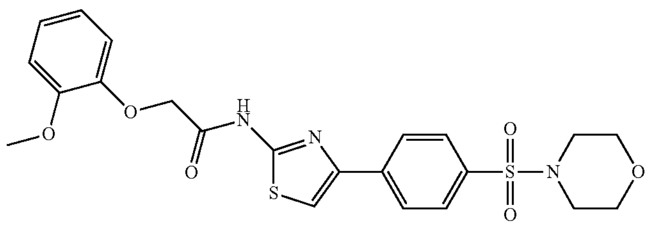 [SMILES: COc1ccccc1OCC(=O)Nc1nc(-c2ccc(S(=O)(=O)N3CCOCC3)cc2)cs1] | NT | NT |
| 76 | 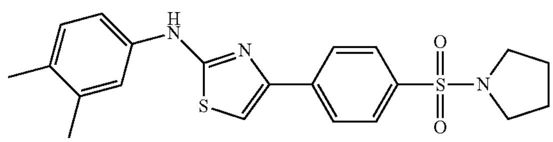 [SMILES: Cc1ccc(Nc2nc(-c3ccc(S(=O)(=O)N4CCCC4)cc3)cs2)cc1C] | NT | NT |
| 77 | 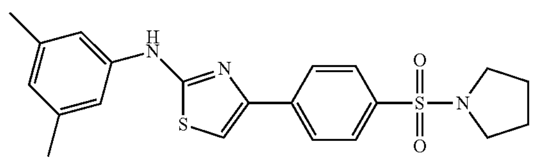 [SMILES: Cc1cc(C)cc(Nc2nc(-c3ccc(S(=O)(=O)N4CCCC4)cc3)cs2)c1] | NT | NT |
| 78 | 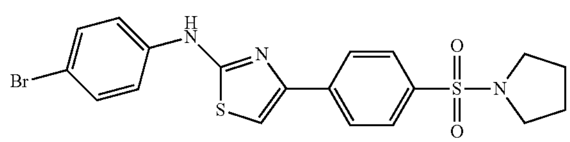 [SMILES: O=S(=O)(c1ccc(-c2csc(Nc3ccc(Br)cc3)n2)cc1)N1CCCC1] | NT | NT |
| 79 | 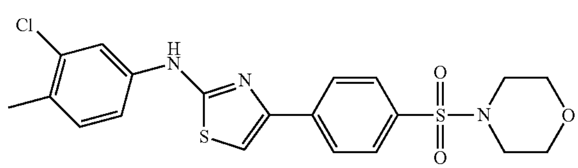 [SMILES: Cc1ccc(Nc2nc(-c3ccc(S(=O)(=O)N4CCOCC4)cc3)cs2)cc1Cl] | NT | NT |
| 80 | 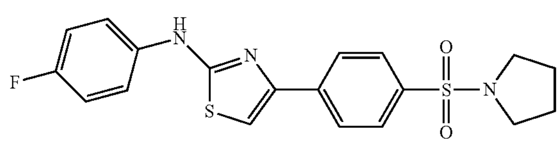 [SMILES: O=S(=O)(c1ccc(-c2csc(Nc3ccc(F)cc3)n2)cc1)N1CCCC1] | 14.8 | 1 2.72 |
| 81 | 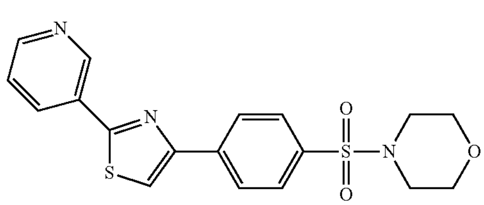 [SMILES: O=S(=O)(c1ccc(-c2csc(-c3cccnc3)n2)cc1)N1CCOCC1] | 2.14 | 1 0.23 |
| 82 | 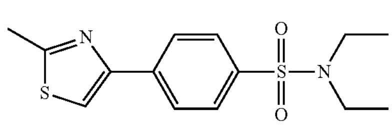 [SMILES: CCN(CC)S(=O)(=O)c1ccc(-c2csc(C)n2)cc1] | 80 | 1 — |

TABLE 4-continued

| Comp. | Structure | FAS-TE inhibition (IC$_{50}$) (μM) | n | SEM |
|---|---|---|---|---|
| 83 | 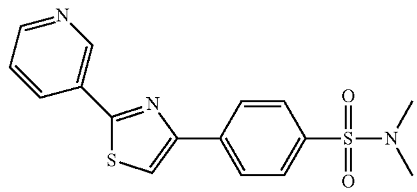 [SMILES: CN(C)S(=O)(=O)c1ccc(-c2csc(-c3cccnc3)n2)cc1] | 5.21 | 1 | 0.44 |
| 84 | 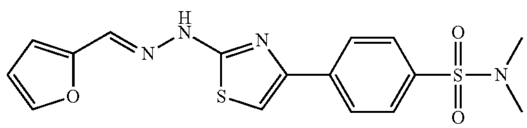 [SMILES: CN(C)S(=O)(=O)c1ccc(-c2csc(N/N=C/c3ccco3)n2)cc1] | NT | | NT |
| 85 | 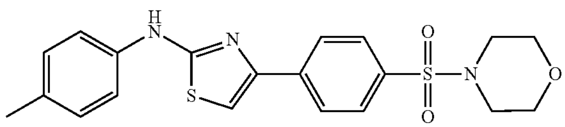 [SMILES: Cc1ccc(Nc2nc(-c3ccc(S(=O)(=O)N4CCOCC4)cc3)cs2)cc1] | NT | | NT |
| 86 | 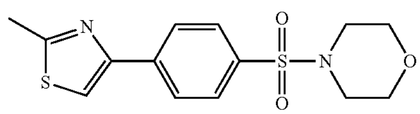 [SMILES: Cc1nc(-c2ccc(S(=O)(=O)N3CCOCC3)cc2)cs1] | NT | | NT |
| 87 | 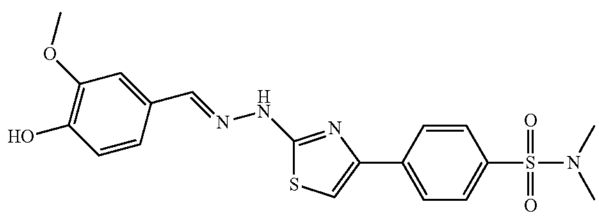 [SMILES: COc1cc(/C=N/Nc2nc(-c3ccc(S(=O)(=O)N(C)C)cc3)cs2)ccc1O] | NT | | NT |
| 88 | 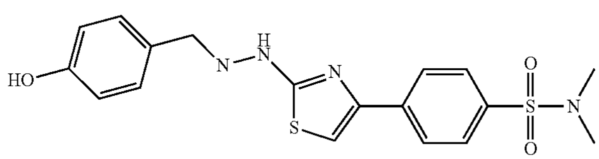 [SMILES: CN(C)S(=O)(=O)c1ccc(-c2csc(NNCc3ccc(O)cc3)n2)cc1] | NT | | NT |
| 89 | 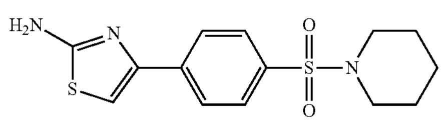 [SMILES: Nc1nc(-c2ccc(S(=O)(=O)N3CCCCC3)cc2)cs1] | NT | | NT |
| 90 | 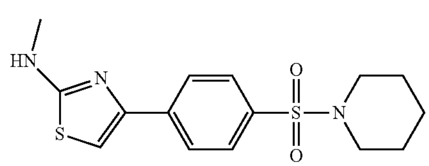 [SMILES: CNc1nc(-c2ccc(S(=O)(=O)N3CCCCC3)cc2)cs1] | NT | | NT |
| 91 | 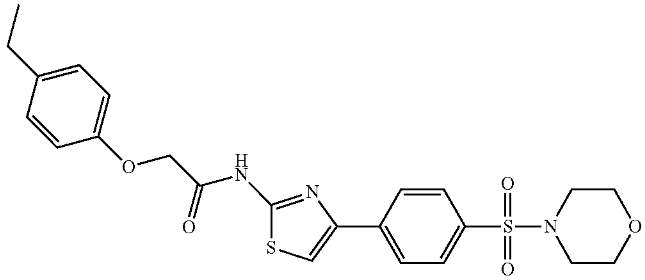 [SMILES: CCc1ccc(OCC(=O)Nc2nc(-c3ccc(S(=O)(=O)N4CCOCC4)cc3)cs2)cc1] | NT | | NT |

TABLE 4-continued

| Comp. | Structure | FAS-TE inhibition (IC$_{50}$) (μM) | n | SEM |
|---|---|---|---|---|
| 92 | 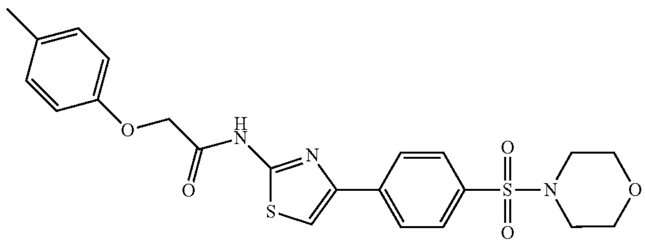 [SMILES: Cc1ccc(OCC(=O)Nc2nc(-c3ccc(S(=O)(=O)N4CCOCC4)cc3)cs2)cc1] | NT | NT | |
| 93 | 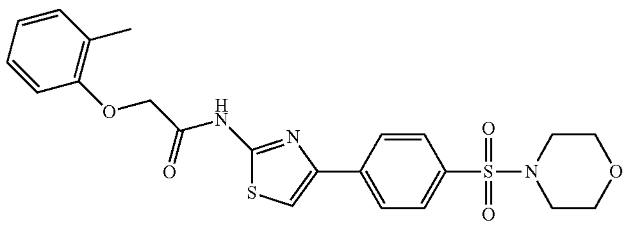 [SMILES: Cc1ccccc1OCC(=O)Nc1nc(-c2ccc(S(=O)(=O)N3CCOCC3)cc2)cs1] | NT | NT | |
| 94 | 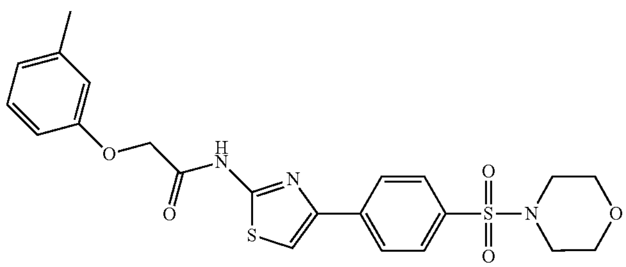 [SMILES: Cc1cccc(OCC(=O)Nc2nc(-c3ccc(S(=O)(=O)N4CCOCC4)cc3)cs2)c1] | NT | NT | |
| 95 | 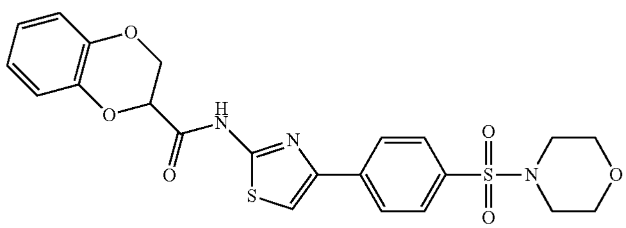 [SMILES: O=C(Nc1nc(-c2ccc(S(=O)(=O)N3CCOCC3)cc2)cs1)C1COc2ccccc2O1] | NT | NT | |
| 96 | 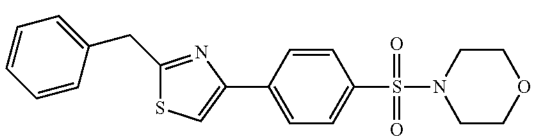 [SMILES: O=S(=O)(c1ccc(-c2csc(Cc3ccccc3)n2)cc1)N1CCOCC1] | 0.66 | 4 | 0.05 |
| 97 | 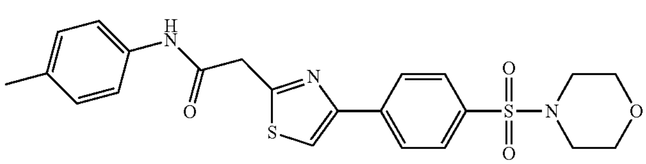 [SMILES: Cc1ccc(NC(=O)Cc2nc(-c3ccc(S(=O)(=O)N4CCOCC4)cc3)cs2)cc1] | 80 | 4 | — |
| 98 | 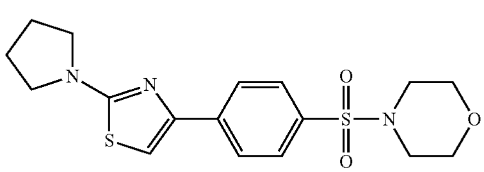 [SMILES: O=S(=O)(c1ccc(-c2csc(N3CCCC3)n2)cc1)N1CCOCC1] | 1.18 | 4 | 0.05 |

TABLE 4-continued
| Comp. | Structure | FAS-TE inhibition (IC$_{50}$) (μM) | n SEM |
|---|---|---|---|
| 99 | 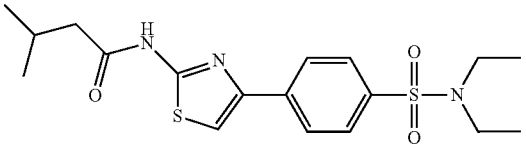 [SMILES: CCN(CC)S(=O)(=O)c1ccc(-c2csc(NC(=O)CC(C)C)n2)cc1] | 19.00 | 1 — |
| 100 | 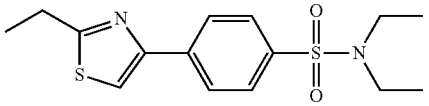 [SMILES: CCc1nc(-c2ccc(S(=O)(=O)N(CC)CC)cc2)cs1] | 80 | 3 — |
| 101 | 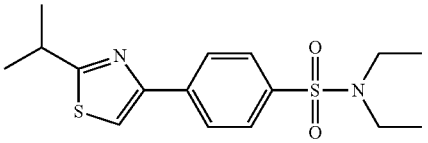 [SMILES: CCN(CC)S(=O)(=O)c1ccc(-c2csc(C(C)C)n2)cc1] | 11.42 | 3 2.46 |
| 102 | 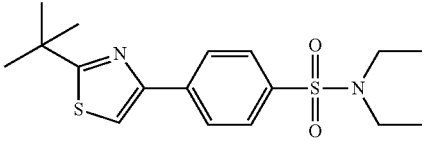 [SMILES: CCN(CC)S(=O)(=O)c1ccc(-c2csc(C(C)(C)C)n2)cc1] | 12.58 | 3 0.97 |
| 103 | 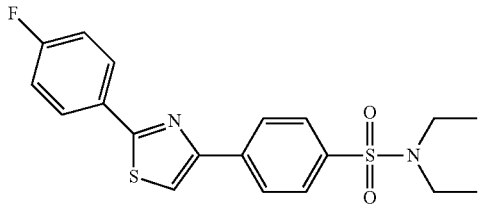 [SMILES: CCN(CC)S(=O)(=O)c1ccc(-c2csc(-c3ccc(F)cc3)n2)cc1] | 1.11 | 3 0.67 |
| 104 | 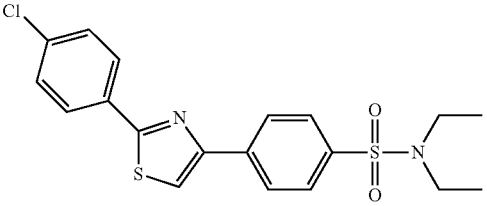 [SMILES: CCN(CC)S(=O)(=O)c1ccc(-c2csc(-c3ccc(Cl)cc3)n2)cc1] | 80 | 1 — |
| 105 | 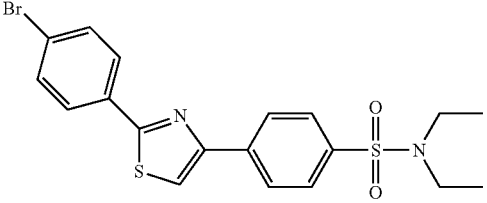 | 80 | 1 — |
| 106 | 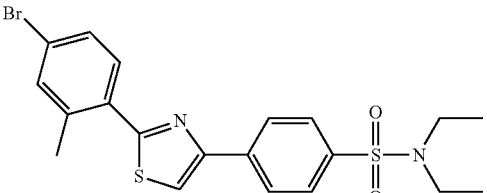 | 80 | 1 — |

TABLE 4-continued
| Comp. | Structure | FAS-TE inhibition (IC$_{50}$) (µM) | n | SEM |
|---|---|---|---|---|
| 107 | 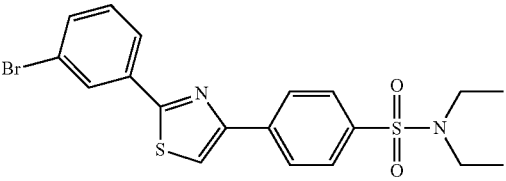 [SMILES: CCN(CC)S(=O)(=O)c1ccc(-c2csc(-c3cccc(Br)c3)n2)cc1] | 80 | 1 | — |
| 108 | 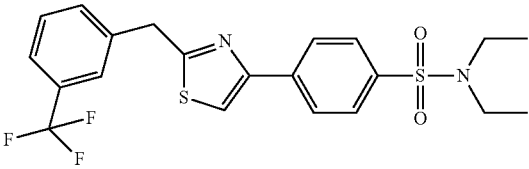 [SMILES: CCN(CC)S(=O)(=O)c1ccc(-c2csc(Cc3cccc(C(F)(F)F)c3)n2)cc1] | 80 | 1 | — |
| 109 | 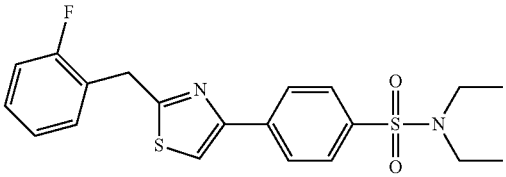 [SMILES: CCN(CC)S(=O)(=O)c1ccc(-c2csc(Cc3ccccc3F)n2)cc1] | 1.72 | 3 | 0.75 |
| 110 | 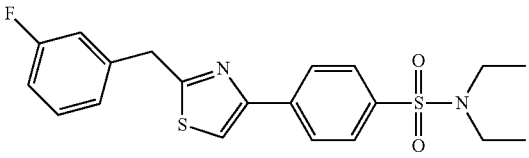 | 3.15 | 3 | 1.10 |
| 111 | 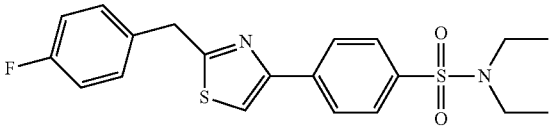 [SMILES: CCN(CC)S(=O)(=O)c1ccc(-c2csc(Cc3ccc(F)cc3)n2)cc1] | 2.41 | 3 | 1.01 |
| 112 | 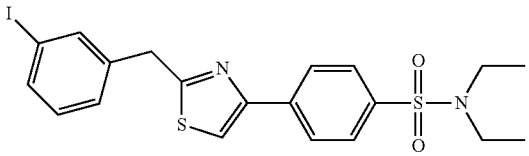 [SMILES: CCN(CC)S(=O)(=O)c1ccc(-c2csc(Cc3cccc(I)c3)n2)cc1] | 5.01 | 2 | 1.69 |
| 113 | 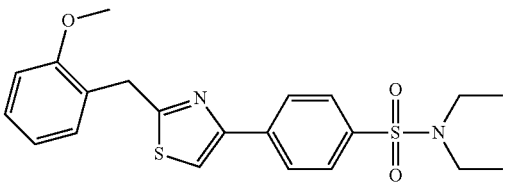 [SMILES: CCN(CC)S(=O)(=O)c1ccc(-c2csc(Cc3ccccc3OC)n2)cc1] | 6.92 | 2 | 0.68 |
| 114 | 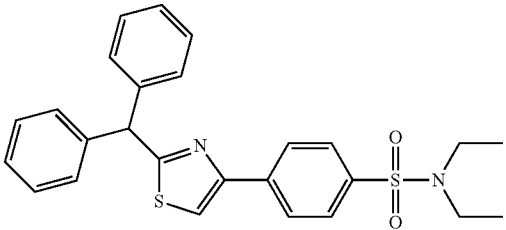 [SMILES: CCN(CC)S(=O)(=O)c1ccc(-c2csc(C(c3ccccc3)c3ccccc3)n2)cc1] | 80 | 2 | 1.30 |

TABLE 4-continued

| Comp. | Structure | FAS-TE inhibition (IC$_{50}$) (μM) | n SEM |
|---|---|---|---|
| 115 | 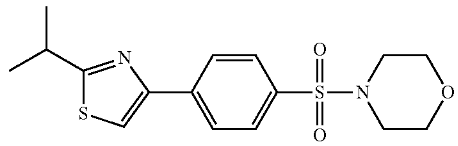 [SMILES: CC(C)c1nc(-c2ccc(S(=O)(=O)N3CCOCC3)cc2)cs1] | 21.68 | 3 7.30 |
| 116 | 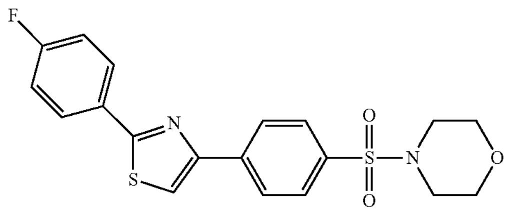 [SMILES: O=S(=O)(c1ccc(-c2csc(-c3ccc(F)cc3)n2)cc1)N1CCOCC1] | 1.48 | 3 0.67 |
| 117 | 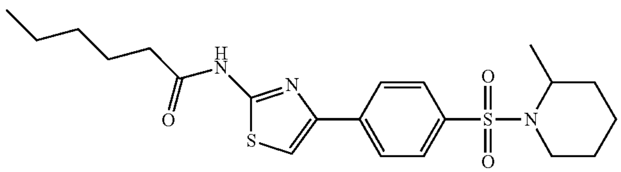 [SMILES: CCCCCC(=O)Nc1nc(-c2ccc(S(=O)(=O)N3CCCCC3C)cc2)cs1] | NT | NT |
| 118 | 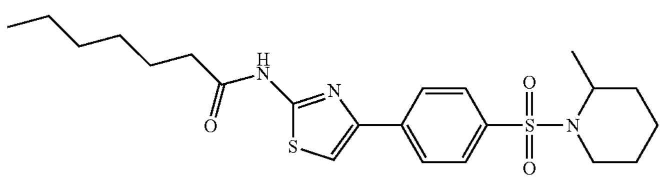 [SMILES: CCCCCCC(=O)Nc1nc(-c2ccc(S(=O)(=O)N3CCCCC3C)cc2)cs1] | NT | NT |

NT = Not tested.

Example B2: Cellular Activity in PC-3 Prostate Cancer Cells

The ability of compounds to block biosynthesis of palmitate in whole cells (prostate cancer PC-3 cells) was measured by feeding cells isotopically labeled glucose ($^{13}$C-glucose) and measuring the incorporation of $^{13}$C into palmitate by GC-MS.

Prostate cancer PC-3 cell were incubated with 20 μM of FASN inhibitors and labeled with [U-13C]-glucose for 24 h, pH 7.8. The incorporation of $^{13}$C into palmitate from labeled glucose was determined by extracting fatty acids and resolving them by GC-MS. The mass distributions for fatty acid methyl esters for C16:0 (palmitate) were corrected for isotope natural abundance, and the corrected isotope patterns were used to calculate the labeling of acetyl-CoA in palmitate based on a binomial probability distribution of the incorporation of labeled acetyl units into the fatty acid chain. Results are presented as the % of de novo palmitate synthesis in relation to the uninhibited control containing vehicle (DMSO) in table 5. These assay indicate the inhibitory activity of compound 1 and compound 16 in whole cell, whereas inactive analog 97 did not inhibit palmitate synthesis.

TABLE 5

| Compound | de novo palmitate synthesis/DMSO (%) |
|---|---|
| 1 | 40 |
| 16 | 50 |
| 97 | 95 |

Figure 2:
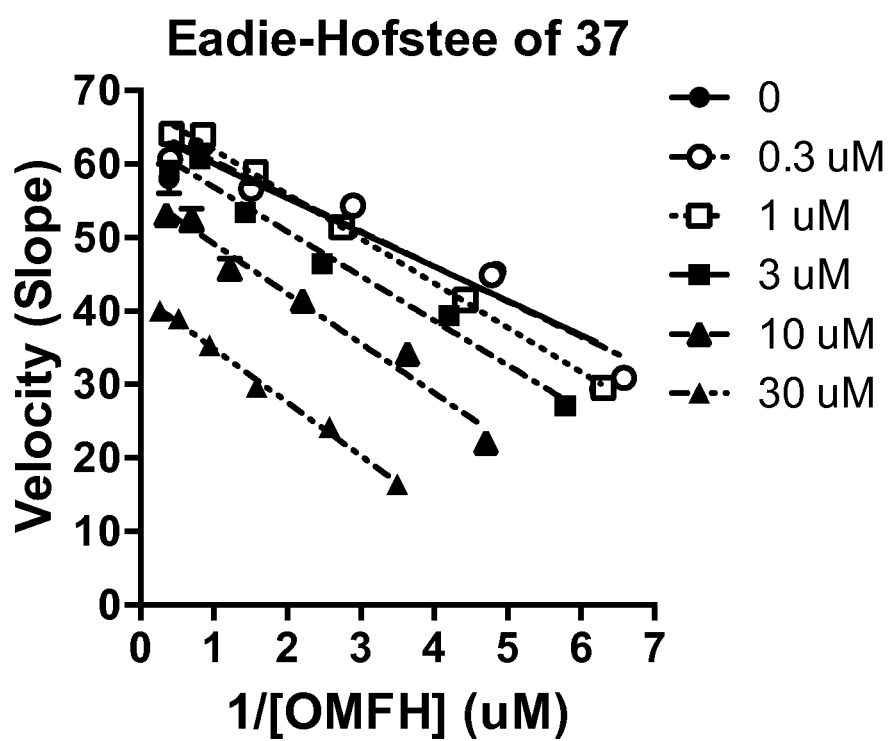
FIG. 2 shows an Eadie-Hofstee analysis of compound 37 with FASN-TE (graphical representation of enzyme kinetics in which reaction rate is plotted as a function of the ratio between rate and substrate concentration).

Additionally, the modulation of palmitate synthesis directly by compound 37 dose-dependently inhibits palmitate synthesis in PC-3 tumor cells (see FIG. 1). Furthermore, using a classical enzymology analysis (Eadie-Hofstee) compound 37 was determined to have a non-competitive mode of inhibition (see FIG. 2).

Example B3: Selectivity Assay Over Other Human Thioesterase

Studies were conducted to determine the selectivity of compound 16 for FASN over other human thioesterases. The ability of the compounds to bind the FASN holoenzyme was tested by assessing their ability to compete for the binding of an activity-based probe that covalently attaches to the active site of the FASN thioesterase. Thioesterases are members of the serine hydrolase family, which also includes a number of other types of enzymes including proteases, dipeptidyl peptidases, epoxide hydrolases, etc. To help assess the selectivity of compound 16, an activity-based probe polyethyleneglycol-6-carboxytetramethyl-rhodamine (FP-PEG-TAMRA) that binds covalently to the catalytic serine of all serine hydrolases was used. These studies were done by assessing the ability of compound 16 to compete for the binding of the activity-based probe in whole cell lysates. Several analogs of compound 16 were tested in this assay using lysates of the prostate tumor line (PC3), which expresses FASN, along with numerous other serine hydrolases. The PC-3 lysate was incubated with 8 different FASN inhibitors, including compounds 1, 16 and 97. Then the activity-based probe (FP-PEG-TAMRA) was added to each sample to label the serine hydrolases in the lysate. Samples were resolved by 10% SDS-PAGE and activity-based labeling was visualized at 535 nm Compound 16 and compound 1 (all compounds at 20 µM final, pH 7.8) showed inhibition of FASN, whereas an inactive control compound did not (compound 97). These results show that compound 16 and key analogs block the binding of FP-TAMRA to FASN. However, there is no competition for activity based labeling against any of the other serine hydrolases in the lysate. These findings indicate that compound 16 is highly selective for the thioesterase domain of FASN (FASN-TE).

Figure 3:
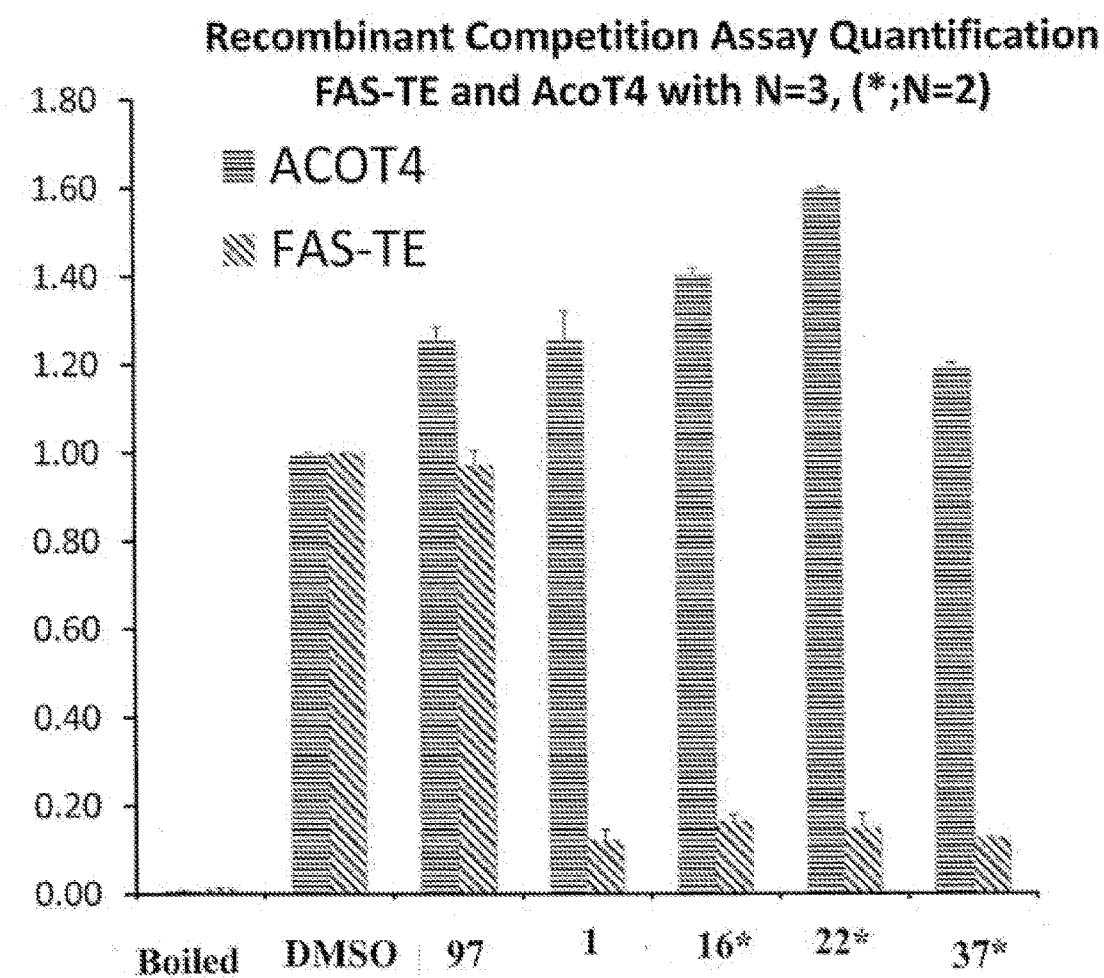
FIG. 3 shows selectivity for recombinant FASN-TE and ACOT4 for compounds 1, 16, 22 and 37. Compound 97 had no activity in the enzyme-based assay and was used as a negative control.

Additionally, studies were performed to test the selectivity of Compounds 1, 16, 22, and 37 for the FASN thioesterase over its most closely related human homolog, the enzyme called ACOT4 (see FIG. 3). Both proteins were mixed and pretreated with the compound (20 µM final, pH 7.8) before addition of the fluorescent activity probe FP-PEG-TAMRA. Respective fluorescence of the bands was detected on a Hitachi flatbed scanner and a greyscale version used for quantitative analysis using ImageJ. Recombinant forms of each enzyme were incubated with compound 16, compound 1, compound 37, and compound 22. FP-TAMRA was included in this mixture to label the active site of the FASN thioesterase and ACOT4. Compound 16, compound 1, compound 37, and compound 22 blocked the binding of FP-TAMRA to the active site of the FASN thioesterase but were without effect on activity labeling of ACOT4. These findings further attest to the high degree of selectivity of compounds 1, 16, 37 and 22 for the FASN thioesterase.

Figure 4:
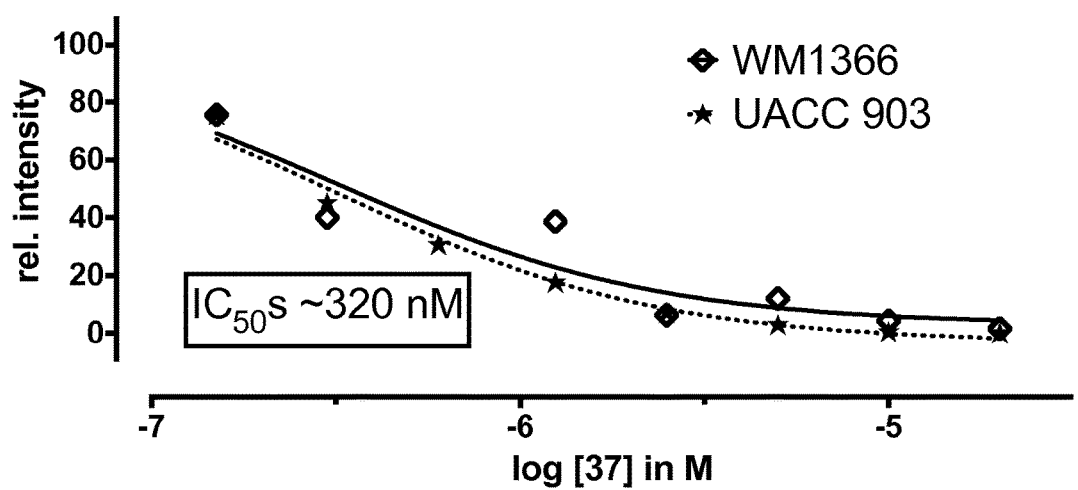
FIG. 4 shows the dose response curve of 37 in cell lysate assay of WM1366 and UACC 903 melanoma cell lines.

The dose response curve of compound 37 in cell lysate assay of WM1366 and UACC 903 melanoma cell lines in shown in FIG. 4. To further evaluate selectivity and identify any off-target effects, compound 37 was tested against a commercial panel of 34 binding assays (enzymes, receptors & ion channels) through Eurofins Panlabs. Only two binding interactions>50% were noted at 10 µM: CYP450 2C19 (50%) and sodium channel (74%). Compound 37 was also tested in a commercial panel of 17 diverse proteases (Reaction Biology). Only one interaction up to 100 µM was noted: chymotrypsin inhibition (IC50=1.7 µM).

Example B4: Profiling Assays

Compound 16 was evaluated in a detailed in vitro pharmacology screen as shown in Table 6:

TABLE 6

Summary of in vitro ADME Properties of FAS-TE inhibitor compound 16

| | |
|---|---|
| Aqueous Solubility in pION's buffer (µg/mL) [µM]$^a$ pH 5.0/6.2/7.4 | 0.19/0.06/0.13 [0.45/0.14/0.31] |
| Aqueous Solubility in 1x PBS, pH 7.4 (µg/mL) [µM]$^a$ | 0.02 [0.05] |
| Chemical Stability in 1x PBS pH 7.4/with 50% ACN (% remaining after 48 hrs) | 100/100 |
| PAMPA Permeability, Pe (×10$^{-6}$ cm/s) Donor pH: 5.0/6.2/7.4 Acceptor pH: 7.4 | 914/961/653 |

TABLE 6-continued

Summary of in vitro ADME Properties of FAS-TE inhibitor compound 16

| | |
|---|---|
| Plasma Protein Binding (% Bound) Human 1 µM/10 µM | 96.60/97.47 |
| Mouse 1 µM/10 µM | 96.19/96.63 |
| Plasma Stability (% Remaining at 3 hrs) Human/Mouse | 100/100 |
| Hepatic Microsome Stability (% Remaining at 1 hr) Human/Mouse | 4.93/6.37 |
| Toxicity Towards Fa2N-4 Immortalized Human Hepatocytes LC$_{50}$ (µM) | >50 |

$^a$Solubility also expressed in molar units (µM) as indicated in italicized [bracketed values], in addition to more traditional µg/mL units.

The PAMPA (Parallel Artificial Membrane Permeability Assay) assay was used as an in vitro model of passive, transcellular permeability. An artificial membrane immobilized on a filter was placed between a donor and acceptor compartment. At the start of the test, drug was introduced in the donor compartment. Following the permeation period, the concentration of drug in the donor and acceptor compartments was measured using UV spectroscopy. Compound 16 exhibited very good permeability across a range of pH of the donor compartment.

Plasma protein binding was a measure of a drug's efficiency to bind to the proteins within blood plasma. The less bound a drug is, the more efficiently it can traverse cell membranes or diffuse. Highly plasma protein bound drugs are confined to the vascular space, thereby having a relatively low volume of distribution. In contrast, drugs that remain largely unbound in plasma are generally available for distribution to other organs and tissues. Compound 16 was highly plasma protein bound.

Plasma stability is a measure of the stability of small molecules and peptides in plasma and is an important parameter, which can strongly influence the in vivo efficacy of a test compound. Drug candidates are exposed to enzymatic processes (proteinases, esterases) in plasma, and they can undergo intramolecular rearrangement or bind irreversibly (covalently) to proteins. Compound 16 showed good stability in both human plasma and mouse plasma.

The microsomal stability assay is commonly used to rank compounds according to their metabolic stability. This assay addresses the pharmacologic question of how long the parent compound will remain circulating in plasma within the body. Compound 16 showed poor stability in human and mouse liver microsomes.

Compound 16 showed no toxicity (>50 µM) towards immortalized Fa2-N4 human hepatocytes.

Example B5: Pharmacokinetic Studies

A pharmacokinetic (PK) study of Compound 37 dosed systemically (IP) in mice was conducted. At 10 mg/kg (IP) compound 37 attained plasma levels post dosing of >3 µM up to 30 min., >2 µM up to 1 h, and >1 µM up to 2 h.

Example B6: Melanoma Xenograft Model

Three N-Ras melanoma cell lines were used for xenograft testing: the WM1366 and WM853 lines, both of which have mutated N-Ras, but only WM1366 is PTEN deficient; and the WM35 line, which has mutated B-Raf, but not mutated N-Ras. This choice of cells for first-pass xenograft testing allows for the evaluation of compounds in vivo, and helps select a compound that can ultimately be tested in genetic models of N-Ras mutated melanoma, in addition to other types of tumors.

Example B7: Dosing Regimen for Testing FASN Inhibitors in Xenograft Models

The dosing regimen that maintained inhibition of FASN in tumor cells (the pharmacodynamic, or PD, response) was determined by using two approaches: activity-based proteomics and measurement of palmitate synthesis in the tumor. This "PK/PD" readout made it possible to i) determine the compound levels in blood that correlate with inhibition of FASN in tumors; ii) determine what level of inhibition is required for blocking tumor growth in vivo; and iii) determine if the compound has any off-target activity in tumors. Compounds are were tested at three doses based on PK data. The first dose of compound equated to a level that achieves a plasma concentration equivalent to the cellular $IC_{50}$ of the compound for at least 8 h. The second dose extended five-fold over, and the third dose 10-fold over the cellular $IC_{50}$, provided the compounds have suitable solubility.

Example B8: Level of Inhibition of the FASN-TE with Activity-Based Proteomics Compounds were tested in mice bearing xenografts of melanoma cells described above. Tumor xenografts were established in a group of 16 nude mice (4 controls and 3 test groups of 4 animals). Studies were initiated when tumors grow to approximately 0.25 mm³, a size that is visible on the flank, but small enough so that the tumor did not contain a substantial necrotic core. Compounds were tested at three doses based on PK data obtained. Three mice were used per dose for analysis by activity based proteomics. Animals were injected with compound, and 2 h later the animals were sacrificed and the tumor resected on ice. Tumor tissue was lysed by brief sonication, and then the activity-based probe FP-TAMRA were incubated with the lysate for 2 h. The homogenate were lysed with detergent and analyzed by SDS-PAGE, allowing us to visualize the serinehydrolases in the tumor tissue whose active site was blocked by compound. This analysis showed whether the FASN-TE was blocked, and to what level, by the dose of drug administered.

Example B9: Palmitate Biosynthesis in Tumor Xenografts

The de novo synthesis of palmitate in tumors in vivo via injection was measured with universally labeled [$^{13}$C]-glucose and by tracking the incorporation of isotope into palmitate by GC-MS. It requires ~24 h for glucose to traverse the TCA cycle and make a measurable contribution to the carbon in palmitate. Universally labeled-[$^{13}$C]-glucose (200 μL of 0.6 M $^{13}$C-glucose) was injected directly into the tumor every two hours for 12 hours. Tumors will be extracted 24 h after the first injection of glucose, and the level of [$^{13}$C] present in palmitate was measured with GC-MS. The level of palmitate synthesized per milligram of tumor protein was calculated for each treatment group and timepoint. In these experiments, 8 animals were used: 4 untreated controls injected intratumor with [$^{13}$C]-glucose, and 4 injected with glucose and treated with compound.

Example B10: Efficacy of FASN Inhibitors in Xenograft Models of N-Ras Melanoma The anti-tumor effects of selected FASN-TE inhibitors was measured in orthotopic xenograft models using the three human melanoma cell lines described above. Each test had two arms: one control and one for the test compound. Power calculations, based on published results on xenograft growth for the chosen melanoma lines, indicated that a group size of 12 animals was required to provide an 80% chance of detecting a reduction in tumor growth of 60%. However, some animals were anticipated to die for unexpected reasons, and in others the tumor will not take. Therefore, the study started with 15 animals in each arm. Melanoma cells (1×10⁶) was injected into the dorsal region of BALB/c athymic nude mice. Tumors will be allowed to grow to a size of approximately 100 mm³ (which is a point just after which they are palpable) before compound dosing was initiated. This ensured that the tumor had begun to grow in all animals that were administered compound, and also reduced the statistical variability in measuring tumor growth. Moreover, by initiating dosing after substantial tumor growth in vivo, we better mimic the human clinical condition. Each animal was treated with test compound or vehicle for approximately 2-3 weeks, at which time untreated xenografts typically grew to a size of 200 to 300 mm³. Tumor volumes were measured three times a week at orthogonal angles to calculate tumor volumes ($V=\pi/6 \times XY^2$), which was then be used to calculate tumor-doubling time. The differences in tumor growth were considered and determined significant if the observed p-value of less than 0.05 with Students t-test between test and control groups.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound which has one of the following structures, or a pharmaceutically acceptable salt, or solvate thereof:

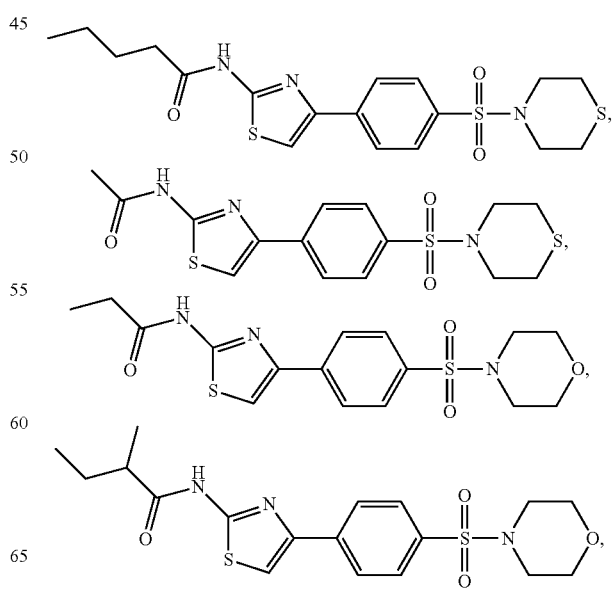

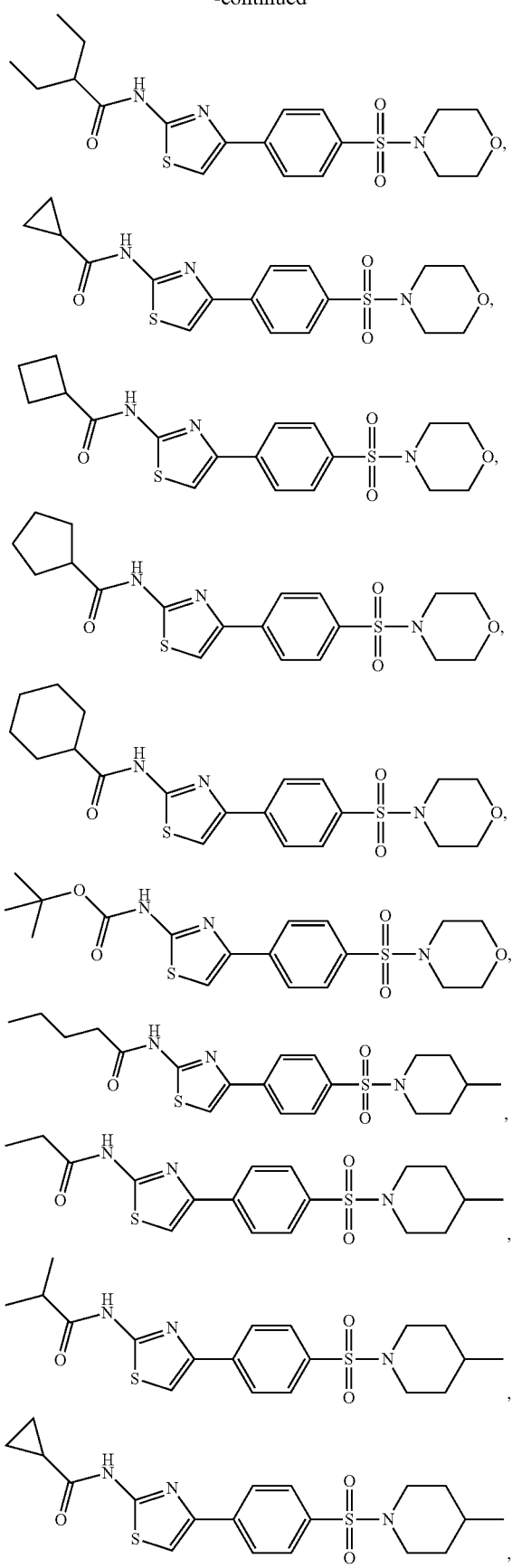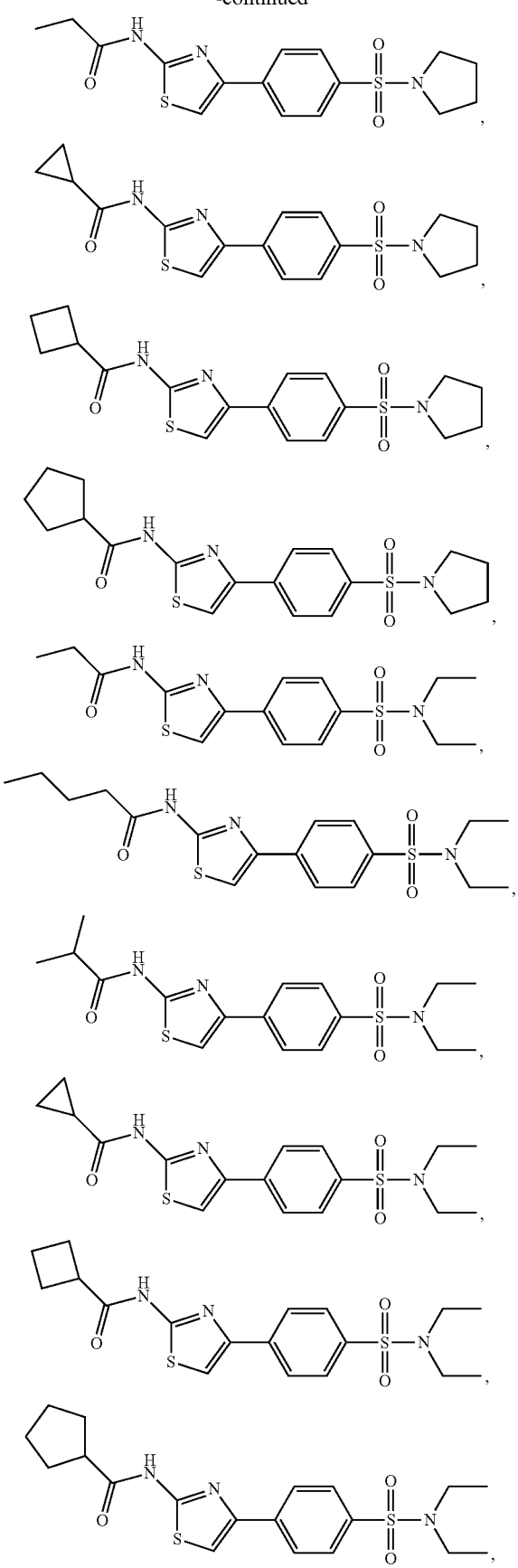

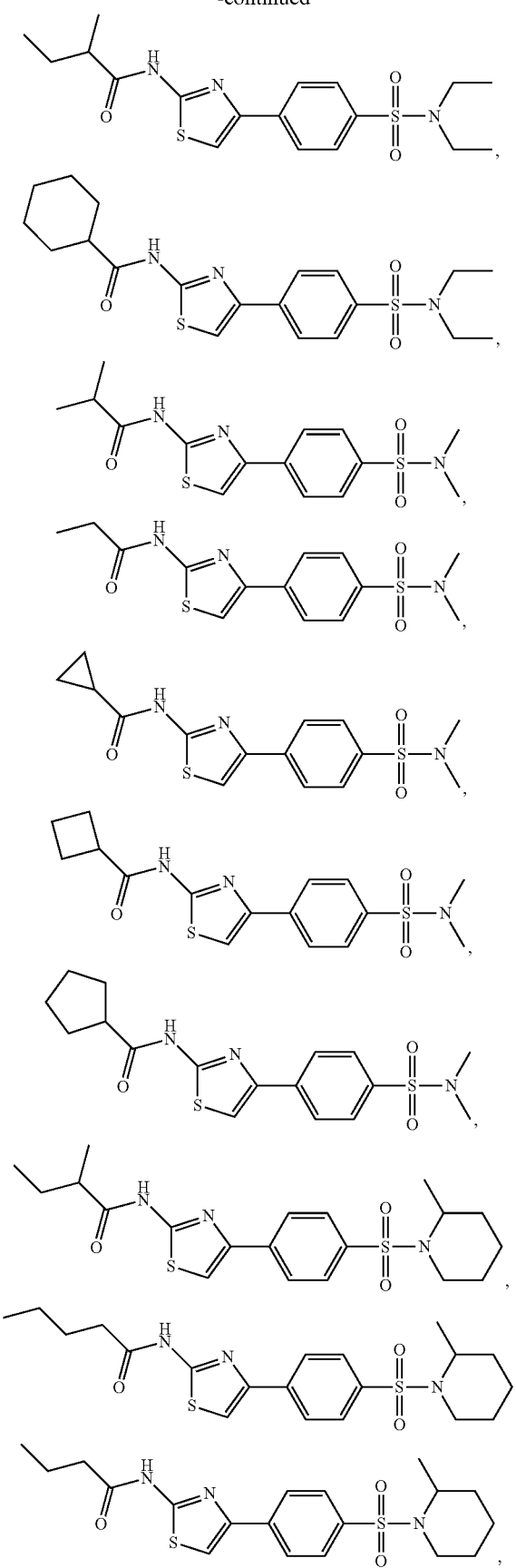
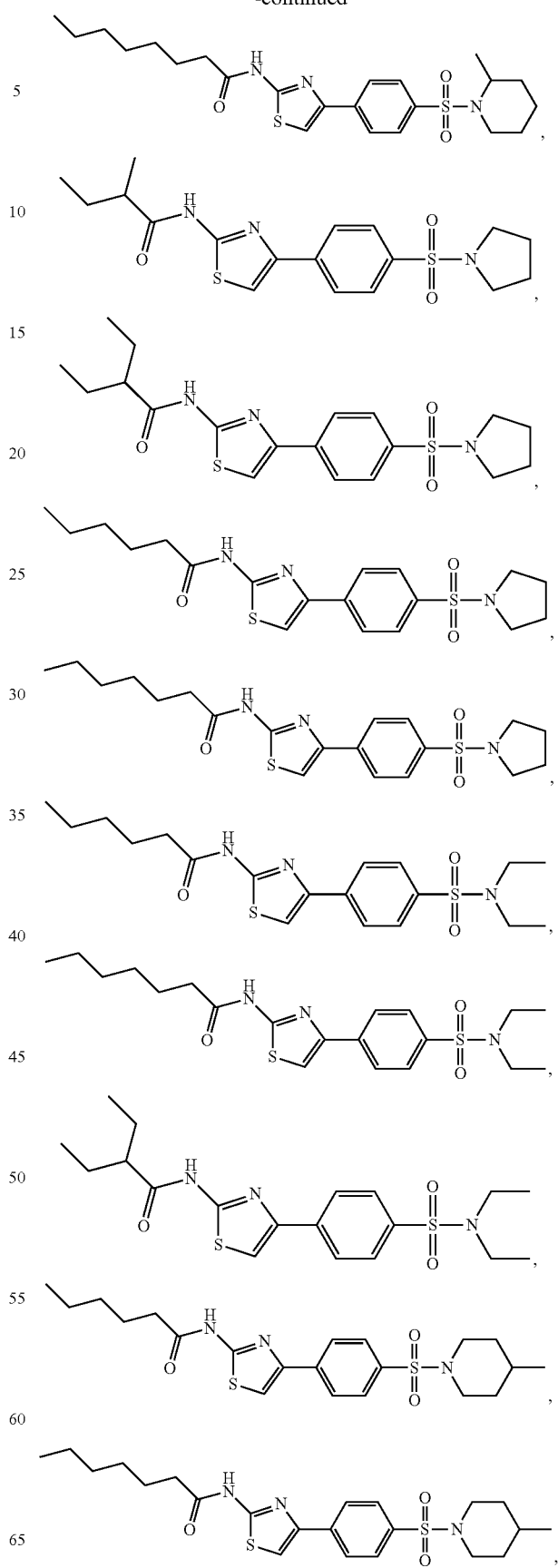

-continued
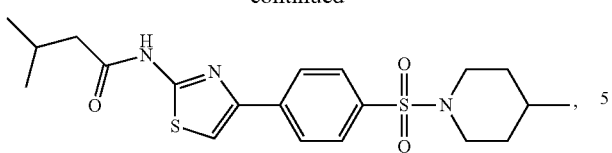
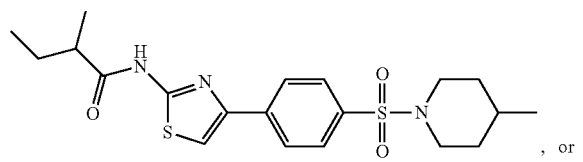, or
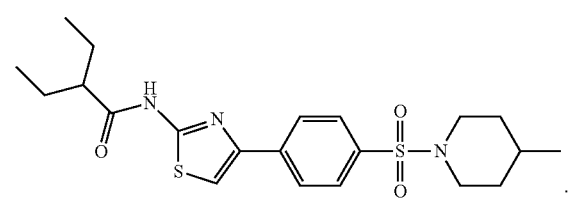 [SMILES: CCC(CC)C(=O)Nc1nc(-c2ccc(S(=O)(=O)N3CCC(C)CC3)cc2)cs1].
2. A compound which has one of the following structures, or a pharmaceutically acceptable salt, or solvate thereof:
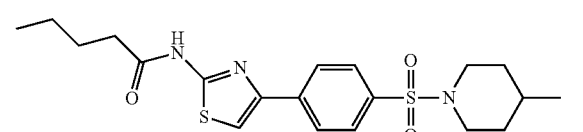,
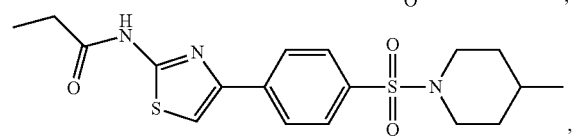,
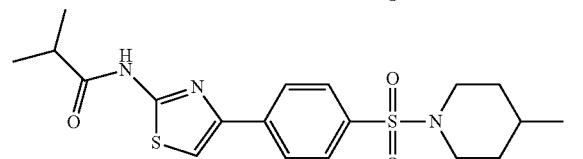,
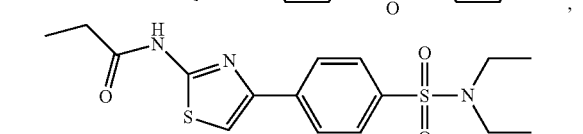,
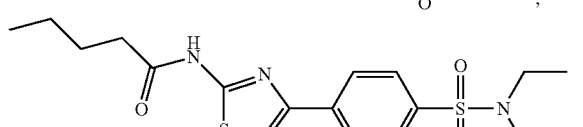,
,
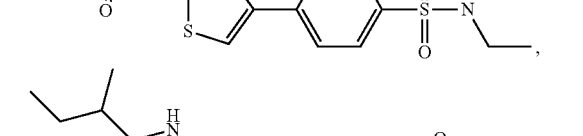,
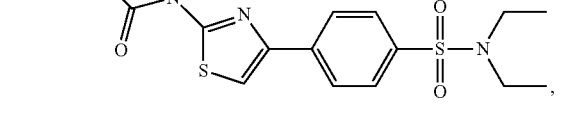,
-continued
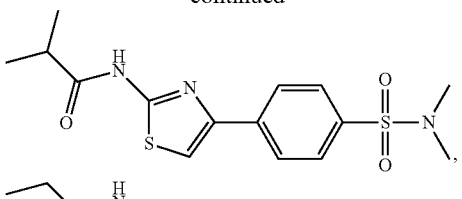,
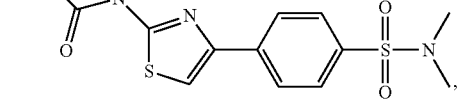,
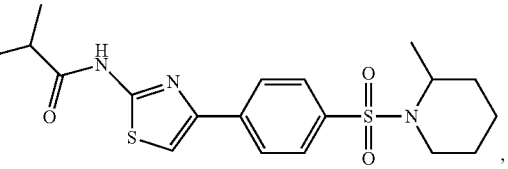,
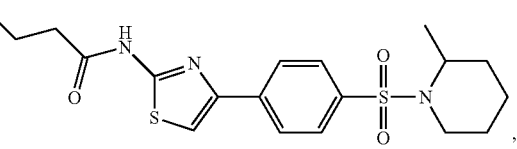, -continued

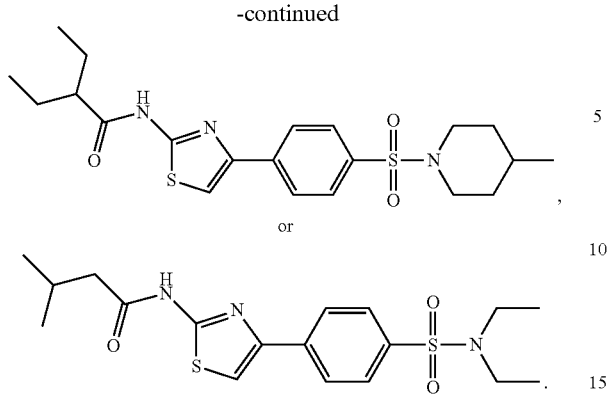

or

3. A pharmaceutical composition comprising a compound of claim 1, or a pharmaceutically acceptable salt, or solvate thereof, and at least one pharmaceutically acceptable diluent, excipient or binder.

4. A pharmaceutical composition comprising a compound of claim 2, or a pharmaceutically acceptable salt, or solvate thereof, and at least one pharmaceutically acceptable diluent, excipient or binder.

* * * * *